US012029631B1

(12) United States Patent
Ward et al.

(10) Patent No.: US 12,029,631 B1
(45) Date of Patent: Jul. 9, 2024

(54) WETNESS PAD ASSEMBLY, SYSTEM AND METHOD

(71) Applicant: AlertWet LLC, Anchorage, AK (US)

(72) Inventors: Franklin Edward Ward, Anchorage, AK (US); Kimberly Dawn Gray, Anchorage, AK (US)

( * ) Notice: Subject to any disclaimer, the term of this patent is extended or adjusted under 35 U.S.C. 154(b) by 125 days.

(21) Appl. No.: 17/231,564

(22) Filed: Apr. 15, 2021

Related U.S. Application Data

(60) Provisional application No. 63/033,610, filed on Jun. 2, 2020.

(51) Int. Cl.
| | |
|---|---|
| *A61F 13/42* | (2006.01) |
| *A61F 13/04* | (2006.01) |
| *A61F 13/84* | (2006.01) |
| *G01N 27/22* | (2006.01) |
| *H05K 1/02* | (2006.01) |

(52) U.S. Cl.
CPC .......... *A61F 13/42* (2013.01); *G01N 27/223* (2013.01); *H05K 1/0228* (2013.01); *A61F 13/041* (2013.01); *A61F 2013/424* (2013.01); *A61F 2013/8482* (2013.01); *H05K 2201/09227* (2013.01)

(58) Field of Classification Search
CPC ................ A61F 13/42; A61F 2013/424; A61F 2013/8482; A61F 13/041; G01N 27/223; H05K 1/0228; H05K 2201/09227
USPC ............................................... 340/604, 573.5
See application file for complete search history.

(56) References Cited

U.S. PATENT DOCUMENTS

| | | | | |
|---|---|---|---|---|
| 5,211,747 A | * | 5/1993 | Breton .................... | C09D 11/30 347/100 |
| 5,537,095 A | * | 7/1996 | Dick .......................... | A61F 5/48 340/573.5 |
| 5,762,641 A | * | 6/1998 | Bewick-Sonntag ......................... | A61F 13/53717 604/378 |
| 6,544,200 B1 | * | 4/2003 | Smith .................. | A61B 5/6892 600/595 |
| 9,901,488 B1 | * | 2/2018 | Levin ...................... | A61B 5/447 |
| 10,478,349 B2 | * | 11/2019 | Mancini .................. | A61F 13/42 |
| 2007/0024457 A1 | * | 2/2007 | Long ........................ | A61F 13/42 340/605 |

(Continued)

FOREIGN PATENT DOCUMENTS

| | | | | |
|---|---|---|---|---|
| CN | 101166495 A | * | 4/2008 | ............. A61F 13/42 |
| WO | WO-2005017683 A2 | * | 2/2005 | ........... A61B 5/0002 |

(Continued)

*Primary Examiner* — Susan S Su
*Assistant Examiner* — Ted Yang
(74) *Attorney, Agent, or Firm* — Quarles & Brady LLP

(57) ABSTRACT

A sensor pad assembly for detecting wetness, the pad assembly comprising a breathable polyethylene base layer, a first carbon black trace printed on a top surface of the base layer in a serpentine pattern, a second carbon black trace printed on the top surface of the base layer in a serpentine pattern that does not overlap the first trace, wherein at least a portion of the second trace is adjacent each portion of the first trace and an absorbing subassembly including non-woven layers that envelope a super absorbent polymer (SAP) material, the absorbing subassembly adhered to the top surface of the base layer over the first and second traces.

27 Claims, 47 Drawing Sheets

(56) References Cited

U.S. PATENT DOCUMENTS

| | | | | |
|---|---|---|---|---|
| 2007/0142796 | A1* | 6/2007 | Mosbacher | A61F 13/42 604/361 |
| 2013/0036802 | A1* | 2/2013 | Johnson | A61F 13/42 73/74 |
| 2013/0041334 | A1* | 2/2013 | Prioleau | A61F 13/42 604/361 |
| 2014/0207096 | A1* | 7/2014 | Love | A61G 7/057 604/374 |
| 2014/0262774 | A1* | 9/2014 | Bhatia | G01N 27/07 204/403.01 |
| 2014/0371702 | A1* | 12/2014 | Bosaeus | A61F 13/51484 604/385.01 |
| 2017/0112681 | A1* | 4/2017 | Mancini | A61F 13/42 |
| 2017/0236398 | A1* | 8/2017 | Eddy | A61B 5/202 340/573.5 |
| 2018/0021184 | A1* | 1/2018 | Monson | A61G 7/015 340/573.5 |
| 2018/0116879 | A1* | 5/2018 | Williams | A61F 13/42 |
| 2019/0038478 | A1* | 2/2019 | Lai | A61B 5/6808 |
| 2019/0051137 | A1* | 2/2019 | Kilcran | A61F 13/42 |
| 2019/0060137 | A1* | 2/2019 | Severns | A61F 13/15203 |
| 2019/0212311 | A1* | 7/2019 | Hammond | G01N 21/80 |
| 2019/0240078 | A1* | 8/2019 | Li | G01B 7/02 |
| 2019/0240080 | A1* | 8/2019 | Tuli | A61F 13/42 |
| 2020/0001080 | A1* | 1/2020 | Naitoh | A61N 1/36007 |
| 2020/0038254 | A1* | 2/2020 | Mancini | A61F 13/42 |
| 2020/0093411 | A1* | 3/2020 | Stevens | A61B 5/202 |
| 2020/0276063 | A1* | 9/2020 | Muñoz Herencia | A61F 13/58 |

FOREIGN PATENT DOCUMENTS

| | | | | |
|---|---|---|---|---|
| WO | WO-2006118913 | A1 * | 11/2006 | A61F 13/42 |
| WO | WO-2017217859 | A1 * | 12/2017 | A61F 13/42 |

\* cited by examiner

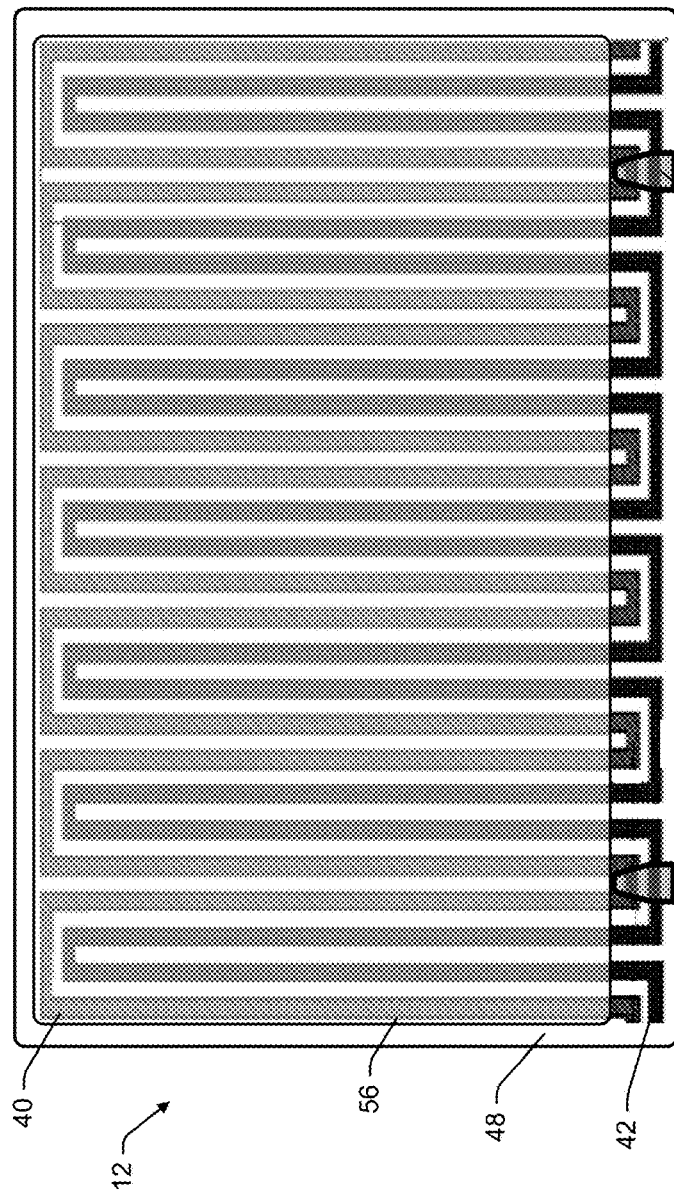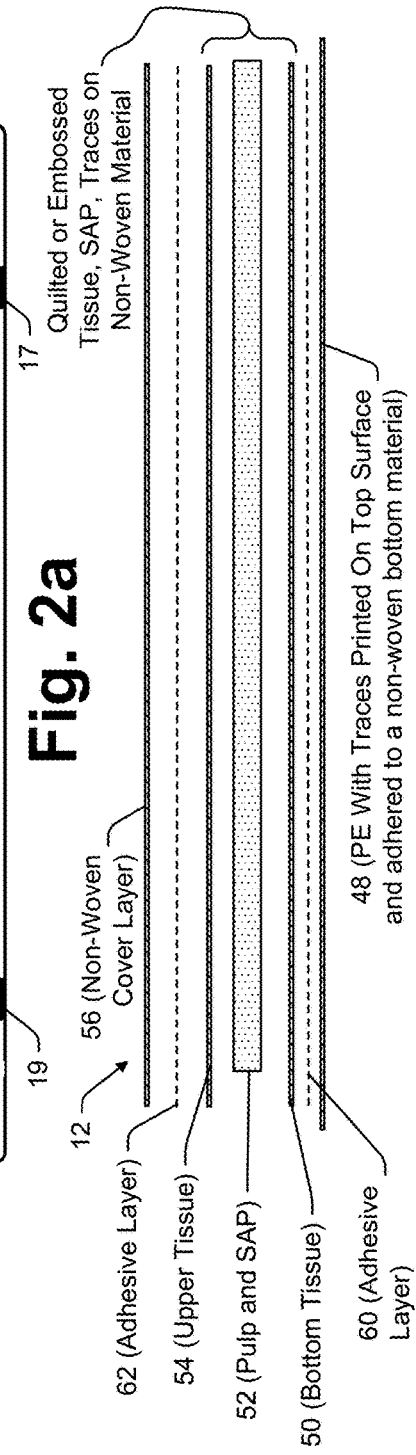

WETNESS PAD ASSEMBLY, SYSTEM AND METHOD

CROSS-REFERENCE TO RELATED APPLICATIONS

This application is related to and claims priority to U.S. provisional patent application Ser. No. 63/033,610 which was filed on Jun. 2, 2020 which is titled "Wetness Pad Assembly, System and Method" which is incorporated herein in its entirety by reference.

BACKGROUND OF THE DISCLOSURE

The field of the disclosure is wetness detection and more specifically disposable wetness detection systems and methods for use in beds, chairs, wheelchairs or on other user supporting surfaces as well as manufacturing processes useful in configuring assemblies for detecting wetness states.

Many people in hospital beds and some people at home in bed get wet often. In many cases when a person gets wet (i.e. feces, urine, blood, sweat), that person senses the wetness and can either address the problem personally or, in the case of a hospital or even at home, may be able to call for assistance so that the problem can be addressed. While a person that has an incontinence problem may be an admitted patient at a hospital or not, unless indicated otherwise and to simplify this explanation, a person with an incontinence problem will be referred to hereafter as a "patient" and a person that is charged with helping the patient will be referred to as a "healthcare assistant" or just as "an assistant" or a "care giver". In some cases, a healthcare assistant, may be able to detect wetness independent of a patient in a bed (e.g., visually see the problem or sensing the problem in some other fashion). Unfortunately, in some cases, a patient that gets wet in bed is not able to detect the wetness at all or at least for some time. For instance, sometimes a patient may urinate or excrete another liquid while sleeping or a liquid may accidentally be spilled on the patient's bed while sleeping (e.g., a cup may accidentally tip over on an over bed cart) and that patient may not detect the wetness until hours later. As another instance, some patients may not have sensory capability to detect wetness. In other cases, a patient may be drugged to the point where even if she detects wetness, she may not care or may be incapable of signaling for help. In most cases, because of covers or the like, an assistant cannot visually detect wetness.

In addition to making a patient uncomfortable, wetness can lead to rashes, bed sores and, in many cases, infections and sickness or exacerbated sickness. Furthermore, a void on an unprotected bed can destroy a mattress or, at a minimum, can be a mess to clean up.

One solution to deal with wetting issues is for patients to wear diaper type devices while in bed. While diapers work fairly well, they are inconvenient to put on, especially for patients having certain types of problems. In addition, diapers can be uncomfortable to wear and can be embarrassing for some patients.

Another solution is to place a liquid absorbing pad under a patient's midsection while in bed where the pad is designed to wick wetness away from a patient's skin and to soak up a sufficient volume of liquid to minimize the possibility of additional soiling of a mattress or bedding materials. In these cases, eventually pad capacity is reached and pads have to be replaced. While pads work fairly well, they too have shortcomings. First, with standard pads, there is no good way to know when a pad is wet. Second, even if it is known that a pad is wet, it is difficult to determine how wet a pad is other than weighing the pad on a scale. In most cases, minimal wetness that is wicked away from a patient's skin is acceptable for a time and ideally pads are only replaced once wetness nears full absorbing capacity. Third, voiding schedules are not typically known so that pad wetness can happen at any time and volumes of wetness vary over time and with voiding events.

Another solution has been to provide wetness sensor assemblies. For instance, known assemblies provide first and second electrical conductors on a sheet of material that is placed under a patient in bed. A sensor device applies a voltage across the traces and when wetness occurs between the traces, the sensor detects a drop in resistance between the traces and generates a wetness signal. In known systems, these sensor assemblies are fairly expensive and therefore are designed to be cleanable and reusable. While cleanable sensor assemblies are an option, cleaning sensor assemblies to the level required for hospital use is challenging. In addition, the idea of reusing a soiled but "cleaned" sensor assembly makes these options less appealing to many patients as well as-user assistants.

Yet one other solution contemplated has been disposable, single use sensor pad assemblies that can be thrown out once soiled instead of being cleaned and reused. While disposable sensor systems should work in theory, unfortunately they have a several shortcomings that have made these solutions difficult to produce. First, many incontinent patients void fifteen or more times a day so that any disposable solution results in substantial waste generation including pads, sensor components and electronics, etc. Second, because disposable pads need to be used by many patients daily, is it important that any disposable components be relatively inexpensive. In known attempts to produce disposable sensor systems, the sensor systems have not worked well. To this end, sensor pads typically need to be placed under a user in a bed, or under a user on the upper surface of a chair seat, or the like. Many system users are heavy and move while in bed or while seated or otherwise supported on an affordance. Movement subjects sensor pads to substantial friction and tearing forces which can result in damage to sensor traces and ultimately to sensing malfunction. Thus, there is no known disposable wetness sensor solution that works well and instead more robust cleanable solutions have been preferred.

SUMMARY OF THE DISCLOSURE

It has been recognized that a disposable pad can be provided where the pad includes anode and cathode traces that have specific characteristics printed on a pad layer which can be combined with other pad layers so that a resulting low cost pad can withstand forces applied by users that shift their weight around on a top surface or that have their weight shifted around (e.g., via an assistant) on a top surface of the pad. An exemplary pad includes multiple layers of material arranged to perform three functions. First, the layers are selected for wicking wetness away from a user's skin and absorbing that wetness in material that is generally separated from the user's skin. Second, the layers are selected and arranged to stop liquid from breaching the boundaries of the pad and spilling over onto a bed, seat or other surface below the pad. Third, the layers include anode and cathode traces printed on one surface of one pad layer where the trace material and mechanical characteristics (e.g., cross sectional width, print thickness, absorption characteristics, etc.) as well as pad layering together result in a durable sensing structure spaced from the patient's skin and direct frictional forces during use yet within the structural components of the pad that becomes wet when liquid is absorbed.

In addition, in at least some cases, sensing electronics are provided in a sensor clip system where one clip system is utilized per user for a typical maximum duration (e.g., 3 to 6 months) and is then thrown out. Thus, in a typical system, a user may run through 100 s or even thousands of pads over the course of a 3 month period but would only use a single disposable clip reader system. In most cases, the clip reader system operates to periodically (e.g., every second, every minute, every 180 seconds, etc.) collect wetness data which is wirelessly transmitted to a proximate portable computing device (e.g., a smart phone, smart watch, tablet computing device, laptop, etc.) and most processing occurs in the portable computing device.

In some cases the disclosed sensor system will estimate void volume. In some cases the sensor system is capable of detecting location of wetness on a pad area. In some cases the sensor system is capable of detecting when wetness has reached specific portions of a pad like, for instance, a circumferential boundary of the pad. In some cases, the system can track wetness over time to assess when an initial wetness event occurs after new pad use commences, when subsequent wetness events occur, when a critical level of wetness occurs, how long a user remains wet after initial wetness is detected, etc.

In at least some cases the pad assembly includes a sensor assembly as well as liquid capture or absorbing components. In other cases the sensor system may simply include a sensing assembly and be intended for use with a separate pad assembly. Here, the sensor system would operate as a pad liner to be used with a conventional absorbent pad.

In addition to describing optimized disposable sensor pad assemblies, the disclosure describes a new process for constructing a sensor pad assembly.

In at least some systems the sensor system detects changes in resistance or other electrical parameters that change as a wetness state occurs. For instance, in some cases an exemplary pad includes a pair of traces that wind about on a pad surface where there is a known resistance between the traces when the pad is dry. The resistance level between the traces can be detected by applying a small DC voltage thereacross and measuring the resistance level. Once a wet spot occurs on the pad, the liquid within the wet spot causes a short at the location of that spot which changes the resistance detected by a sensing device. In at least some cases the system tracks one or more pad locations associated with a wet spot over time to assess liquid volume accumulating within a pad assembly. In other cases the system can detect several boundary locations of a current wet spot in order to assess size, liquid volume, a defined location on a pad and closeness of the spot edges with respect to boundaries of the pad.

In at least some cases the sensor system is capable of detecting an electrolytic effect when a positive voltage is detected across the anode and cathode traces where the voltage level can be correlated with known chemicals in the liquid so that a system processor can distinguish between liquids of different types such as urine, blood, sweat, and other liquids associated with, among other things, bed sores, skin breakdown, etc. In addition, in at least some cases the sensor is useable to analyze the makeup of a patient's urine including relative relationships of electrolytes such as sodium, chloride and potassium as well as pH of urine. In some cases sensors will detect both resistance and voltage and use those values in different processes to determine different things. These differences in the liquids detected can be used in some cases to identify other patient conditions and, in some cases, those conditions may justify payments from insurance companies to cover costs associated with the sensing system.

Because many users use the disclosed sensor system over time (e.g., for several months), the sensed wetness data can be used in many cases to identify specific user voiding schedules. This information can then be used to provide pre-wetting event alerts or warning signals to a user or user assistant so that the user or assistant can take steps to avoid pad wetting events thereby reducing the number of pad replacements required and, more importantly, minimizing the number of times each day that a user is subjected to cleaning activities. Thus, for instance, if wetting data shows that a specific user voids within 60 minutes of consuming a drink, an alert may be generated after 45 minutes so the user or assistant has ample time to avoid a wetting event assuming the user's future wetting events follow a schedule similar to prior activities.

In at least some cases it is contemplated that the sensor system can be used in the establishment of a rolling/persistent "Incontinence Training Program". To this end, in some cases a patient's condition changes over time and therefore their voiding schedule may change as well based on rest, medications taken, medical procedures, dietary changes, liquid consumption changes, etc. In these cases, instead of simply learning a voiding schedule once and applying that schedule thereafter, the system may be programmed to automatically refigure a patient's voiding schedule on a rolling multiple day (e.g., 3 days, 7 days, etc.). Thus, when a patient first starts using pads, a processor may be programmed to track the patient's voiding schedule over a 3 day period to learn the patient's voiding schedule and may then set a pre-voiding alarm/signaling schedule to avoid pad soiling when possible. Here, when a pre-voiding alarm signal is generated, the patient or an assistant may take steps to avoid soiling of the pad. Then, after a fourth day of voiding data is detected, the voiding data from the most recent 3 days (e.g., second through fourth days of pad use) may be used to adjust the pre-voiding alarm signal schedule to account for any condition changes that affect the patient's voiding schedule. This rolling process of refiguring the patient's voiding schedule and adjusting the alarm schedule may continue over time so that pad soiling events can be avoided.

In still other cases, it is contemplated that some system processor may be programmed to obtain other patient condition data and use that other data in conjunction with the patient's voiding schedule to gain further insights into events that affect the patient's voiding schedule. For instance, is the patient's voiding schedule affected by when the patient consumes a medication, is the schedule affected by when the patient eats, sleeps, exercises, participates in physical therapy, etc. Here, the alert schedule can be adjusted automatically based on these other insights.

In addition to being important for avoiding pad soiling events which can be uncomfortable and embarrassing as well as disruptive of patient rest, the warning system that indicates when a patient should try to void in a rest room is also important in many cases for healing the patient's ailments. For instance, in cases where a patient already has bed sores or other skin ailments which are adversely affected by urine and other fluids, avoiding pad soiling events have a positive effect on the overall healing process. In cases where it can be shown that the training and warning system are useful in avoiding pad soiling events, may justify payments from insurance companies will pay for the sensor system as part of an overall healthcare payment program.

In some embodiments, at least a portion of sensor system electronics may be printed on each pad along with the anode and cathode traces. For instance, in at least some cases the sensing electronics will include a battery power source and a processor as well as a resistor where the resistor is located between the traces at one end of trace lengths and the processor applies a voltage at the other end of the trace lengths, detects the resistance between the traces and then compares the detected resistance to a known dry resistance and wet resistances to detect wetness. In some cases the resistor at the one end of the traces may be printed on the pad. In other cases, the resistor may be part of the sensor clip system.

At least some embodiments include a sensor pad assembly for detecting wetness, the pad assembly comprising a breathable polyethylene base layer, a first carbon black trace printed on a top surface of the base layer in a serpentine pattern, a second carbon black trace printed on the top surface of the base layer in a serpentine pattern that does not overlap the first trace, wherein at least a portion of the second trace is adjacent each portion of the first trace and an absorbing subassembly including non-woven layers that envelope a super absorbent polymer (SAP) material, the absorbing subassembly adhered to the top surface of the base layer over the first and second traces.

In some cases at least portions of each of the first and second traces are exposed at ends of the traces for connection to a sensing clip assembly. In some cases at least first ends of the first and second traces are adjacent an edge of the base layer for connection to a sensing clip. In some embodiments second portions of the first and second traces are adjacent an edge of the base layer for connection to a resistive clip. In some cases the base layer is substantially rectangular having at least a first edge wherein the first ends and the second ends of the first and second traces are adjacent the first edge.

In some embodiments the base layer is rectilinear having a width dimension and a length dimension and wherein the traces extend at least in part along the length dimension. In some cases the width dimension extends between first and second base layer edges, the first trace includes a series of substantially identical trace portions, each trace portion having a first end and a second end and first, second, third, and fourth subportions, the first subportion extending from the first end adjacent the first base layer edge to a location adjacent the second base layer edge, the third subportion spaced apart from the first subportion and extending from a location adjacent the second base layer edge to a location adjacent the first base layer edge, the second subportion extending between and connecting ends of the first and third subportions proximate the second base layer edge, and the fourth subportion extending between and connecting ends of the third subportion and a first subportion in an adjacent trace portion proximate the first base layer edge. In some cases the second trace includes subportions that extend along each of the first, second, third and fourth subportions of each of the first trace portions.

In some cases each of the first and third subportions are substantially straight and parallel and extend perpendicular to the length dimension of the base layer. In some embodiments each of the second and fourth subportions are substantially straight and extend along the length dimension of the base layer. In some cases, the pad is formed as a continuous pad structure extending along a structure length dimension wherein the assembly length is formed by detaching the pad assembly from the continuous pad structure.

Some embodiments further include an integrated resistor between second ends of the first and second traces. In some cases a portion of the first trace is adjacent each portion of the second trace. Some cases further include an upper tissue layer located between the SAP layer and an upper non-woven layer and a lower tissue layer located between the SAP layer and a lower non-woven layer.

Other embodiments includes a sensor pad assembly for detecting wetness, the pad assembly comprising a breathable polyethylene base layer, a lower non-woven layer and an upper non-woven layer, a first carbon black trace printed on the lower non-woven layer in a first trace pattern, a second carbon black trace printed on the lower non-woven layer in a second trace pattern that does not overlap the first trace pattern, wherein at least a portion of the second trace is adjacent each portion of the first trace, the lower non-woven layer adhered to the base layer and an absorbing subassembly including a super absorbent polymer (SAP) material enveloped between the upper non-woven layer and the lower non-woven layer.

Still other embodiments include a sensor pad assembly for detecting wetness, the sensor assembly comprising a breathable polyethylene base layer, a super absorbent polymer (SAP) material layer, a first non-woven layer located between the SAP material layer and the base layer, a first printed carbon black trace located between the SAP material layer and the base layer and forming a continuous first trace pattern and a second printed carbon black trace located between the SAP material layer and the base layer and forming a continuous second trace pattern, wherein at least a portion of the second trace is adjacent each portion of the first trace.

In some cases the first and second trace patterns are printed on the side of the base layer facing the first non-woven layer. In some cases the first and second trace patterns are printed on the first non-woven layer. In some embodiments the first and second patterns are serpentine patterns. In some embodiments at least a portion of the first trace is adjacent each portion of the second trace.

BRIEF DESCRIPTION OF THE SEVERAL VIEWS OF THE DRAWINGS

FIGS. 2a and 2b are a top plan view and an exploded edge view of a pad assembly that is consistent with at least some aspects of the present disclosure.

DETAILED DESCRIPTION OF THE DISCLOSURE

Figure 1:
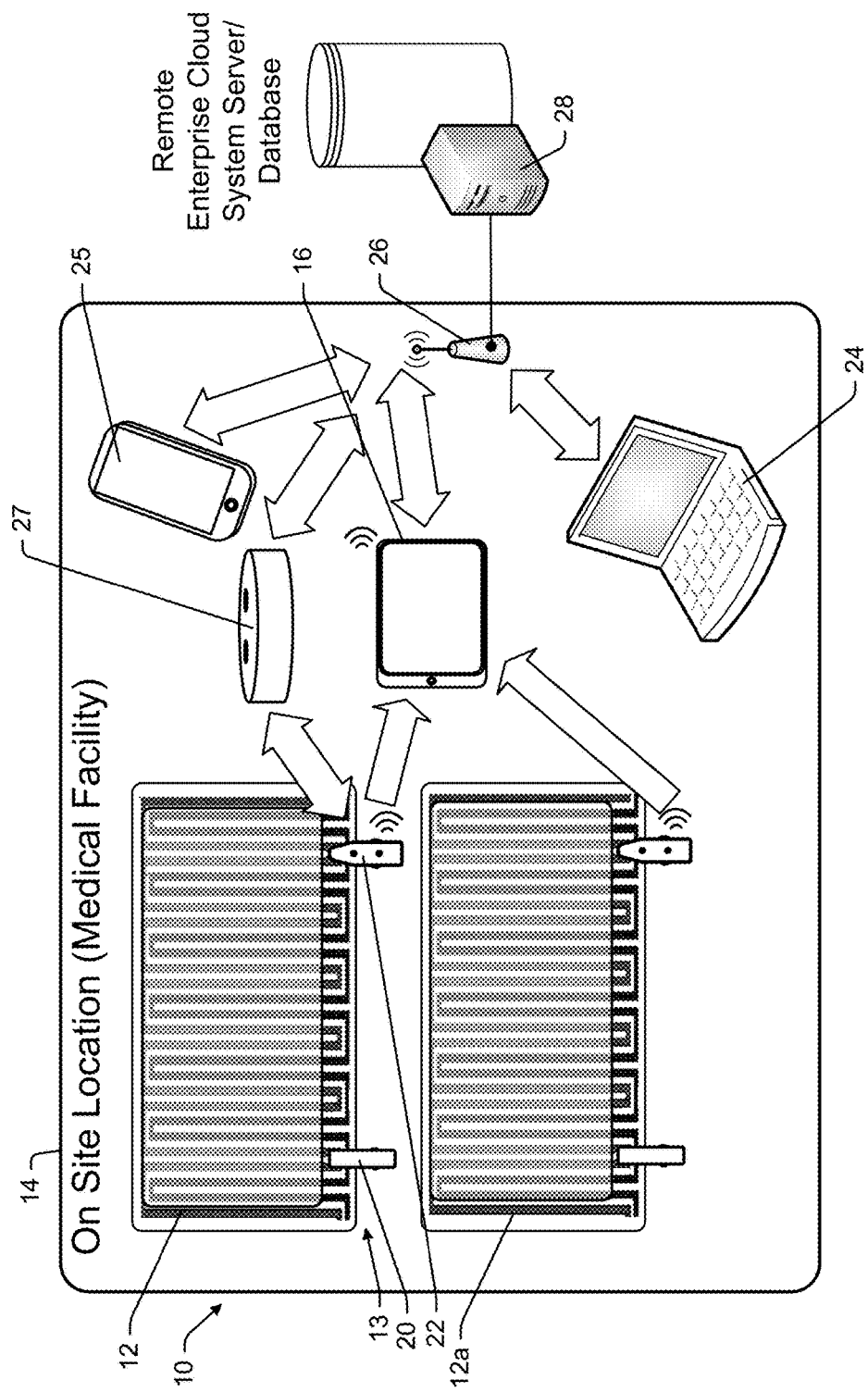
FIG. 1 is a schematic illustrated exemplary components of a sensing system that is consistent with at least some aspects of the present disclosure.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Hereafter there are different processors that cooperate to perform various functions. For instance, there is a sensor clip (see 22 in FIG. 1) that includes a processor, there are smart portable computing devices (see tablet 16 in FIG. 1), there are stationary smart computing devices (e.g., Alexa or other voice activated/interactive devices) and there are remote servers (see also 28 in FIG. 1) that each can perform various computing functions. Hereafter different processors are described as performing different steps in disclosed methods and systems. It should be appreciated that in other embodiments processes and steps may be performed by other system processors or combinations of processors.

Referring now to the drawings wherein like reference numerals correspond to similar elements throughout the several views and, more specifically, referring to FIG. 1, the present disclosure will be described in the context of an exemplary wetness sensor system 10 associated with a facility 14. While the system 10 may be used in many different types of facilities including hospitals, clinics, nursing homes, at user's homes, etc., unless indicated otherwise it will be assumed that facility 14 is a hospital, an exemplary user will be referred to as a patient, and an exemplary person charged with caring for the exemplary patient will be referred to as an assistant or a healthcare assistant. In addition, while the system 10 can be used with patient's whose midsections are supported by many different affordances, unless indicated otherwise it will be assumed that the exemplary patient is in a hospital bed and is substantially restricted to the bed for several weeks, unless indicated otherwise. For instance, in some cases sensor embodiments are described as used in diaper or cast operations and in those cases which are called out hereafter, a patient may not be restricted to a bed.

Sensor pads may take many different forms including rectangular sensor pads, strip shaped pads, pads that are shaped to mirror or at least conform somewhat to anatomical shapes of a human's body, etc. Herein, sensor pads of all types will be referred to as "sensor pad assemblies" or just "sensor pads" in the interest of simplifying this explanation.

Referring still to FIG. 1, system 10 includes a plurality of rectangular sensor pads 12, 12a (only two shown), sensor clip sets (one set labelled 20 and 22), an exemplary tablet type computing device (e.g., an iPad) 16, a wireless facility communication system represented by access point 26, a local user interface 24, and a remote system server and database represented collectively by numeral 28. In some cases a separate smart speaker type device 27 may be provided in a patient's room. Remote server 28 may be remote in the sense that it exists at a completely different location than facility 14 or it may simply be at a different location within facility 14 where a sensor pad is used. In some cases the server and database functionality are provided in a networked "cloud" arrangement as well known in the computing arts. In at least some cases a patient's portable computing device 25 (e.g., a smart phone, tablet, etc.) may also be integrated into the system for various purposes (e.g., receiving wetness warnings, examining wetness data and durations, setting user preferences related to pre-void alerts, etc.).

Each of the sensor pads 12, 12a, etc., and clip pairs 20, 22 are similarly constructed and operate in a similar fashion and therefore, in the interest of simplifying this explanation, only pad 12 and clip pair 20, 22 will be described here in detail unless indicated otherwise. In addition, unless indicated otherwise, a combination of a sensor pad assembly 12 and clip pair 20, 22 will be referred to hereinafter as a "sensor assembly" 13.

In operation, pad 12 is placed centrally along a length and a width dimension of a patient bed, preferably on top of a sheet or the like prior to the patient getting into the bed so that once the patient is in bed, the pad resides directly under the patient without sheets or other bedding materials between the patient and the pad. In at least some embodiments, the pad is arranged with the clip edge of the pad extending out from under the location of the patient to a lateral side (e.g., left side of the bed) or to the foot of the bed. Upon getting into the bed, the patient arranges their position so that their midsection is generally centrally located on pad or the pad is moved until so located with respect to the patient's preferred position in the bed. A sensor clip pair 20 and 22 is retrieved and the sensor clip 22 is programmed to be associate with a specific patient, facility bed or in some other way that enables data generated by the clip to be associated with a specific location or patient within the facility. Thus, for instance, the clip may be programmed to be associated with patient Mary Monday in bed 34 in room 2507 so that when a pad is wet, the system can report the wetness event on a patient or location basis and the assistant can quickly assess which pad has been soiled.

In other cases the server 28 may be programmed to know or have access to a facility schedule database that can be used to determine which patient is in which hospital room and may simply associate data generated by a clip in a specific room with a patient currently associated with the room.

The clips 20 and 22 are attached to the pad as described in greater detail hereafter. Sensor clip 22 detects wetness on the pad (and lack of wetness) and generates wetness data that either indicates the wet state of the pad or that is useable to discern the wet state of the pad. The clip 22 transmits the wetness data to a proximate portable device 16.

Device 16 can take many different forms including a smart phone, a portable tablet type computing device (e.g., and iPad), a laptop computer, etc. Here, in at least some cases the clip will transmit wirelessly via Bluetooth or the like to device 16. Device 16 is Bluetooth or otherwise wirelessly enabled and therefore can receive data transmitted by clip 22. Device 16 may be programmed to receive raw data from clip 22 that can be used by a device 16 processor to discern wetness state of a pad or may receive actual wetness warnings generated by a processor within clip 22. Device 16 stores premeasurement data for the pads which indicates where along the trace pattern length a wet spot occurs based on a measured resistance or electrolytic value. In at least some cases device 16 stores at least some of the received or processed data and can perform calculations and other data processes on that data over time to develop other information related to pad wetness including size of wet spot, rate at which a wet spot size increases, specific patient voiding schedules and void characteristics, etc.

When the data is stored, the device 16 may store the data with a time stamp indicating when the data was sensed via the clip 22 as well as other wetness event information. Device 16 is also equipped to transmit wirelessly (e.g., via 802.11b or newer versions, or other protocols) to an access point 26 to send either raw or conclusive data to server 28 for storage and processing or further processing. The device 16 may have a printer which can print reports that can be included in patient records.

In other embodiments device 16 may be replaced by a wireless relay device mounted to or proximate the patient's bed where the relay device includes a near field communication (NFC) antennae, a processor and a Bluetooth or other longer transmitting antennae. In this case, sensor clip 22 may transmit to the relay device using an NFC protocol and the relay device may relay the received data on to access point 26 or some other intermediate relay device so that the data is eventually provided to server 28 for processing and storage. Here, alerts or warnings may be provided to an assistant or a patient via one of devices 24 or 25 or in some other fashion.

Device 16 is also programmed, in at least some embodiments, to generate wetness state change warnings or notifications that are presented to the assistant so that the assistant can determine how to handle specific wetness situations. Here, for instance, if the system indicates that a small wet spot occurs on a pad, the assistant may use discretion and decide not to swap in a new pad given pad absorption capabilities and, subsequently when the patient voids a second time so that the wet spot or liquid volume increases substantially, the assistant may decide to discard the current pad and swap in a new pad. In other cases, the system may automatically track the patient's voiding schedule and provide reminders to the patient and/or the attending assistant prior to a likely event so that the patient or assistant can take steps to avoid a pad soiling event. Other warnings and notifications are contemplated.

Referring still to FIG. 1, in at least some cases it is contemplated that a smart speaker type device 27 may be provided in each patient's room where the speaker device 27, among other things, operates like a wireless router to receive raw wetness data from the sensor clip 22 and passes that data on to the system server 28. Speaker device 27 may also be programmed to perform various wetness and pad state calculations and to generate alert signals when pad state changes. Speaker device 27 may also transmit alert signals back to sensor clip 22 causing the clip to generate audible or visual alert indications as described hereafter.

In still other cases sensor device 22 may itself be programmed to perform at least a subset of system calculations to assess pad state changes and generate alerts as well as to transmit raw data as well as conclusions to via an access point or the like to server 28. In some cases sensor device 22 may have smart speaker capabilities built in as described in greater detail below.

Referring to FIGS. 2a and 2b, an exemplary sensor pad 12 that is consistent with at least some aspects of the present disclosure is illustrated in a plan view as well as an exploded edge view where different layers of the exemplary pad 12 are shown, respectively. While exemplary pad 12 is shown to include many layers in a specific arrangement, it should be appreciated that at least some of the layers may be provided in different arrangements or may be omitted in some arrangements with the pad still being consistent with at least some of the disclosure presented here. In some cases additional pad layers may be provided.

In some embodiments pad 12 is designed so that a user can link up sensor clips to either top or bottom edges of the pad 12 so that a user cannot place the pad on a bed or other supporting surface in a wrong orientation which can be frustrating. In these cases, the pad configuration along each of the top and bottom edges would be structurally similar with each of anode and cathode traces coming near opposite edges of the pad to be connected to a sensor clip 22 and a resistor clip 20 as described hereafter. In other cases, one edge of the pad may be designed for clip connection and the opposite edge may be covered with absorbent layers as described hereafter and shown in FIG. 2a. In the interest of simplifying this explanation only the connecting edge of a pad 12 that clips are applied to will be described in detail unless indicated otherwise.

In FIGS. 2a and 2b, pad 12 includes a bottom layer 48 that includes a breathable (=>2050 g/m2-24 hr.), 14-16 grams per square meter (GSM) polyethylene (PE) film; (0.46 mm thick) laminated (e.g., adhered) to a 26-30 GSM non-woven spunbond, polypropylene (PP) material. To form sheet 48, polypropylene pellets are melted and extruded into fine fibers which in turn are laid and bonded and then the breathable PE film is adhered, with 2 GSM glue, to the non-woven material to form a top surface. In at least some embodiments the top surface material is within a range of 35-grams per meter (GSM) and in particularly advantageous embodiments it is 43-48 GSM.

Referring still to FIGS. 2a and 2b, sheet material 48 comes in long rolls and has top and bottom edges (not labelled). In some embodiments a height dimension between top and bottom edges may be within a range between one foot and six feet, in some cases the range is between two feet and five feet and in still other embodiments the range is between three feet and four feet. A particularly advantageous height dimension of the sheet material between top and bottom edges is 30 inches but can be adjusted to different sizes.

A large printer device prints or otherwise applies a specifically formulated black carbon dispersion as traces to the top side/surface of sheet material 48 to form anode and cathode traces 40 and 42, respectively. In some embodiments the traces 40 and 42 may be applied to the PE or PP side of sheet 48. In some cases the PE side is printed on and the PP side forms the bottom surface to keep the pad in place on the surface bed, chair etc. In some cases the sheet is continuously printed as a roll of material 48 is unwound.

As shown, in at least some cases the anode and cathode traces are continuously printed on sheet 48 and then the sheet is cut from top to bottom edges to a sizes appropriate for intended use. In particularly advantageous systems, flexography is used to print the dispersion on sheet 48. Here, it should suffice to say that flexography is a form of printing which utilizes a flexible relief plate which operates essentially like a modern version of a letterpress that can be used for printing on almost any type of substrate.

The flexographic printing process is controlled in several ways to create an optimized trace pattern that has optimized sensing and robustness characteristics. To this end, during printing a viscosity controller is manipulated to maintain centipoise (e.g., liquid viscosity) at an operating point between 35 and 55 cP and, in particularly advantageous cases, at 40 cP. The temperature for drying during printing is maintained at a temperature within a range between 110 and 225 degrees F. and, in preferred cases, at around 10-15 degrees F. below the material damage temperature of sheet 48. The viscosity, press speed, anilox (80 LPI), plate, and substrate surface tension, anilox configuration (3-4 units), and impression pressure are also all controlled. The following are examples of the setting on the flexographic printer that have been shown to work well:

Drum Temp 86°
Chill Roll Temp 72°
Between color Temp 170°; Blower 85%
Turn Temp 165°; Blower 70%
Speed 125 to 200 ft/min
Tensions
  UNW 170
  Calan 18
  Nip 18
  Rew 14
  Blade— 2 Bars
  Ink pressure—2 extra points It is believed that each of the above operating characteristic values can be adjusted up or down by 10-15% with minimal effects on the ultimate characteristics of the pad assembly. In addition, in at least some cases, the printing process is repeated on each length of sheet 48 to increase the thickness of the combined traces applied until the traces can conduct sufficient current for sensing purposes. To this end, the printing system operates an automatic print design registration control to print multiple conductor layers of the same design until a required trace thickness is achieved.

In some embodiments the black carbon dispersion has a potential of hydrogen (pH) level greater than seven and less than ten with 0.5 to 5% surfactant and 0.5 to 5% drying solution. This mixture has been shown to result in high quality traces which conduct over distances required for most applications contemplated by this disclosure. This mixture and the sheet material 48 described above enable anode and cathode trace printing without substantial penetration of the black carbon dispersion into the top surface of sheet 48 which is required for sensing purposes.

One particularly useful carbon black solution for printing the traces is sold using the tradename Unibond 2951 which is manufactured by Unichem, Inc. of Haw River, North Carolina. The specific Unibond 2951 dispersion used for printing the traces has 27-31% solids, a pH of between 8.7 and 9.7, a density of 8.5+lbs./gal. and a viscosity of 30-50 cPs. The drying and curing temperature of the Unibond 2951 is within a range between 150-190 degrees F. in some cases and the curing temperature is within the range between 240-360 degrees F. with a viscosity of 12,000-14,000 for producing traces that can last in storage for 10-15 years, but is limited by the melt temperature of the substrate that the dispersion is applied to. In particularly advantageous embodiments the curing temperature is within 10% of the melt temperature of the sheet material 48.

Referring again to FIGS. 2a and 2b, printed anode trace 40 forms a serpentine pattern that winds back and forth along parallel lines between top and bottom ends or portions of sheet 48. In some cases the end portions of the pattern are within ¾ to two inches of top and bottom edges of sheet 48 to enable clip connections at those edges without crinkling edges of the pad 12 in use as described hereafter. In particularly advantageous embodiments trace portions closest to the edges are about 1 and ¼ inch from each edge. In some cases, the traces are only spaced from one edge (e.g., top or bottom) and may be much closer (e.g., 0.75 inches) to the other edge (e.g., top or bottom).

Cathode trace 42 also forms a serpentine pattern that winds back and forth along parallel lines between top and bottom ends of sheet 48 where the cathode pattern is interleaves with the anode pattern. Thus, as shown, each "vertical" run of the anode trace 40 runs parallel to one vertical trace of the cathode and each vertical cathode trace runs parallel to one vertical anode trace. Each trace 40 and 42 has a uniform thickness dimension and a uniform width dimension in the illustrated embodiment that is between 5 and 20 millimeters and the space between adjacent anode and cathode trace sections is also between 5 and 20 millimeters and is uniform in the illustrated embodiment. In particularly advantageous embodiments the uniform trace width is between 5 and 15 millimeters and the spaces therebetween have a similar uniform spacing. In other cases the anode and cathode traces may have different thickness and width dimensions or different parts of adjacent traces may be separated by varying open, non-printed spaces on the face of sheet 48. The diameter of the printing roller is a controlling factor of the image length, the traces 40 and 42 need to be adjusted to be a width with the open non-printed spaces that allows repeatability and covers the entire circumference of the printing roller.

In at least some embodiments the specific black carbon dispersion material is applied so that 1 to 8 grams of the coating material is per square meter of printed trace. In particularly advantageous embodiments the material is applied so that the range of grams per square meter applied is between 2 and 5 grams. With applications within these ranges, tests have shown that sufficient trace conduction occurs for sensing purposes and, when applied material is less than in these ranges, failure rate increases appreciably.

In at least some cases the amount of dispersion material applied per unit area of each trace is substantially uniform throughout the traces. In other cases, different amounts of dispersion material is applied so that different sections of the traces having the same length dimension have different resistance levels. In other cases the conductivity of the dispersion material applied to different sections of a trace may have different resistive values so that different sections of the traces have different resistance values per unit length.

In some embodiments the resistance value per unit length of each trace is known and therefore can be used in calculations to determine where along the trace lengths a wet spot occurs. The idea here is that when a wet spot occurs between adjacent portions of the cathode and the anode traces, a short occurs at that location which can be detected by the sensor clip 22. The clip measures the resistance detected and can use that measurement along with the known resistance value per unit trace length to assess where the short occurred.

Referring to FIGS. 2a and 2b, upper and lower tissue layers 54 and 50 envelope a pulp and super absorbent polymer (SAP) layer 52 (hereafter "the SAP layer") to form an absorbing subassembly. In at least some cases, as well known in the liquid absorbing arts, the SAP material includes small gel beads that have all water removed. When liquid is introduced, the beads suck up the liquid and grow into gel beads that retain the liquid. The two tissue layers 50 and 54 and SAP 52 are embossed or quilted together so that the SAP material is held in place and embossing lines are provided for directing liquid to preferred areas of the pad assembly upon a voiding event. The SAP layer is made up of Pulp (Fluff)/Tissue which is 106.56 GSM and the SAP is 14.35 GSM. The embossed tissue and SAP absorbing subassembly is adhered to the top surface of the material 48 and applied traces so that at least one edge of the traces is exposed (see FIG. 2a) for connecting clip devices. For instance, 2-3 inches of an edge of the traces 40 and 42 may be exposed for clip connection. Here, the adhesive 60 is applied to the top surface of layer 48 to cover the area on which the quilted subassembly is laid and then the quilted subassembly is applied to the adhesive. A second layer of adhesive 62 is applied over the quilted pad subassembly and a non-woven cover layer. In some embodiments a non-woven cover layer 14 GSM Super Soft CD-Rod, hydrophilic 56 of liquid permeable material is placed over the upper tissue and adhered in place.

In at least some cases alignment indicia may be printed on a top surface of the pad indicating a location at which the sensor clip pair devices are to be mounted in order to make proper connections to traces on the pad. To this end, see exemplary indicia at 17 and 19 on pad 12 in FIG. 2a which have shapes that are akin to the shapes of portions of the clips 20 and 22 that are to be mounted to the pad.

Figure 2C:
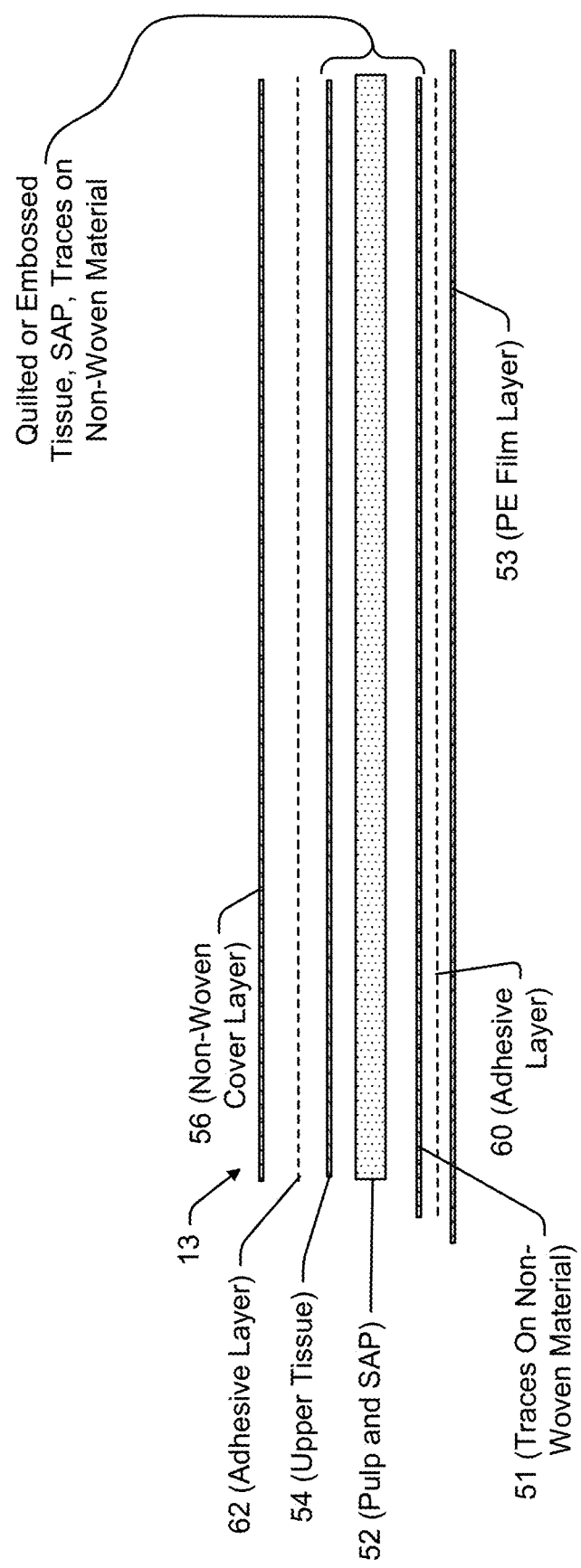
FIG. 2c is similar to FIG. 2b, albeit showing a different embodiment of the pad assembly.

FIG. 2c shows an exploded edge view of a second pad arrangement 13 that is consistent with at least some aspects of the present disclosure. Pad 13 includes a bottom PE film layer 53 and a separate non-woven layer 51. Here, the carbon black traces are printed on layer 51, not the PE film 53. An absorbing subassembly including printed non-woven layer 51, SAP layer 52 and a upper tissue layer 54 are quilted or otherwise embossed together. Adhesive layer 60 in the shape and having the area of the absorbing subassembly is applied to PE film 53 and the quilted subassembly is placed on layer 60. Second adhesive layer 62 is applied over the top surface of the quilted subassembly and top non-woven layer 56 is adhered. Here, different printing properties of the non-woven layer 51 may result in better absorption of the dispersion material and therefore better overall performance of the sensing arrangement.

Figure 3:
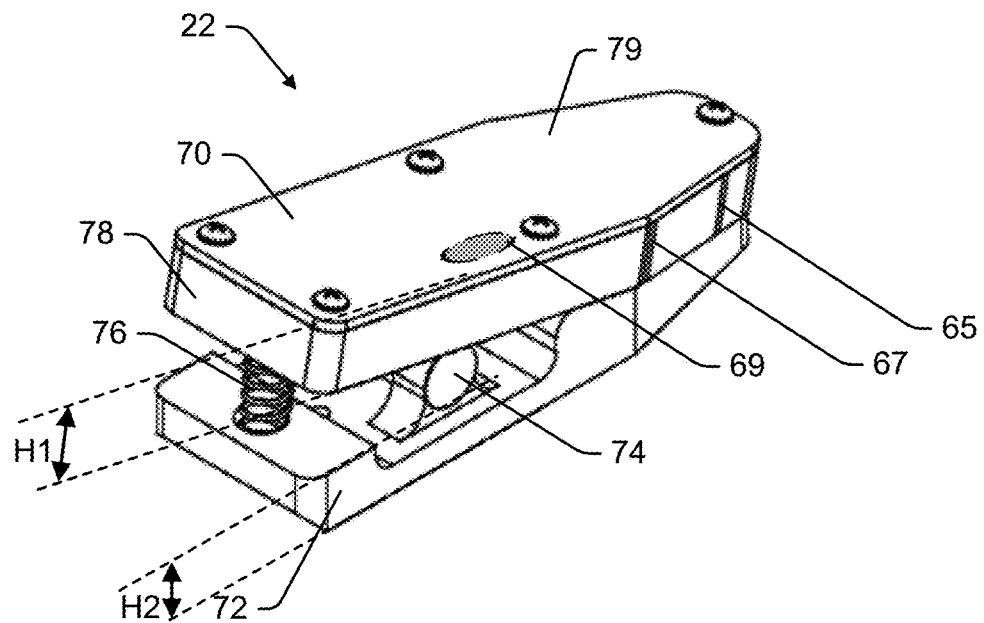
FIG. 3 is a perspective view of a sensing clip assembly that is consistent with at least some aspects of the present disclosure.

Referring again to FIG. 1 the exemplary sensor clip pair 20, 22 includes a resistor clip 20 and a sensor clip 22 that clip on to an edge of a pad 12 as shown in FIG. 1 and other figures in the disclosure described hereafter. Referring also to FIG. 3, sensor clip 22 includes an electronics housing 70, a jaw member 72, and a spring 76. Housing 70 includes a cavity forming member 78 and a cover 79 that, in the illustrated embodiment, screws onto member 78 to close off an open side of the cavity formed therein. The housing components are formed of plastic in at least some embodiments and will have a hermetic seal between the cover and the lip on the housing around the cavity so no liquid can penetrate into the cavity.

Cover 79, in at least some embodiments, is at least somewhat translucent so that an assistant can see through the cover to observe the state of one or more LED light signaling devices located within the housing cavity. In FIG. 3, an exemplary dual color LED is illustrated at 69 in phantom indicating a location on cover 79 under which the LED resides. Here, for instance, LED 69 may be illuminated either green or red indicating different states. In other cases, the LED 69 may be controlled to be constantly on, to blink on and off, etc., to indicate different states. In some other cases LED brightness may be controlled to indicate different states.

Figure 4:
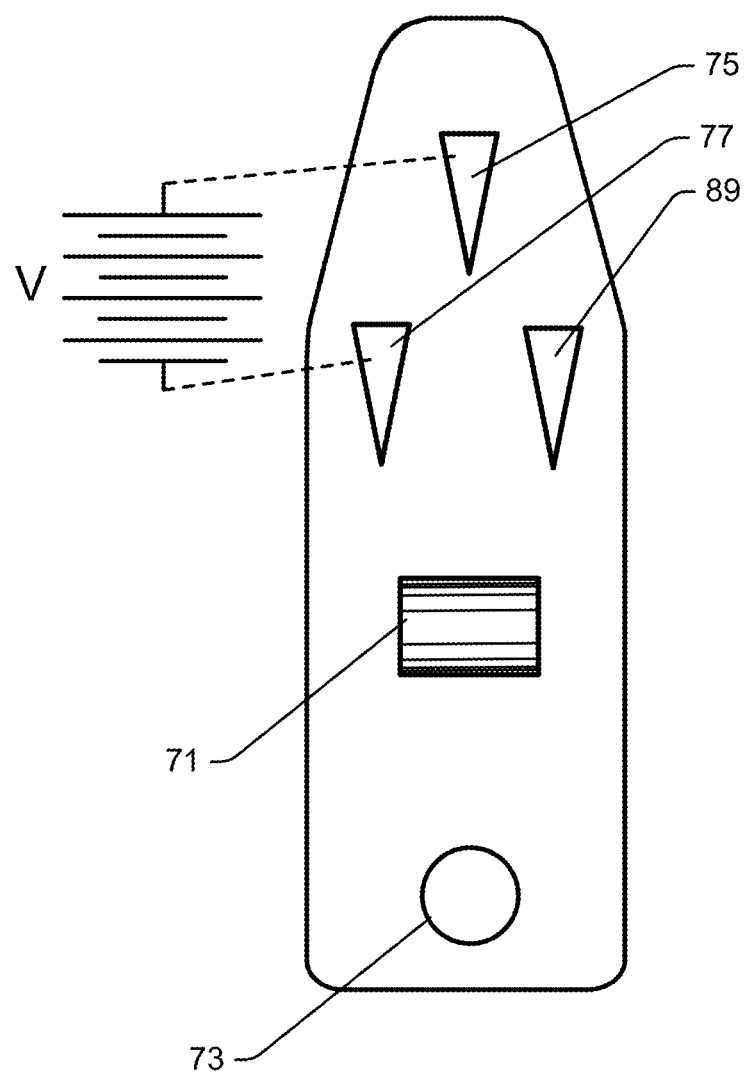
FIG. 4 is a schematic view showing an exemplary electrical connection prong arrangement of the clip shown in FIG. 3.

The housing member 78 includes features on a surface opposite cover 79 that cooperate with features on jaw member 72 to form a hinge 74 with spring 76 located between distal facing surfaces of housing 70 and member 72. Spring 76 causes the jaw member 72 end opposite the spring to clamp closed as shown in FIG. 3 unless force is applied to distal ends of housing member 78 and jaw member 72. Referring also to FIG. 4, a bottom surface of housing 70 prior to assembly with jaw member 72 is shown where several features can be seen including a hinge forming cylindrical feature 71, a spring receiving circular opening 73, and three electrical connection prongs 75, 77 and 89 that extend out of the housing cavity for piercing through an edge portion of the pad 12 to make electrical connection to the pad traces as described in more detail hereafter. As shown, a voltage can be applied between prongs 75, 77 and 89 via a battery (e.g., 3 volt) located within housing 70. Indicia 67 and 65 are located on the lateral sides of housing 70 that can be used to align probes 75 and 77/89 with portions of traces 40 and 42 respectfully, when connecting the clip 22 to a pad. To this end, an assistant can observe alignment of the indicia with the traces to increase the chances of making a good sensing connection between the probes and the traces. In some cases the indicia will simply include painted lines. In other cases, the indicia will include channels formed in the external surface of the housing 70. In some cases the indicia is only provided on the housing 70 and not the jaw 72 (see FIG. 3). In other cases the indicia may be provided on both the housing and the jaw. To this end, see the alternative clip assembly embodiment 500 shown in FIG. 19 and described in more detail below where recessed indicia 512 and 514 is provided on both the jaw and the housing.

Referring yet again to FIG. 3, the housing 70 has a height dimension H1 and jaw 72 has a height dimension H2. In at least some cases the height dimension H2 is minimized and is only as large as required to structurally provide a robust jaw structure. Thus, for instance, in at least some cases height H2 will be within a range between one sixteenth inch and one half inch. In other embodiments height H2 will be between one eight inch and one quarter inch. One way to minimize height H2 is to place all electronics and other functional components within housing 70 as opposed to within the structure that forms the jaw 72. By making height H2 small, most of the clip assembly structure can be located on one side of a sensor pad assembly which is advantageous in at least some applications.

Figure 5:
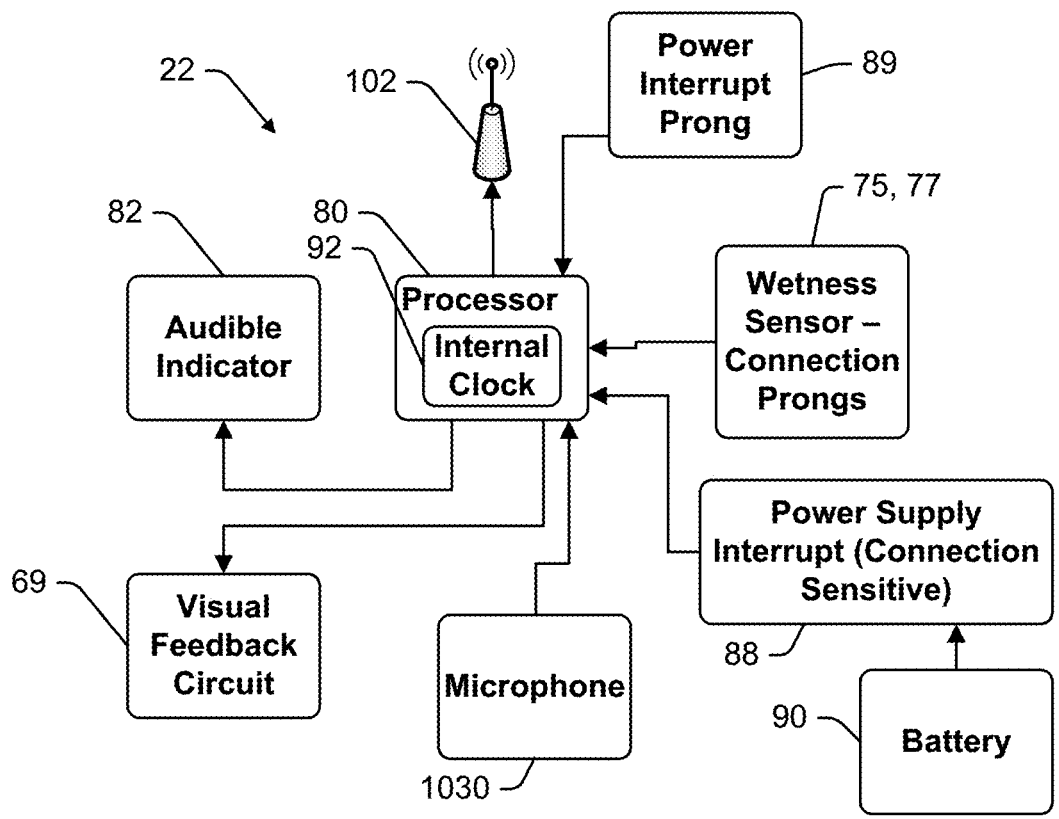
FIG. 5 is a schematic illustrating electronic components that are included in at least one clip type like the one illustrated in FIG. 3.

Referring now to FIG. 5, sensor clip 22 includes electronic components located within the housing cavity including a processor 80 having an internal clock 92, an audible indicator 82, a visual indicator 69, the wetness sensor prongs 75, 77 a power supply interrupt 88 and power supply interrupt prong 89, a battery 90 and a transceiver 102 (e.g., transmitter and receiver). Processor 80 is linked to prongs 75, 77 and 89 and can detect various events by applying a voltage across the prongs and detecting impedance or resistance therebetween. For instance, processor 80 can detect when clip 22 is and is not properly connected to traces in a pad 12. As another instance, once clip 22 is properly connected to pad traces, processor 80 can detect wetness on the pad 12 and, in some cases, location of wetness on the pad 12.

Referring still to FIG. 5, processor 80 is linked to battery 90 via a power supply interrupt 88. Power supply interrupt 88 opens and closes the link between processor 80 and battery 90 based on whether or not the prongs 75, 77 and 89 are properly connected to pad traces to ensure that battery power is conserved. Here, unless the clip is secured to a pad in use, the power supply interrupt disconnects the battery from other system circuitry.

In some cases battery 90 is designed to store sufficient energy for powering the clip 22 for up to 6 months of normal use given the power supply interrupt function of component 88. In other cases the battery 90 is designed for 3 months of normal use. In at least some cases, sensor clip 22 is intended to be used multiple times (e.g., hundreds of times in some cases) with a single patient and then discarded to avoid problems with bodily contamination and a general sense of uncleanliness when medical equipment is reused. In other cases, battery 90 may be replaceable so that other clip 22 components can be reused with different patients. In some cases it is contemplated that the electronics from clip 22 may be sterilized, removed and placed within a new housing 70 for use with additional patients where the housing operates to seal off the electronics from biological contamination. In other cases the battery 90 may be wirelessly recharged.

Referring to FIGS. 1 and 5, processor 80 is linked to transceiver 102 to transmit data or information to proximate portable computing devices 16 and, in some cases, to receive information or control signals back from devices 16 or from other system processors. In some cases, processor 80 may also transmit signals to a patient's computing device 25, a Nurse Call System devices 24 or directly to an access point 26 within vicinity of the patient's location in the facility. In at least some cases processor 80 transmits (and in some cases also receives) signals via Bluetooth technology. In other cases, processor 80 may transmit (and receive) using other wireless protocols and equipment (e.g., 802.11b and above, cellular, LoRa, ANT, RF, NFC in a case where there is an NFC receiver proximate the patient's location, etc.). In some cases Bluetooth is preferred as it has less interference issues with other devices that are often prevalent in hospital and other medical facilities (e.g., pace makers and other devices).

Referring still to FIG. 5, processor 80 is also linked to audible indicator 82 and can be used to provide audible signals to the patient or assistant. For instance, indicator 82 may include a simple beeper or buzzer or, in some cases, may include a small speaker device for generating simple sounds or even a voice messaging signal. As an example of an audible signal, in at least some embodiments it is contemplated that when clip 22 is properly connected to pad traces, processor will generate a simple beep to confirm proper connection and may generate a second distinctly different sound when improper connection occurs. In other cases, processor 80 may generate a voice signal indicating "Connection successful" or "Improper connection, try again", based on connection state. As another example, when a pad reaches some level of saturation (e.g., is approaching a maximum absorbing capacity), processor 80 may generate an audible beep or voice signal indicating saturation level.

Referring to FIG. 5, processor 80 is linked to visual feedback circuit 69 to provide clip and pad status signals visually. For instance, as in the case of the audible indicator described above, processor 80 may provide a visual indication when clip 22 is properly attached to pad traces and a different indication when a pad reaches some specific saturation or wetness level. Here, the visual indication may take the form of illuminating different LEDs different colors or illuminating a multi-color LED different colors to indicate different detected states. In some embodiments different color LED's are placed in different locations within clip 22. This provides the assistant, who may be color blind, the ability to detect different indicated states based on locations of illuminated LEDs. For instance, see again the description of LED 69 operation above.

In at least some cases it is contemplated that signaling may also be provided via a patient's computing device 25 and/or an assistant's portable computing device 16. Here, for instance, upon successful connection of clip pair 20, 22 to a pad 12, sensor clip 22 may transmit a signal to assistant's device 16 indicating success and an application program running on device 16 may provide a visual signal or audible signal indicating successful connection. Similar connection success messages may be provided via patient phone 25 to provide direct reassurance to the patient that the wetness sensing system is operating properly.

Referring still to FIG. 4, in at least some cases sensor clip 22 will include a microphone for receiving voice signals from a patient or an assistant and processor 80 may be programmed to perform a small set of functions based on received voice signals. For instance, a query like "Is my pad sensor working?" may be received and processor may respond with a voice message "Your sensor is working properly". Here, the idea is that a patient need not fumble around looking for the sensor clip 22 to try to check operation. Other voice based functions may enable a patient/assistant to verbally query about pad state (e.g., damp, wet, soaked, etc.) recent wet state changes (e.g., when did this pad first sense wetness), when is my next void alert scheduled to occur, etc. In still other cases processor 80 may be programmed to pass on voice queries to server 28 for processing and may receive voice responses back for broadcast to a patient or assistant.

Figure 6:
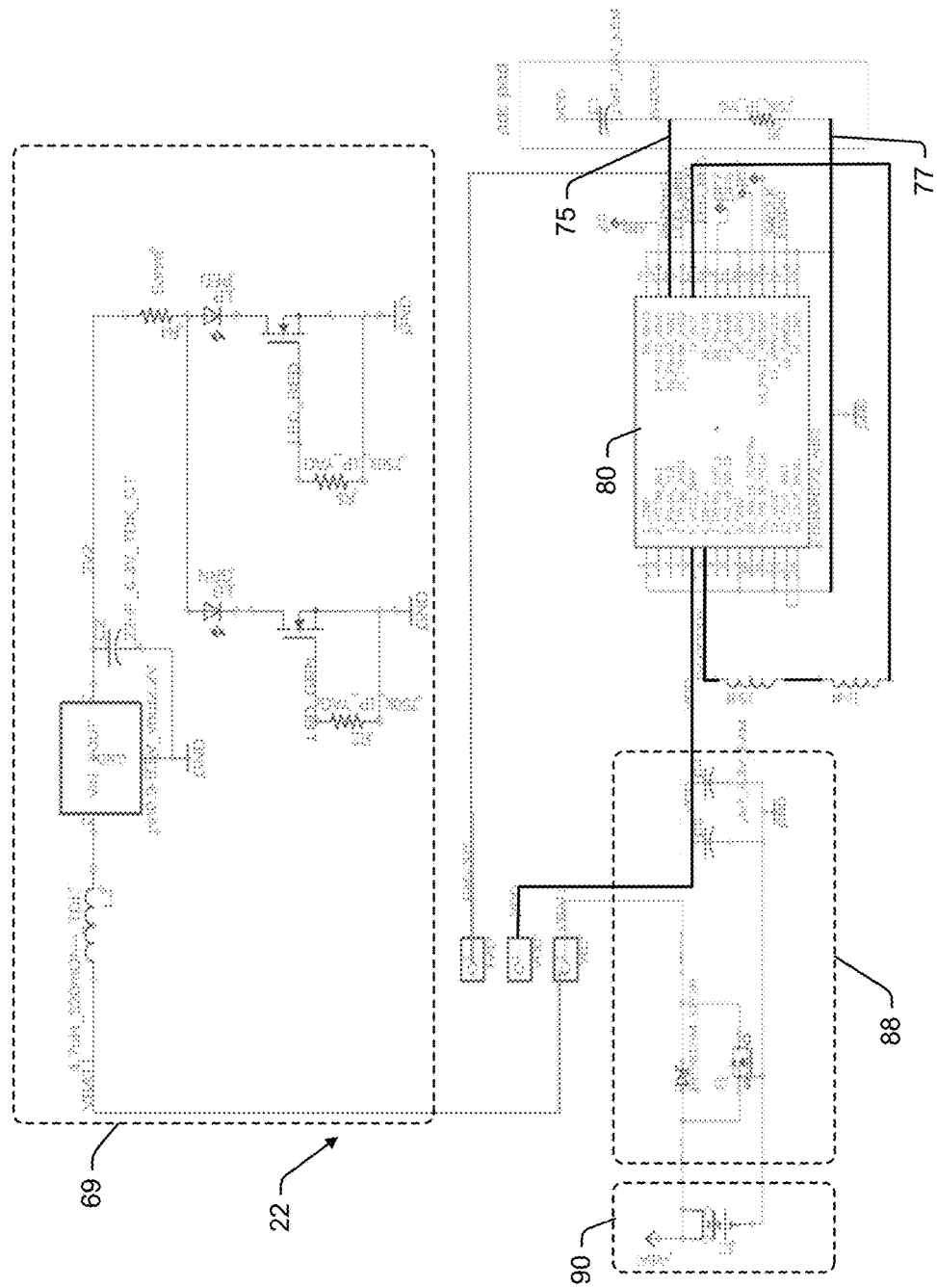
FIG. 6 shows exemplary electronics that form at least some of the components shown in FIG. 5.

Referring now to FIG. 6, a circuit diagram showing exemplary components that comprise the processor 80, power supply interrupt 88, battery 90, and visual feedback circuit 69 from FIG. 5 are shown in some detail. Battery 90 provides power to power supply interrupt 88 which controls the battery link to processor 80 to make sure that the battery is not discharging when a proper trace connection is not made. Power supply interrupt 88 includes short sections of the disposable product anode and cathode conductors traces. The trace in the power path opens the battery circuit when not in use, maximizing battery shelf life while enabling user feedback regarding the status of the connection with a disposable pad 12. Power supply Interrupt circuit 88 may be further include a transistor to prevent voltage drop across pad trace sections in at least some embodiments.

Referring again to FIG. 6, processor 80 is linked to the clip probes 75 and 77. Processor 80 is also linked to visual output circuit 69 which includes a configuration for controlling LED brightness and color. Circuit 69 includes a boost converter to ensure that LED brightness remains constant regardless of battery output voltage.

Figure 7:
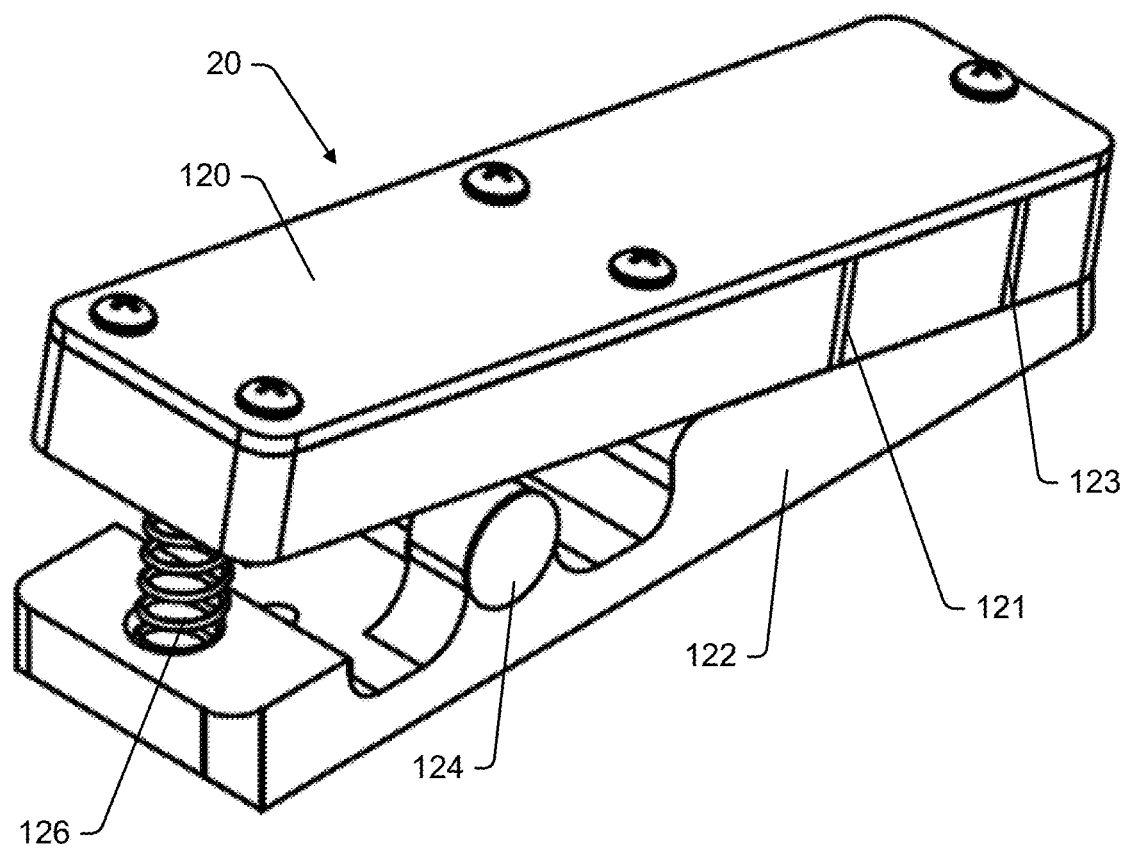
FIG. 7 is a perspective view of a resistor clip assembly that is consistent with at least some aspects of the present disclosure.
Figure 8:
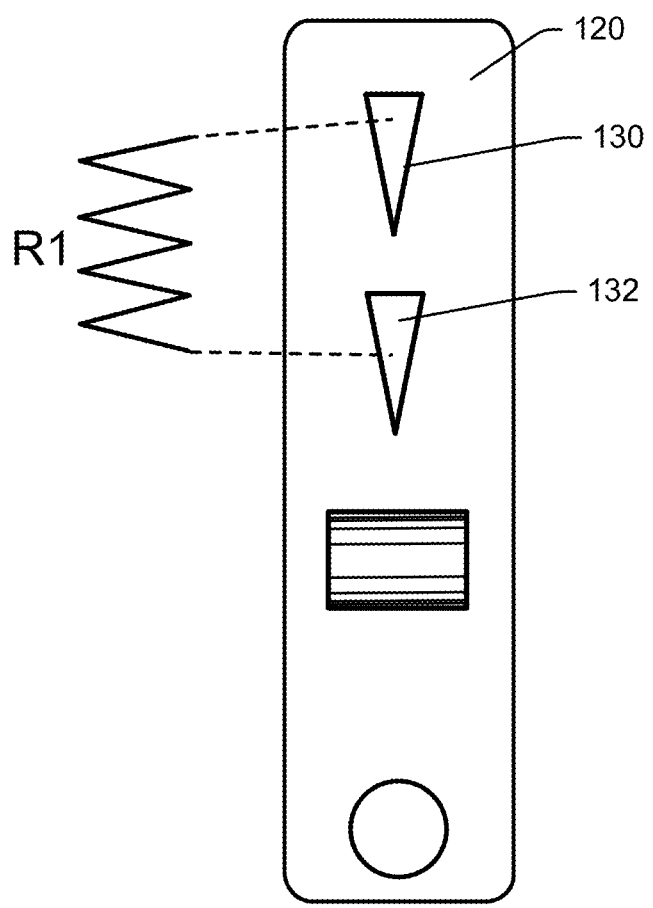
FIG. 8 is a schematic view showing an exemplary electrical connection prong arrangement of the clip shown in FIG. 7.

Referring now to FIGS. 7 and 8, an exemplary resistance or resistor clip 20 is illustrated. Clip 20 is similar to sensor clip 22 in that it includes a housing 120 that forms a cavity (not illustrated), a jaw member 122 and a spring 126 where member 122 and housing 120 are connected via a hinge 124 and are biased via spring 126 into a closed state as shown in FIG. 7. Probes 130 and 132 can be seen in FIG. 8 that extend out the surface of housing 120 facing the distal end of jaw member 122. A resistor R1 located in the housing cavity is connected between probes 130 and 132. Indicia 121 and 123 are located on the lateral sides of housing 120 that can be used to align probes 130 and 132 with portions of traces 40 and 42 when connecting the clip 20 to a pad 12. The resistive value of the clip resistance is within a range of 1 to 15 Mohms and in particularly advantageous embodiments will be within a range between 6 and 12 Mohms.

Referring again to FIG. 6, the sensor system includes a voltage divider with a fixed resistance R1 that represents the clip 22 resistance on the lower side. The disposable product includes the high side of the voltage divider allowing the Analog-Digital Converter (ADC) to measure a "negative resistance" across the pad. A correctly connected dry disposable product registers as resistance with a predictable value measured in series with R1. Capacitor C1 provides stabilization, preventing spurious readings. As electrolytic fluid enters the disposable product, the resistance decreases, resulting in a higher voltage at PADOUT. The degree of saturation can thus be determined from the value returned by the pad. An over-saturated pad results in an "Electrolytic Effect," causing the disposable product to generate a small voltage measurable with this resistor configuration.

Figure 9:
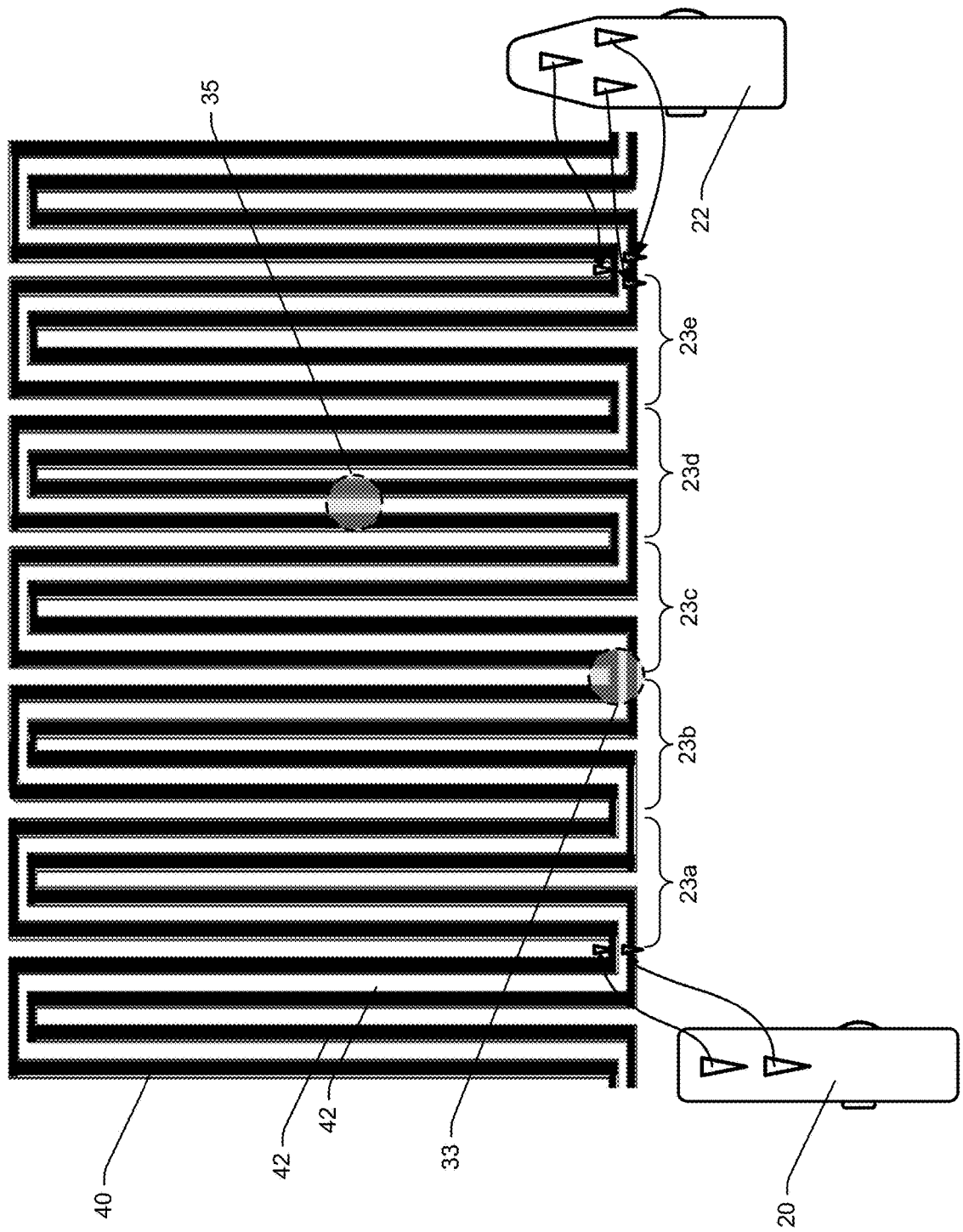
FIG. 9 is a schematic view of a clip pair and a pad trace pattern showing how clip prongs connect to the trace pattern to create a sensing circuit.

Referring now to FIG. 9, exemplary sensor and resistor clips are shown at 22 and 20, respectively. To install clip 20 on the edge of a pad 12, the jaw end of the clip is opened and the pad edge is slipped therebetween. Indicia 121 and 123 on the lateral sides of the clip 20 (see again FIG. 7) are aligned with the visible traces 40 and 42 on the pad 12 to align the probes 130 and 132 with the traces and the clip is released so that the spring force causes the probes to penetrate the pad traces and make electrical contact therewith. Similarly, to install clip 22 on the edge of a pad 12, the jaw end of the clip is opened and the pad edge is slipped therebetween. Indicia 65 and 67 on the lateral sides of the clip 22 (see again FIG. 3) are aligned with the visible traces 40 and 42 on the pad 12 to align the probes 75 and 77, 89 (see again FIG. 4) with the traces and the clip is released so that the spring force causes the probes to penetrate the pad traces and make electrical contact therewith.

Figure 10:
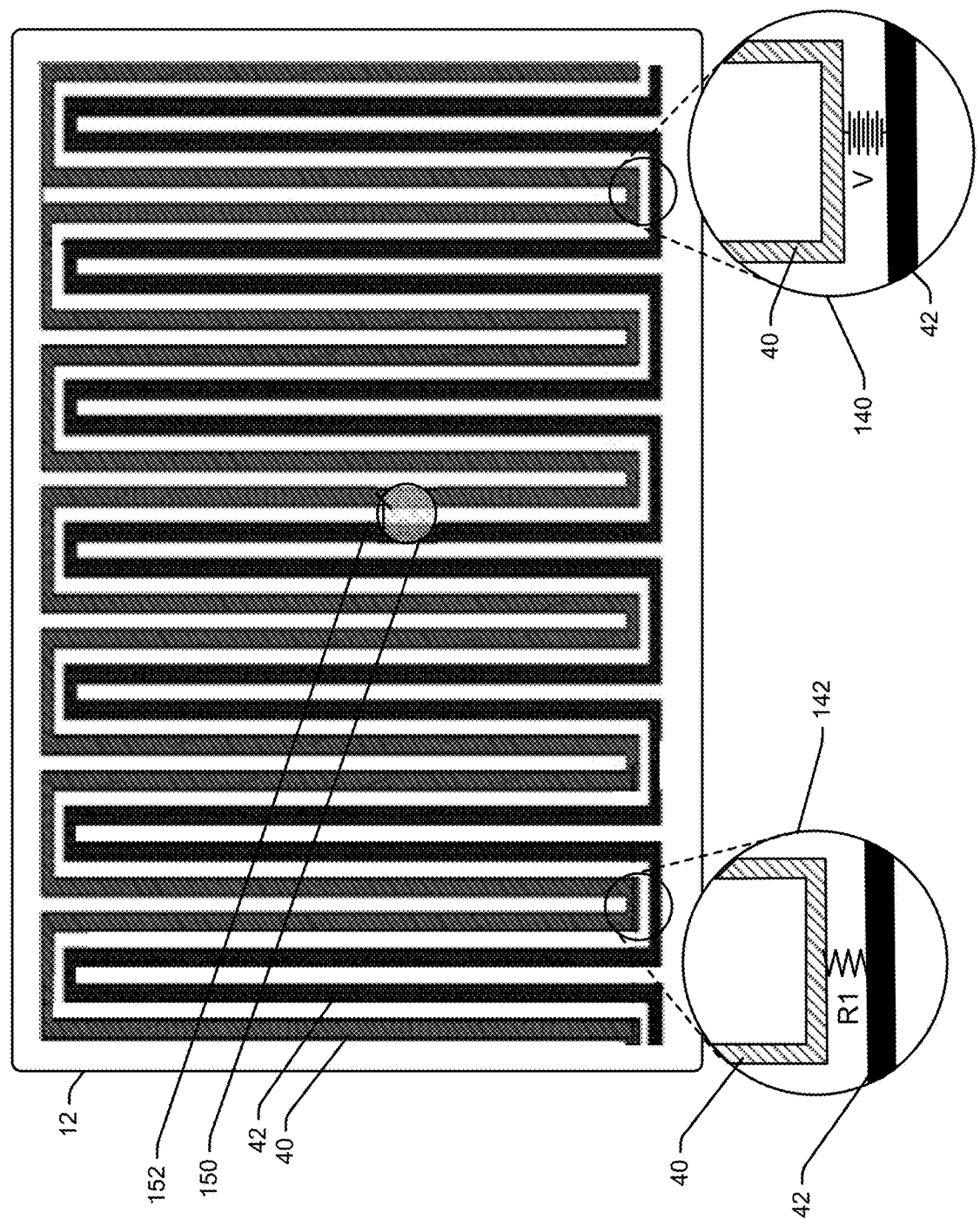
FIG. 10 shows the sensing circuit that results when the clip pair of FIG. 9 are connected to a pad with a small wet spot on the pad.

Referring to FIG. 10, once clips 20 and 22 are installed on the edge of a pad 12, the sensor clip processor 80 connects a DC voltage across the traces 40 and 42 as illustrated at 140 and the resistor clip 22 provides resistance R1 between traces 40 and 42 as shown at 142 during an initial connection testing phase of clip operation. Once the initial voltage is applied across the traces, processor 80 detects the impedance of the resistor R1 combined with the traces and compares that value to one or more known and expected values. In at least some embodiments, if the detected impedance is within an expected range of one of the known values, processor 80 illuminates the LED 69 (see FIG. 3) green and if it is not within an expected range (e.g., the clips are not properly aligned with and connected to the traces 40 and 42 for some reason), illuminates the LED 69 red to indicate improper connection. In another scenario, if the sensor clip 22 malfunctions for some reason and simply does not work, the processor will not illuminate LED 69 and in that case the assistant will know that the clip is not working and can retrieve a different sensor clip to use with the patient.

Regarding the expected "ranges", referring again to FIG. 9, the impedance detected when a clip pair is connected to a pad as illustrated is related to the length of the serpentine traces between the sensor and resistor clip pair. In FIG. 9, the number of trace switchbacks between sensor clip 22 and resistor clip 20 is five as labelled 23a through 23e and the initial impedance detected when the pad is dry is based on the trace lengths associated with five switchbacks. In other cases when a clip pair is attached to a pad like the FIG. 9 pad, relative locations of the clips may be different so that more or fewer switchbacks occur between the clip pair. For instance, in another case it may be that resistor clip is attached to the pad as indicate at 33 so that only three switchbacks 23c through 23e occur between the clip pair. In this case, the initial impedance detected when the pad is dry would be based on the trace lengths associated with three switchbacks, not five.

In at least some cases the clip is programmed to use an initial impedance reading to determine trace lengths between the clip pair and the processor then compares the initial impedance with impedance ranges associated with one, two, three, four, five, etc., switchback lengths between the clip pair. If the initial impedance measurement is in one of the expected ranges, the processor determines that the clips are properly connected and functioning properly. In addition, based on which range the initial reading is in, the processor determines the length of the pad between the clip pair. For instance, the processor determines if there are 2, 3, 4, 5, etc. trace switchbacks between the clip pair. The length of pad is important in at least some cases where the processor generates alert signals when wetness is near an edge of the pad and may run off the pad. In this regard, if wetness is detected two switchbacks away from the sensor clip at the location 35 indicated in FIG. 9, how close that wet spot 35 is to the pad edge will be a function of pad length. Here, if the pad length between the clip pair is only two switchbacks long, the wet spot 35 would be fairly close to a pad edge and be more of an issue than if the pad length between the clip pair were five switchbacks long. Once trace/pad length between the clip pair is known, the processor (or other system processor) may base at least some system operations on the known length.

In other cases pad lengths may be precut and instructions provided for specific locations at which clips should be attached to the pad edge so that the trace/pad length is known and there is no need to adjust system operation based on trace/pad length between the clip pair. For instance, see again indicia 17 and 19 in FIG. 2a indicating where a clip pair should be attached to the illustrated pad 12. In FIG. 2a the indicia correspond to a pad/trace length between clips that is five switchbacks long and therefore the clip processor would be programmed to confirm proper connection when an initially sensed impedance matches a five switchback length and to perform at least some operations assuming the five switchback length.

After the clips are properly installed, processor 80 starts a wetness sensing process wherein the processor 80 periodically (e.g., every second to 180 seconds, depending on how the clip processor is programmed) applies a DC voltage across the traces 40 and 42 and detects impedance or resistance of the traces, resistor R1 and any wet spots that appear on the pad between trace sections. Where the pad is dry, the pad circuit is through the traces 40 and 42 as well as the resistor R1 and the impedance remains generally at the initially impedance that was detected at the time of initial clip connection. If the pad is wet between adjacent portions of the traces 40 and 42, at least a partial short occurs at the point of wetness and therefore the measured impedance or resistance changes and that change is indicative of a wet pad. In this regard, see in FIG. 10 that if a wet spot 150 exists on the pad 12 as illustrated, a short occurs at 152 so that processor 80 detects a change in pad impedance and therefore detects a soiled pad.

Referring still to FIG. 10, in addition to determining that the pad is wet, processor 80 can use the change in impedance to determine the location on the pad at which short 152 occurs and therefore at least the general location of the wet spot 150. To this end, the traces generally have uniform resistance per unit length and therefore, a simple calculation can determine where along the length of each trace a short occurs. The trace length to short distance can be mapped to the trace patterns on the pad and therefore be used to determine the wet spot location. In other embodiments where raw data is sent from processor 80 to device 16, the device 16 processor may use the raw data to calculate various states and conditions such as dry, damp, wet, wetter, extremely wet, the location of a wet spot, etc. In still other embodiments device 16 may send the raw data to server 28 and server 29 may calculate wet state and location on the pad.

Figure 11:
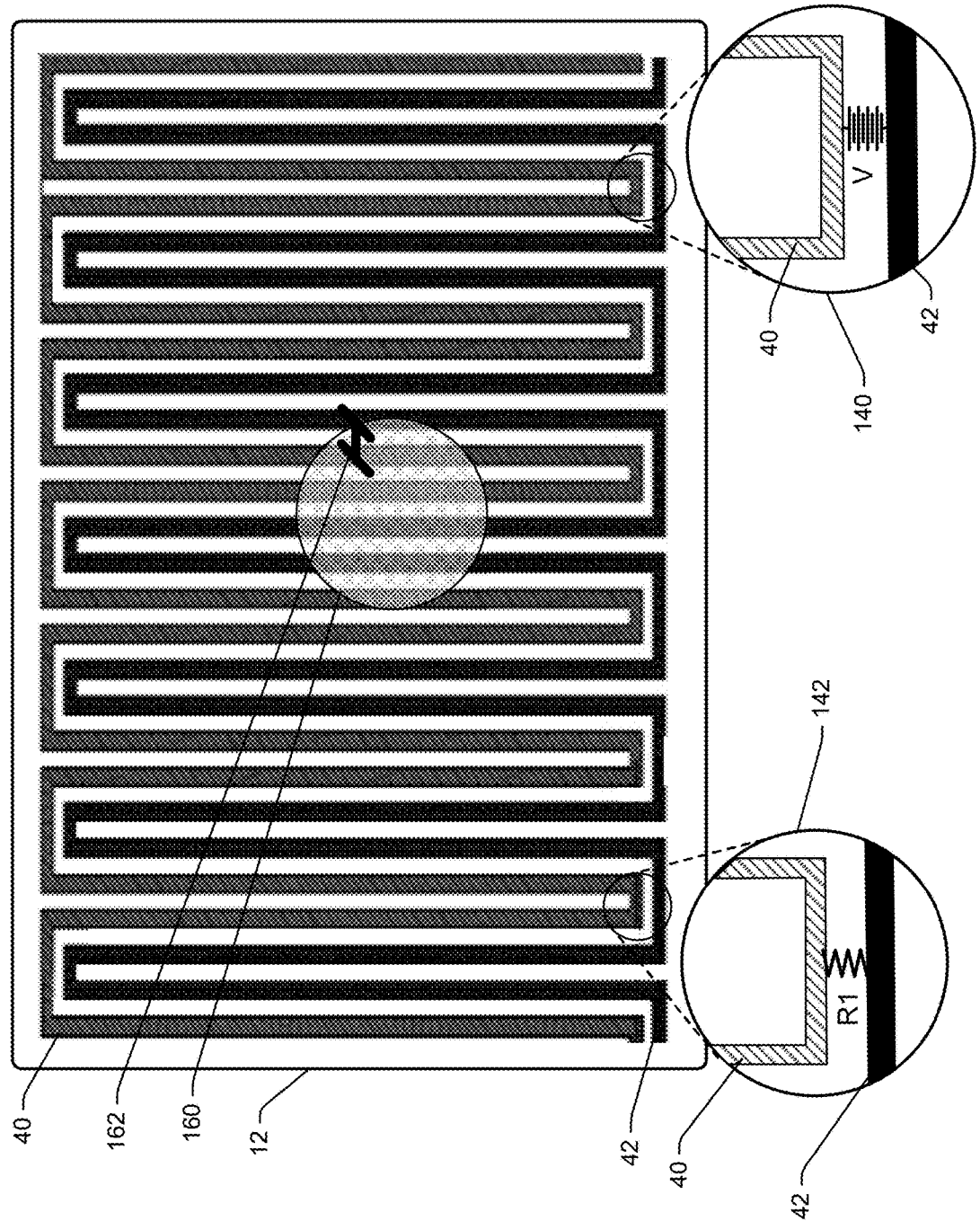
FIG. 11 is similar to FIG. 10, albeit showing the pad with a larger wet spot.
Figure 12:
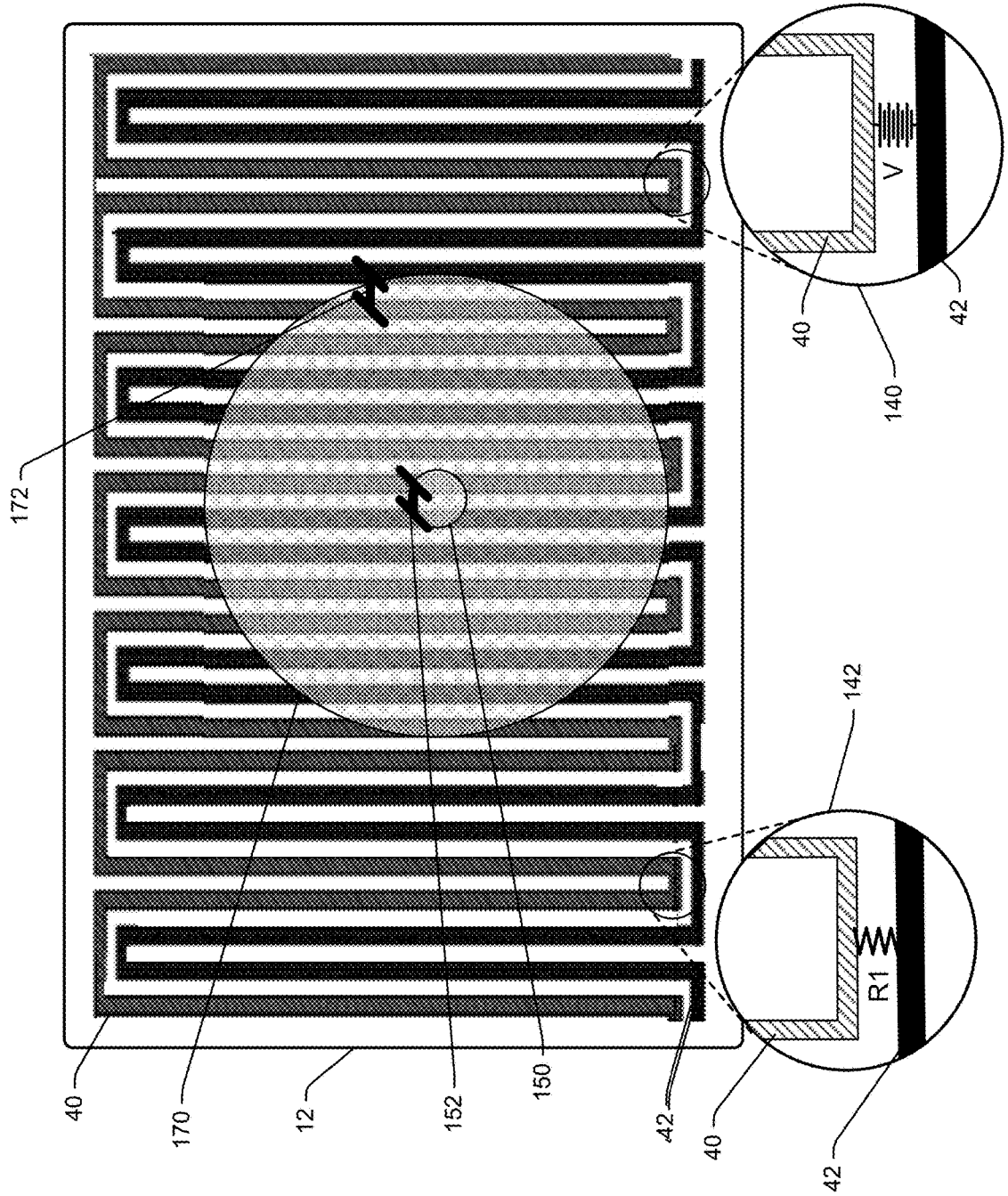
FIG. 12 is similar to FIG. 1021, albeit showing the pad with a small wet spot and then a larger wet spot.

Referring to FIG. 11, a larger wet spot is shown at 160 which extends across several different sections of the traces 40 and 42. Here, processor 80 would detect short 162 as illustrated and therefore would associate the short location 162 with the current location of at least an edge of the wet spot 160. Referring to FIG. 12, a larger wet spot is shown at 170 which extends across several different sections of the traces 40 and 42. Here, processor 80 would detect short 172 as illustrated and therefore would associate the short location 172 with the current location of at least an edge of the wet spot 170 and, with some algorithms, could estimate the locations of edges of the wet spot at two or more locations.

In at least some cases processor 80 or some other system processor (e.g., in device 16, at the server 28, etc.) or computing device may be programmed to track the progression of growth of a detected wet spot over time and use that information to estimate other conditions. For instance, referring again to FIGS. 10 through 12, where spot progression is tracked over time form the initial spot 150 at 152, processor 80 may be able to estimate a likely wet area corresponding to a current wet spot by assuming that the spot generally expands in a circular shape from an originally detected wet spot position (see FIG. 10). Here, the assumption would be that the current spot expanded equidistantly in all directions from the original short at 152 so that the overall size of spot 170 could be estimated.

As indicated above, the period between wetness state sensing activities may be constant (e.g., every second, every 3 minutes, etc.) in some embodiments. In other embodiments, in order to reduce battery usage, the period between sensing activities may be varied based on most recent detected conditions. For instance, an initial period between detections may be set to 3 minutes. Once an initial small wet spot is detected, the period may be shortened to 1 minute. Once a pad reaches 50% absorption capacity, the period may be shortened to sensing every second so that current condition changes are monitored on a more granular level. In other cases, when a set spot is initially detected, the time between sensing events may be changed from every 3 minutes to every second as the spot location or wetness continues to change during a voiding event. Once the wet spot characteristics associated with a voiding event stabilize, the time between sensing events may again be lengthened to 3 minutes assuming that the wet spot location is not near a pad edge and the time can then be shortened again once another voiding event is detected.

Figure 13:
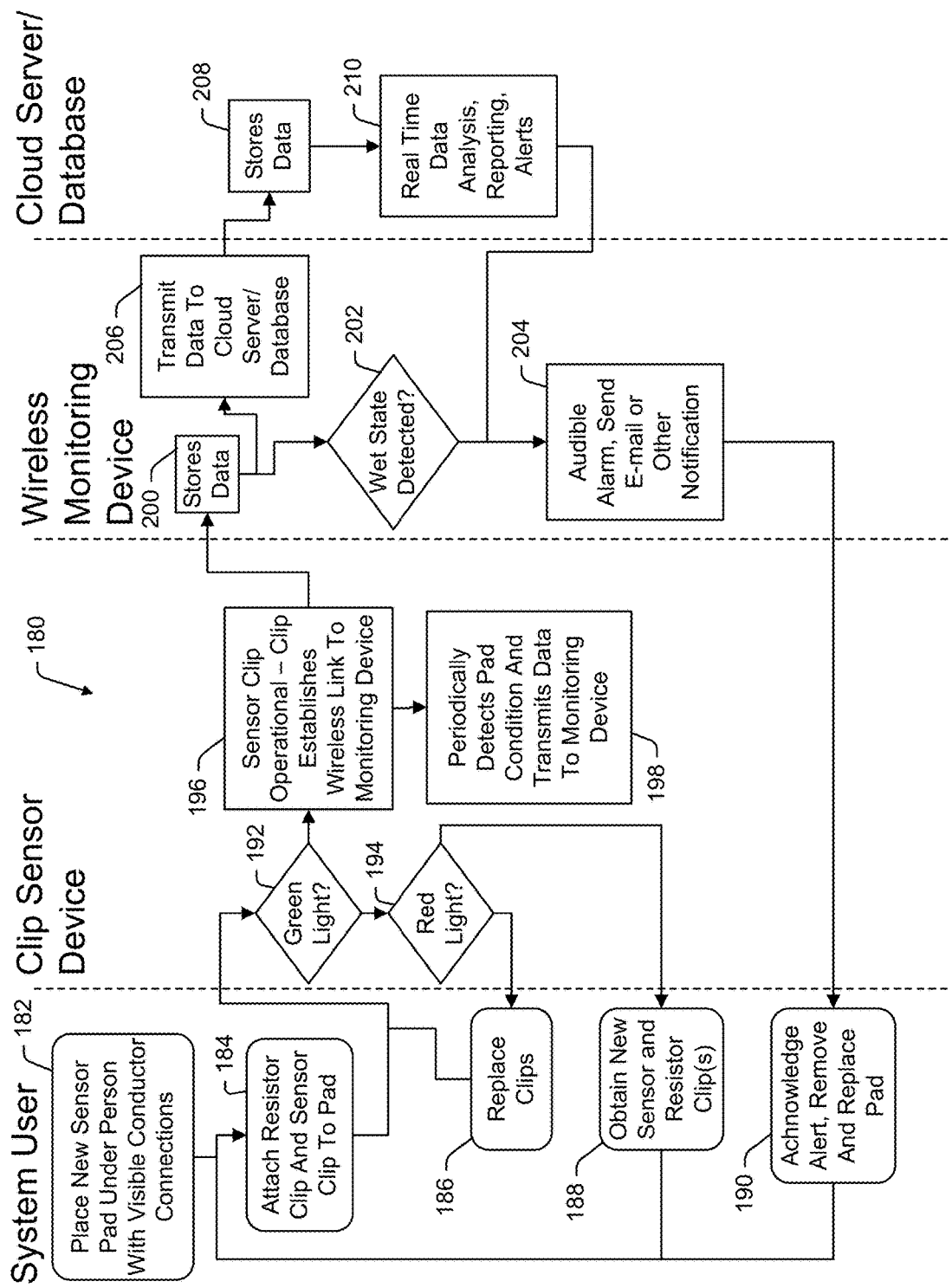
FIG. 13 is a process that is consistent with at least some methods of using the sensing system described in FIGS. 1 through 12.

FIG. 13 shows a flow chart illustrating a process 180 that is consistent with at least some aspects of the present disclosure. At block 182 an assistant places a new sensor pad 12 under a patient with the ends of traces 40 and 42 visible/exposed on the side of the bed. At block 184 the assistant retrieves a sensor clip 20 that has been programmed for a specific patient/patient bed, etc. and a resistor clip 22 and attaches the resistor and sensor clips 22 and 20, respectively, to the edge of the pad as illustrated in FIG. 1.

If the clips are properly attached to the pad and a circuit with the traces 40 and 42 is completed, at block 192 processor 80 illuminates the indicator LED green indicating to the assistant that the sensor assembly is operational. In some cases the clip processor will also generate a voice signal indicating "The clips are properly attached and the sensing assembly is now functioning." If the clips are not properly attached so that the circuit with the traces does not occur, at block 194 the processor 80 controls LED 69 to indicate the red color and at block 186 the assistant disconnects the clip(s) and reconnects the clips until the greenlight is illuminated. Improper clip connection may also result in the processor generating a voice signal "Please reattach the clips at different locations to properly configure the sensing system." If neither the green nor red condition is indicated after the assistant tries to make a proper connection, clip 22 has malfunctioned and the assistant can retrieve another sensor clip 22 at 188 and attach the new clip at 184.

Once the clip pair 20 and 22 is operational at block 196, the clip processor 80 establishes a wireless link to a proximate portable monitoring device 16 (see again FIG. 1). Once the link is established, processor 80 periodically detects the state of pad wetness and transmits that data to device 16. In addition to indicating wet state in some fashion, in at least some cases the data includes information indicating the building, floor, room, bed and/or patient that the pad is associated with so that the system can associated wet state with particular location and/or patients and pads. At block 200, device 16 stores the received data, detects any wet state at 202 and if the pad is wet at all, generates an alarm or warning for the assistant at 204 indicating the wet state as well as location, bed, pad or patient identifying information so that the assistant can quickly locate wet pads if desired. Here, in at least some cases the wet state may be indicated in different wet gradations such as, for instance, dry, damp, wet, wetter, extremely wet. Based on pad condition and other factors (e.g., duration since initial wetness, a patient's specific voiding schedule, a patient's specific health state or other conditions, etc.), the assistant can decide when to acknowledge a wet condition and when to remove and replace a soiled pad as indicated at 190.

Referring still to FIG. 13, the wet state data in some embodiments is transmitted to a remote server at 206. The server stores the received data at 208 and performs real time or batch analysis on the received data at 210 to generate various graphical output interfaces for the assistant or others to view. The server can provide other signals back to the assistant as indicated at 204.

Figure 14:
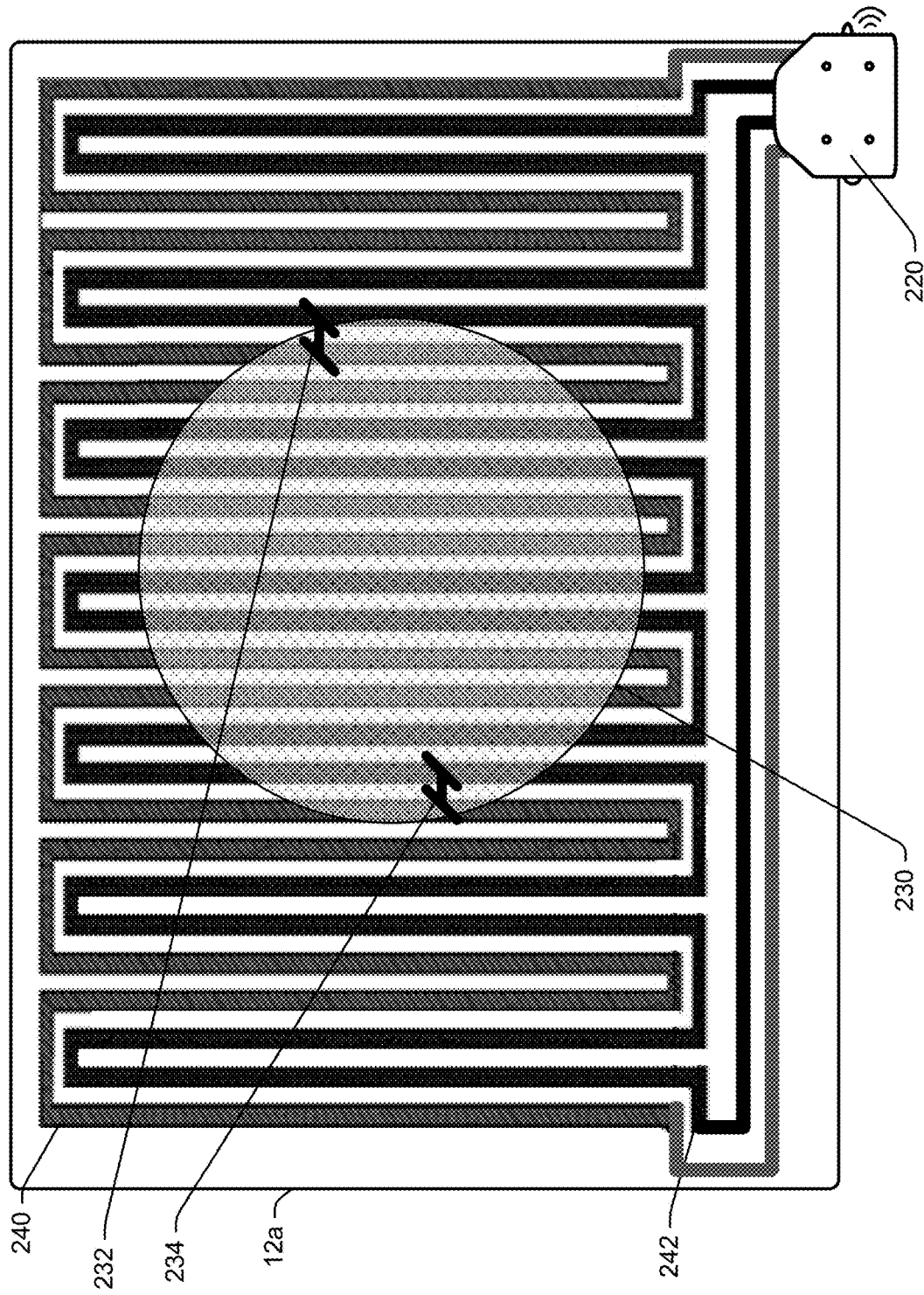
FIG. 14 is a schematic that shows another pad type with a different trace pattern where a single sensing clip provides both the sensing resistor and a voltage source and sensing circuitry.

Referring now to FIG. 14, another sensor assembly configuration is illustrated that includes a pad 12a having a different trace pattern and that includes a single clip device 220 that has both a resistor and the sensor circuitry in a single housing. Here the trace pattern includes an anode trace 240 and a cathode trace 242 which again form serpentine interleaved patterns where each portion of the anode is adjacent a portion of the cathode trace. In this case, the both ends of the anode and cathode trace return back to a single clip attachment location so that the single clip 220 can be attached to the pad to create the sensing circuit. Here, the clip 220 is shown wide but in other embodiments it is contemplated that the clip assembly 220 may have dimensions akin to those shown in other embodiments related to clip 22, albeit where the traces come together in a smaller area than that illustrated in FIG. 14.

In at least some embodiments it is contemplated that the clip processor 80 in the single clip design 220 shown in FIG. 14 may be programmed to change which ends of the traces the voltage is applied to and which ends the resistance is applied to so that the sensor device can detect two different shorts between the traces where those two points can be used to more accurately determine an area associated with an identified wet spot. In this regard, see the exemplary wet spot 230 in FIG. 14. Here, with voltage applied to a first end of the traces and the resistor to the second end, the clip processor can identify the location of short 232 at one edge of spot 230 and, with voltage applied to the second end of the traces and the resistor to the first end, the processor can identify the location of short 234 at another edge of spot 230. Using the locations of the two shorts 232 and 234, processor 80 can determine the size of spot 230 relatively precisely.

Figure 15:
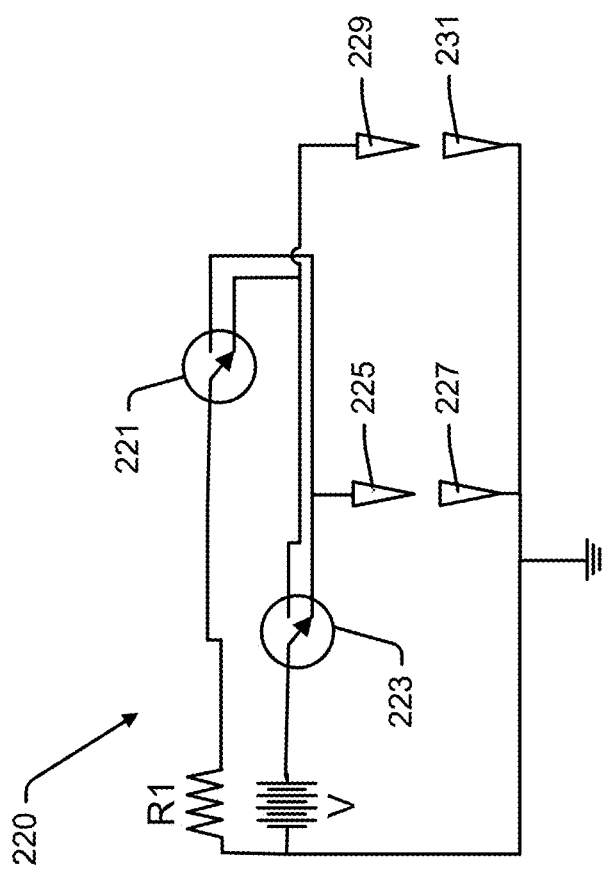
FIG. 15 is a schematic illustrating a simple switching circuit for switching the sensing resistor and voltage source between ends of pad traces that is consistent with at least some aspects of the present disclosure.

Referring to FIG. 15, exemplary components that comprise part of clip assembly 220 are illustrated including a battery power source V, a resistor R1, two switching devices 221 and 223, a first prong pair 225, 227 and a second prong pair 229 and 231. Switch 221 is linked to resistor R1 and is controllable to place resistor R1 across either pair 225, 227 or pair 229, 231. Similarly, switch 223 is linked to resistor the power source V and is controllable to place a voltage across either pair 225, 227 or pair 229, 231. Here, the clip processor (not shown in FIG. 15) controls the switches 221 and 223 to alternately place the voltage and resistor across the different prong pairs to measure wet spot short locations from either end of the trace pair.

Figure 16:
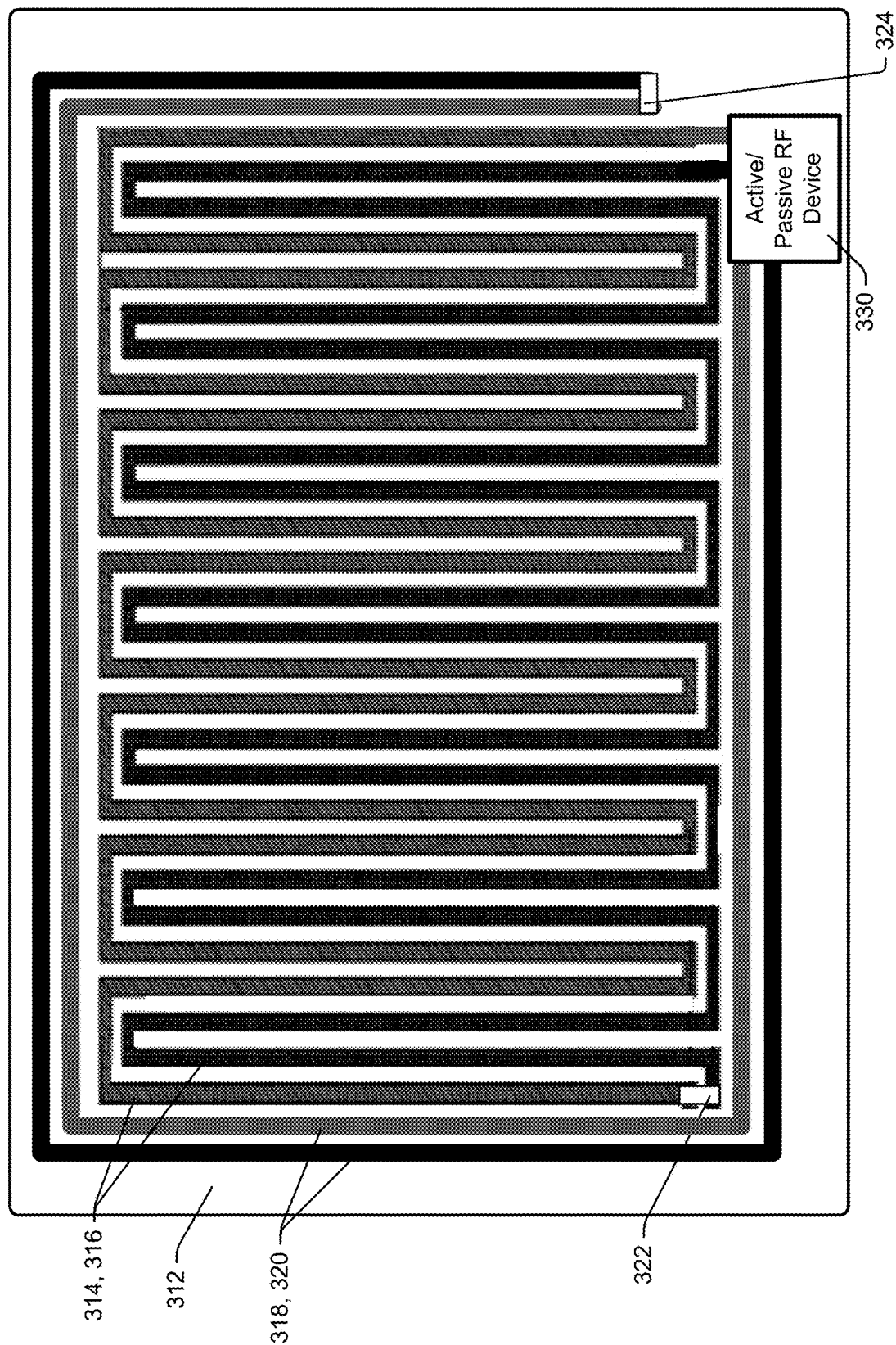
FIG. 16 is a schematic illustrating a pad with yet another trace pattern that includes two separate trace patterns and printed resistors where the pad also includes an RF transmitting device.

Referring now to FIG. 16, another wetness sensing pad embodiment 312 is illustrated that is different than the systems above in several ways. First, the pad 312 includes two pairs of traces, one pair 314 and 316 that forms a serpentine pattern centrally with respect to the pad area and a second border pair 318 and 320. Second, instead of including a resistor clip, this embodiment includes resistors 322 and 324 printed or otherwise permanently attached at second ends of each of the trace pairs. Third, instead of including a sensing clip, this embodiment includes an active or passive RF device 330 to detect wetness and transmit a signal out to a portable computing device 16 or the like. Here where device 330 is passive, an excitation element is needed to collect data from that device. In this case, in addition to detecting wetness, a device processor can use signals captured from the border trace pair 318 and 320 to determine when wetness is near an edge of the pad 312 and the system can generate a special alert when such a condition occurs. Here, in at least some cases, the device 330 would alternately apply a voltage across the first and second trace pairs to detect wetness. Applying a voltage to the pair 318, 320 that frames the pad area enables the sensor device to detect wetness near the edge of the pad so that the sensor can alert a patient or assistant to a potential edge leak condition.

Applying a voltage to the central trace pair 314, 316 enables the sensor device to detect wetness at locations within the central portion of the pad independent of the sensing that occurs at along the edges.

Figure 17:
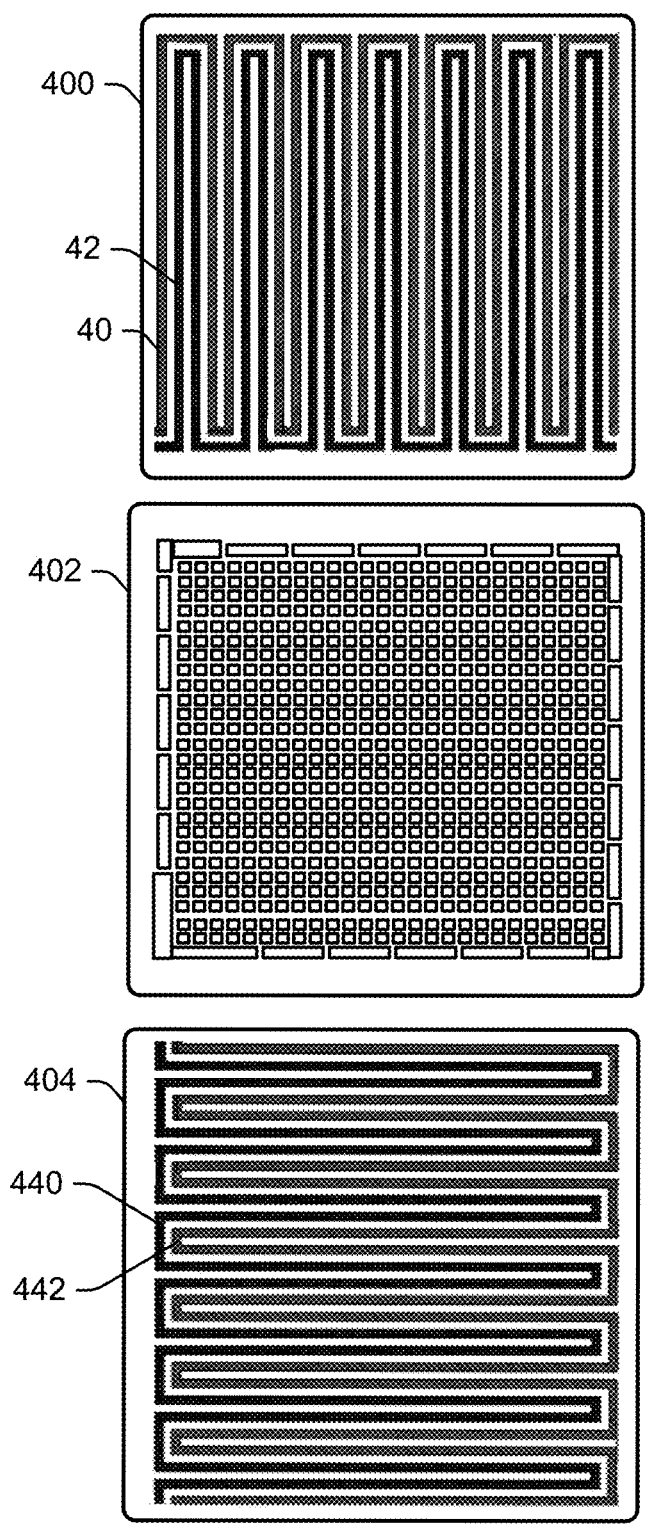
FIG. 17 is an exploded schematic view showing another printed sensing pattern.

Referring now to FIG. 17, yet another pad trace embodiment is illustrated in an exploded view. FIG. 17 shows three separate printed patterns including a first conductive trace pattern 400, an intermediate pattern that includes insulative material 402 and a second conductive trace pattern 404. First conductive trace pattern 400 is akin to the trace pattern described above with respect to FIG. 2 and, to that end, includes a first trace pair including interleaved anode and cathode traces 40 and 42, respectively. Second conductive trace pattern 404 is essentially the same pattern as the first pattern 400 and includes a serpentine pattern including an anode trace 440 and a cathode trace 442. Second trace pattern 404 is printed at a 90 degree angle with respect to first trace pattern 400 as shown in FIG. 17. Referring still to FIG. 17, the intermediate printed pattern including an electrically insulative material 402 has a pattern that mirrors the combination of patterns 400 and 404.

During printing, first conductive pattern 400 is printed on a PE film as shown in FIG. 17. Next, intermediate pattern 402 is printed on the film so that electrically insulating pads in pattern 402 are printed over segments of traces 40 and 42 that would overlap with segments of the traces 440 and 442 in Second trace pattern 404. In particularly advantageous cases, the height and width dimensions of each of the pads in pattern 402 are greater than the width dimensions of the traces in patterns 400 and 404 to ensure that once pattern 404 is printed, there is no short circuit between traces in pattern 400 and traces in pattern 404. After pattern 402 is printed, pattern 404 is next printed over the film and the pads in pattern 402 so that no part of any of the traces 440 and 442 contacts any part of traces 40 and 42.

Figure 18:
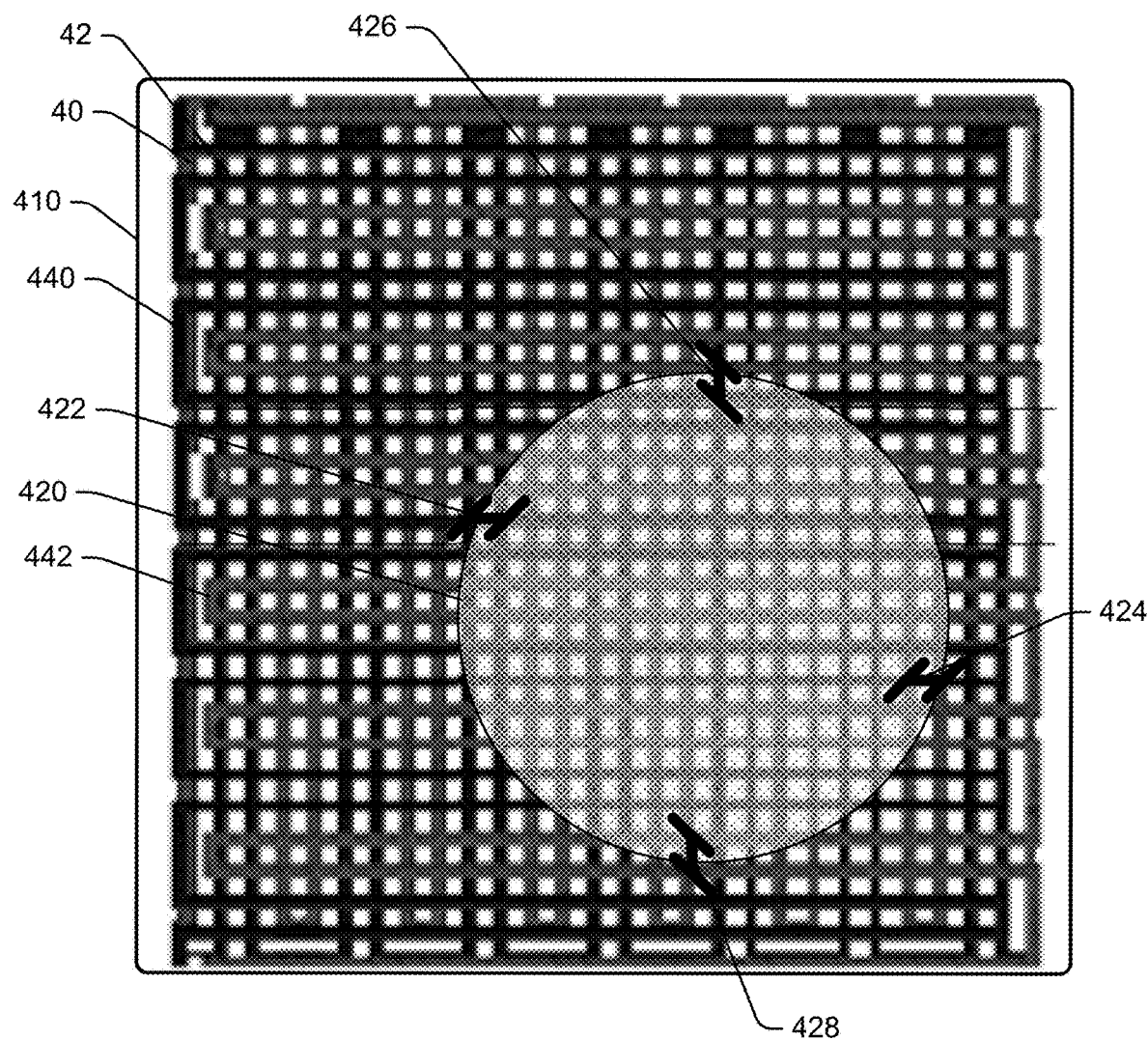
FIG. 18 shows a pad that has the pattern shown in FIG. 17 with a wet spot on the pad.

Referring still to FIG. 17, while not shown, one or more clips (depending on trace design and clip construction) are connected to a pad including the trace arrangement shown in FIG. 17 and the clip(s) are controlled to apply voltage across each trace pair 40, 42 and then 440, 442 and resistance measurements are taken. Here, in addition to determining wet spot location in one direction (e.g., from lateral side to lateral side of the pad), the system can be used to detect wet spot location in two dimensions (e.g., left to right and top to bottom) to provide additional useful information useable to plan replacement activities. In this regard, see the exemplary pad 410 that is constructed using the three printing layer technique described in FIG. 17 that is shown in FIG. 18 that includes a wet spot 420. In a case where voltage is applied at different sensing times to each end of the first conductive trace pair 40 and 42, each of short locations 422 and 424 can be identified and, where voltage is applied at different sensing times to each end of the second conductive trace pair 440 and 442, each of short locations 426 and 428 can be identified so that the overall size of spot 420 can be more clearly defined.

While it is advantageous if all pads are manufactured to have the same operating characteristics, it has been recognized that depending on materials used to construct a pad as well as manufacturing constraints that even similar pads may operate differently because of mechanical differences like trace thickness or absorption into a substrate, trace width, etc. For this reason, in at least some cases it is contemplated that when a sensor is attached to a specific pad, the sensor processor may detect an initial resistance of the pad and then make adjustments based thereon regarding spot locating algorithms based on specific pad resistance initially detected. Here, it is contemplated that a table may be stored that represents different resistances within a range of possible expected initial resistance values that correlates shorted locations on a pad with resistance changes. Then, when the processor detects an initial dry pad resistance, the processor can access the table, identify short location data to use to assess where a spot occurs based on resistance changes and operate accordingly.

Figure 19:
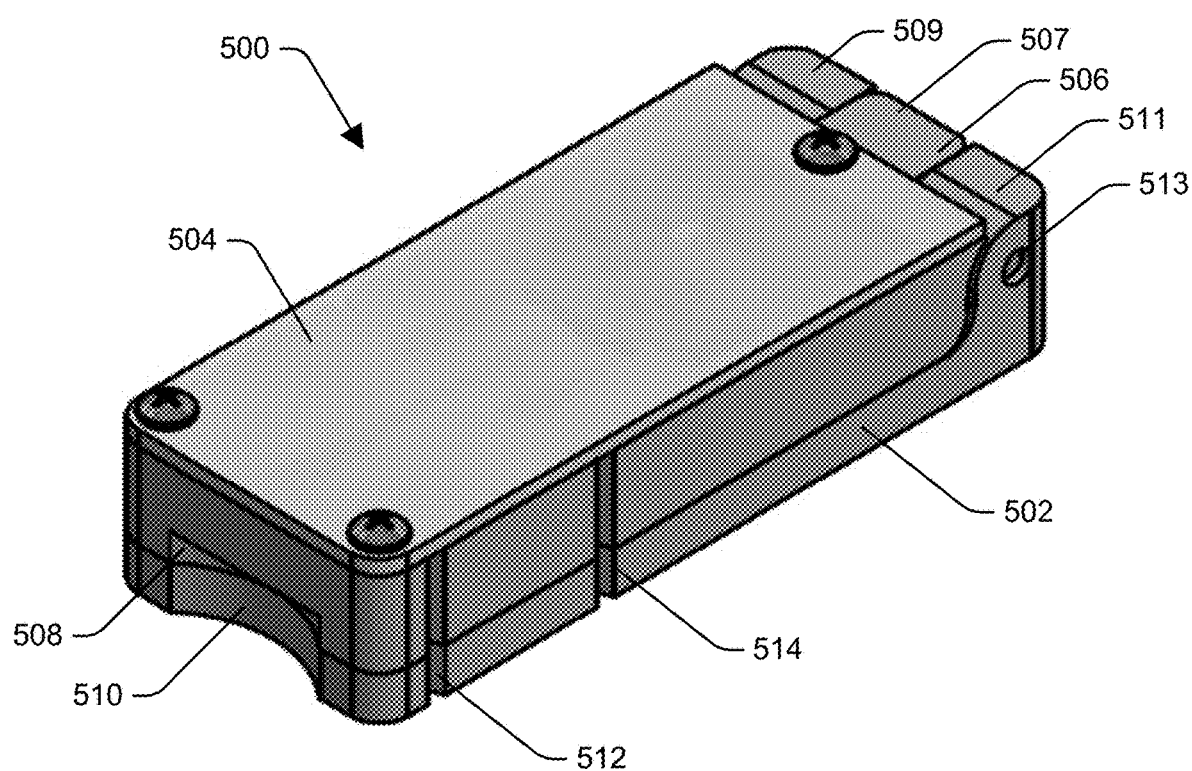
FIG. 19 is a perspective view of another sensor clip assembly that is consistent with at least some aspects of the present disclosure.
Figure 20:
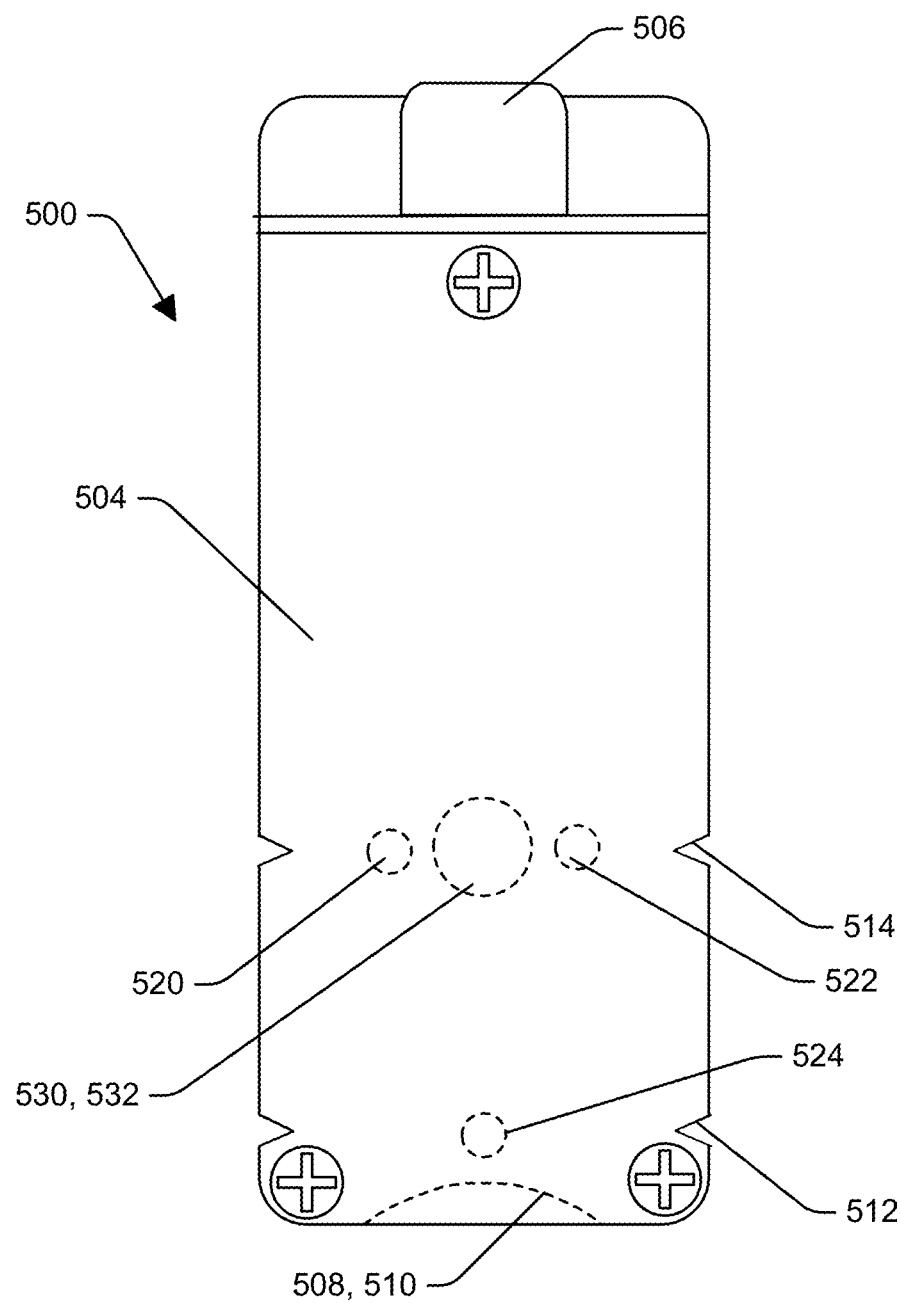
FIG. 20 is a top plan view of the clip assembly of claim 19 showing some hidden components in phantom.
Figure 21:
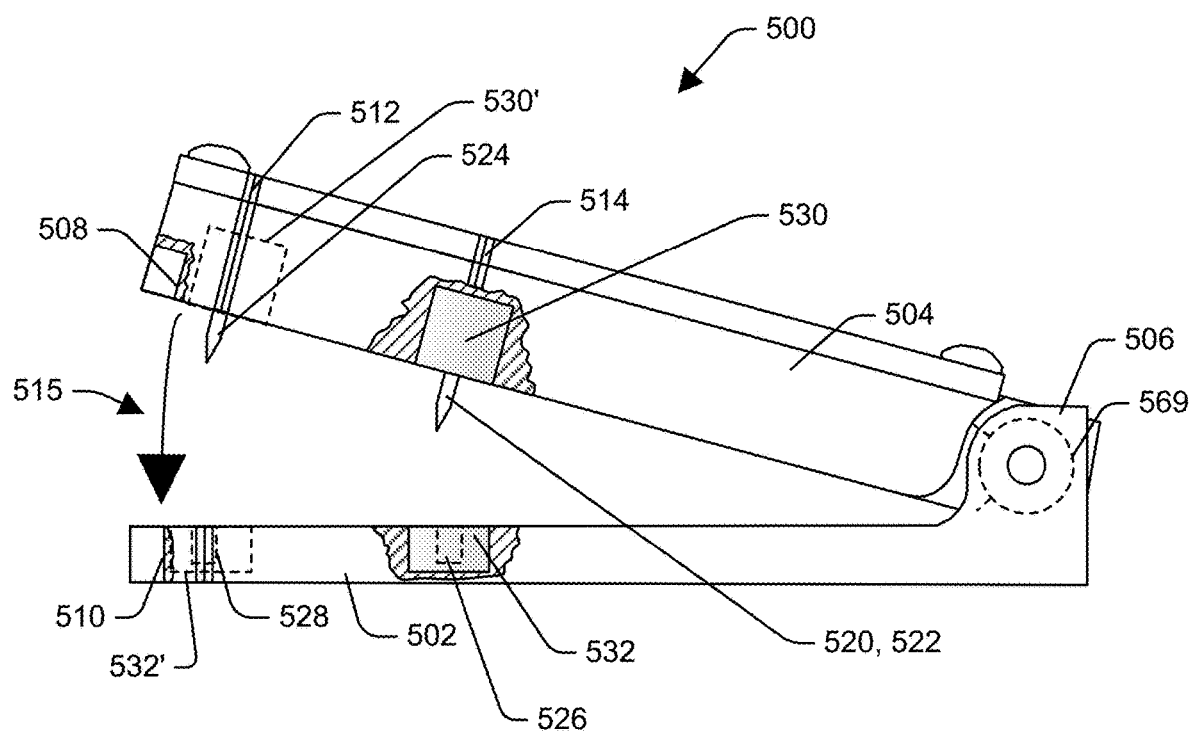
FIG. 21 is a side view of the clip assembly of FIG. 19 in an open state with some portions shown in cross section.

Referring now to FIGS. 19 through 22, another advantageous embodiment of a sensing clip assembly 500 is illustrated that is constructed in a similar fashion to the embodiment shown in FIG. 3, albeit with a few design modifications that make it possible to have smaller overall dimensions, a more boxlike shape, and a construction that is easier to keep clean, sterilize and store (e.g., the storing shape is more compact). Assembly 500 includes a housing 504 and a lower jaw 502 that are hinged 506 at one end so that the jaw can be pivoted away from the housing into an open state as shown in FIG. 21. To minimize a height H3 dimension (see FIG. 22) of the closed clip assembly 500, the hinge 506 is formed so that hinge components interlock within a space defined by a height dimension H4 of the housing 504. To this end, housing 504 includes a central hinge member 507 that extends rearward from a main housing structure and jaw 502 includes first and second hinge members 509 and 511 that extend upward at a hinge end forming a channel therebetween where central hinge member 507 is received within the channel. A hinge pin 513 extends through members 507, 509 and 511 forming a hinge pivot axis.

Figure 22:
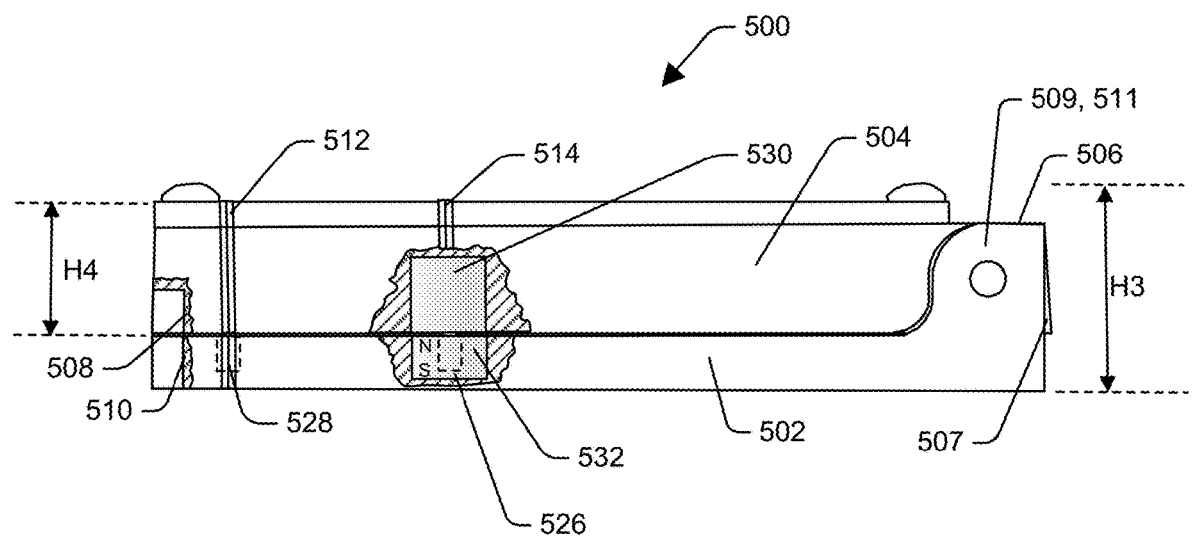
FIG. 22 is similar to FIG. 21, albeit with the clip assembly in a closed state.
Figure 23:
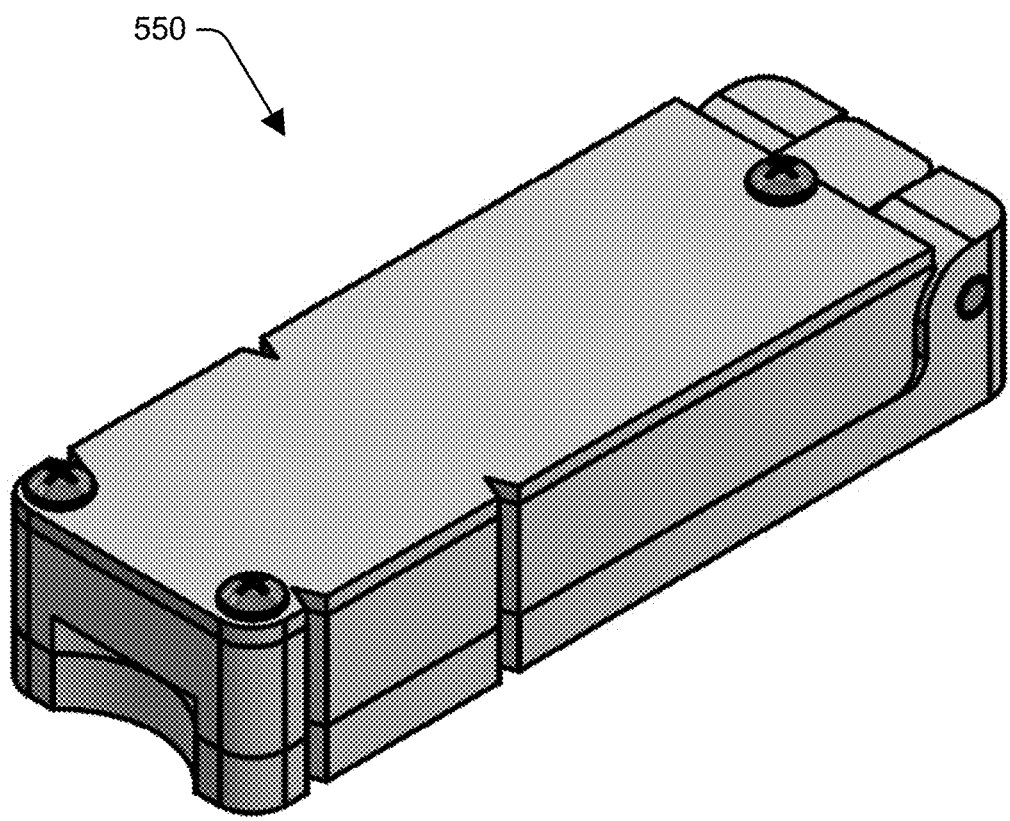
FIG. 23 is a perspective view of another resistor clip assembly that is consistent with at least some aspects of the present disclosure.
Figure 24:
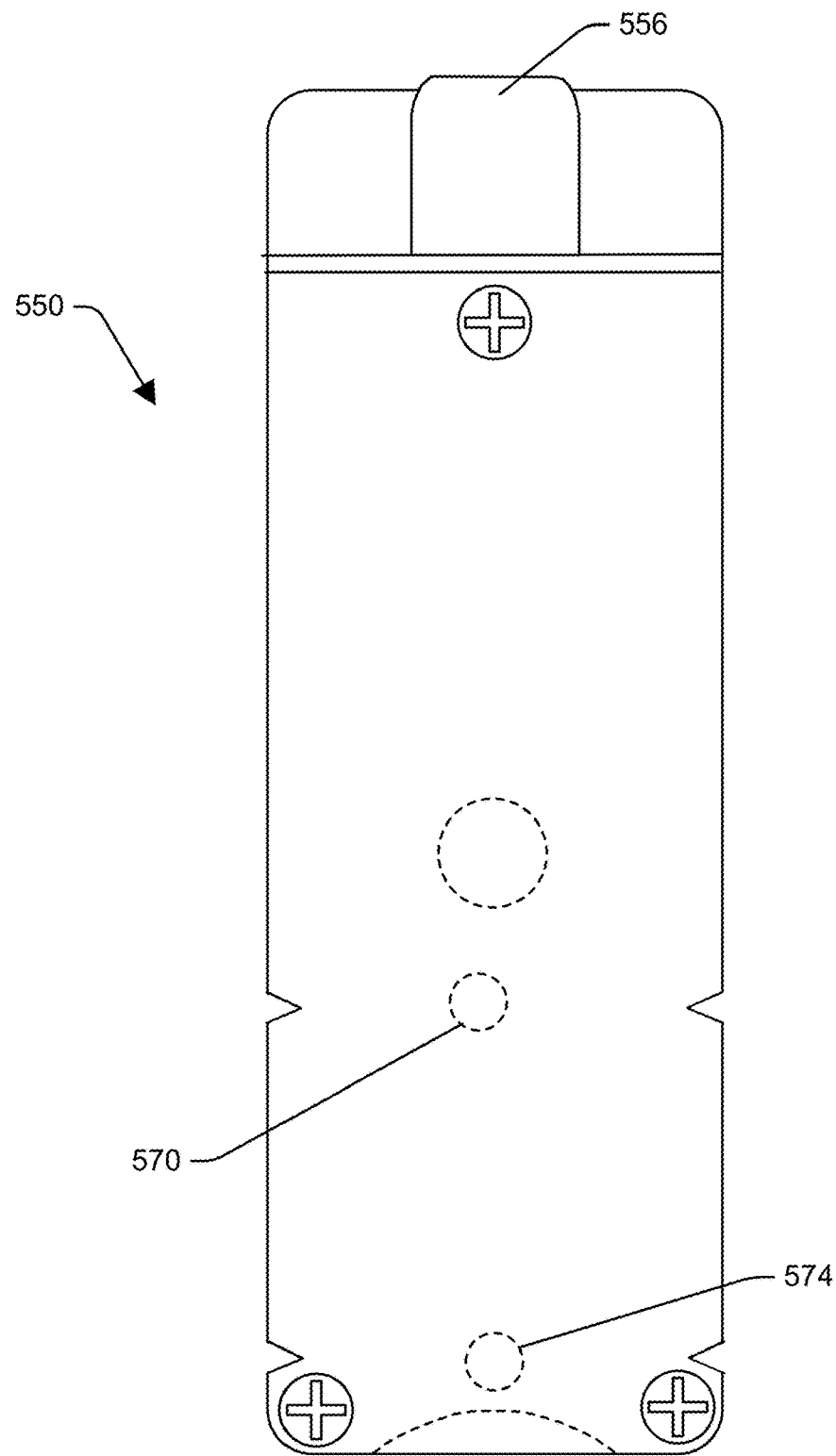
FIG. 24 is a top plan view of the clip assembly of claim 23 showing some hidden components in phantom.
Figure 25:
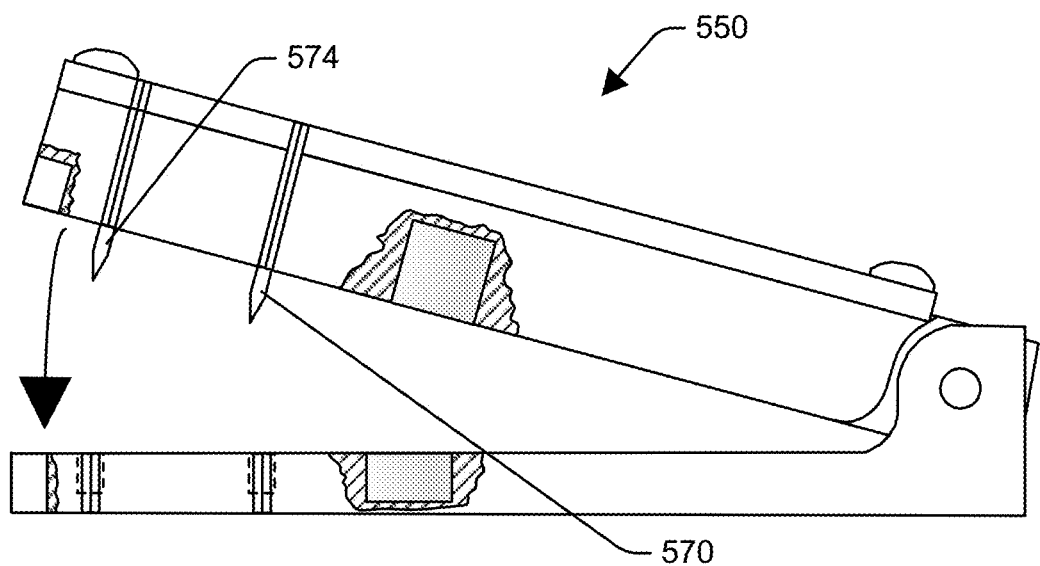
FIG. 25 is a side view of the clip assembly of FIG. 23 in an open state with some portions shown in cross section.
Figure 26:
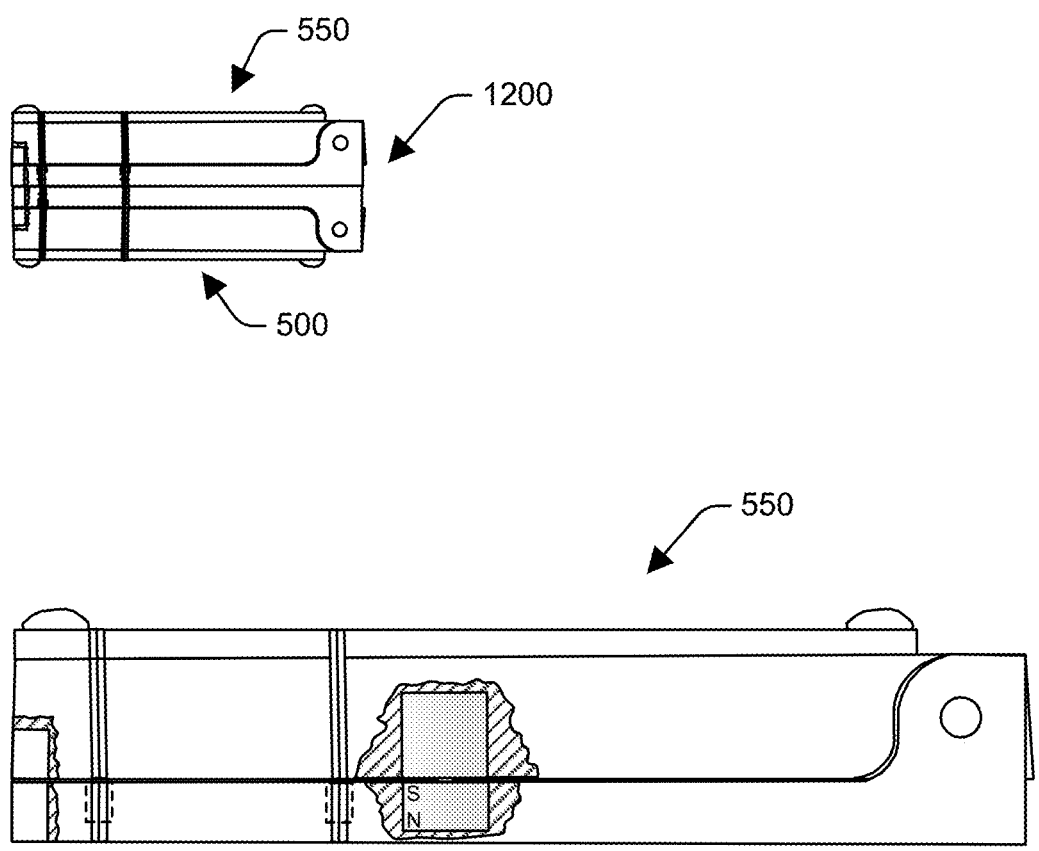
FIG. 26 is similar to FIG. 25, albeit with the clip assembly in a closed state.

As best seen in FIG. 22, a height dimension of members 509 and 511 is substantially similar to the height H4 of housing 504 so that the hinge is formed within the height dimension of housing 504. In other embodiments the jaw 502 may form the central hinge member and housing 504 may form first and second lateral members that receive the central member therebetween.

While some embodiments will not include any type of spring at hinge 506, in other embodiments there may be a spring 569 (shown in FIG. 21 in phantom) that tends to force jaw 502 away from housing 504 and into an open state or condition when not closed. By forcing the jaw and housing apart until pressed closed, assembly 500 makes it easier for a user to clamp assembly 500 to the edge of a sensing pad assembly. To this end, with a gap 515 formed by assembly 500 in the open state, the gap can be aligned with the edge of a sensing pad and moved toward the edge until the edge is received within the gap 515. A user presses the housing and jaw together to clamp assembly 500 to the edge of the pad assembly.

In at least some embodiments there are finger recesses in front ends of the housing and jaw as shown at 508 and 510 so that a user can grip the distal ends of the housing and jaw to pull them apart when the clip assembly is to be opened. As shown, finger recess 510 extends an entire height dimension of jaw 502 and recess 508 only extends about half the height of housing 504 to provide a lip for finger gripping. While the recesses are shown in a surface opposite the hinge 506, in other embodiments the recesses may be formed in one or both side surfaces of housing 504 and jaw 502.

Referring still to FIGS. 20 through 22, clip assembly 500 includes electrical contact pins 520, 522 and 524 akin to contact prongs 75, 77 and 89 described above in FIG. 4 that extend from an inside surface of housing 504 and that are spaced such that they make electrical connections with sensor traces on a sensor pad when connected thereto. Lower jaw 502 forms openings 526 and 528 to receive distal ends of the connector pins when the jaw 502 is closed to the housing 504 as in FIGS. 19 and 22. In at least some cases the distal pin ends fit tightly within openings 526 and 528 so that when clip 500 is attached, the pins friction fit within the openings and help maintain the clip closed and on an edge of an attached pad until the clip is intentionally removed by a user. In other cases the pins do not cause much friction with the openings and instead the openings and structure that form them simply provide protection for the pin ends upon closing the clip. The pins are connected to a processor and other components that are located within a cavity formed by the housing as described above with respect to other embodiments.

In some cases the pins are soldered to a PCB that includes the sensor device processor and that is located within the housing cavity. In other cases the pins are actually crimped onto wires that are connected to the circuit board. The crimping arrangement is more robust than a soldered connection.

Indicia or recesses (or protruding ribs) 512 and 514 are formed in the side surfaces of housing 504 and jaw 502 that are aligned with the pins 520, 522 and 524 (seen best in FIG. 21). The indicia are provided to help a clip user align the clip and pins with pad sensor traces as described above in the context of other embodiments. In some cases the indicia include paint of a different color, ribs of recessed slots. In some cases the alignment indicia (e.g., see 512 and 54 in FIG. 19; 1002 in FIG. 43) may be painted or formed using a material that absorbs and then emits light at least somewhat to assist a user in manipulating and aligning a clip at night.

Referring still to FIGS. 21 and 22, in at least some embodiments clip assembly 500 includes magnets 530 and 532 integrated into housing 504 and lower jaw 502 with facing attracting surfaces that are flush or substantially flush with internal faces of the housing and jaw. When clip 500 is open as shown in FIG. 21, the magnetic force is insufficient alone to close the clip. Once the clip is closed as shown in FIG. 22, the force between the magnets at least helps to maintain the clip closed until intentionally pried open by a user. In some cases the magnetic force alone is sufficient to maintain the clip closed during normal use. In other cases, the magnets are selected such that a combination of magnetic force and, in at least some cases, frictional force between the contact pins and openings is sufficient to maintain the clip closed during normal use (e.g., until intentionally pried open).

Referring still to FIG. 21, magnets 530 and 532 are shown located near a midpoint along the lengths of the jaw and housing 502, 504, respectively. In other cases the magnets may be located near the distal ends of the housing and jaw as shown in phantom at 530 and 532, respectively, to increase effectiveness at maintaining the jaw in a closed position. For instance, the magnets may be mounted within the distal one tenth of the length of the jaw to increase the lever force of the magnets when in the closed state.

An additional advantage of providing magnets in the clip assembly is that the magnets can operate as a coupling mechanism to other metal structures during storage. For instance, where the thickness of the jaw 502 in FIG. 21 is minimal (e.g., a thin plastic layer) so that magnetic force occurs through that layer, a clip may be magnetically mounted to any flat metal surface. In other cases an edge of a metal member (e.g., a metal clip board or the like) may be slid into an open clip gap so that inside surfaces of the magnets secure to the metal member.

FIGS. 23 through 26 illustrate another embodiment of a resistor clip 550 that is similar to the resistor clip described above with respect to FIGS. 7 and 8, albeit having design features that are similar to the features described above with respect to the sensor clip 500 shown in FIG. 19 through 22. Here, it should be appreciated that assembly 550 again has design features that result in an overall smaller device that is more box-like (e.g., no arm or finger members that extend outward) and that is easier to keep clean and to sterilize (e.g., the gap required for the spring in the FIG. 7 embodiment is eliminated).

While resistor clip 550 is shown as having a housing and a jaw that have height dimensions similar to height dimensions of components of sensor clip 500 in FIG. 19, in other embodiments it is contemplated that the resistor clip 550 may have smaller height dimensions as that device only requires minimal circuitry (e.g., a resistor) to perform its function. For instance, in at least some cases the height of the resistor clip housing may be between one sixteenth of an inch and one half an inch so that the overall height dimension of clip 550 is further minimized.

While not labelled, resistor clip 550 includes trace connecting pins, magnets and a hinge arrangement that is similar to the same components described above with respect to FIGS. 19 through 22.

In some embodiments the polarity of the magnets may be revered in the sensor clip 500 and the resistive clip 550. To this end, see that in FIG. 22 the south magnetic pole is facing downward toward the bottom of the jaw member in sensor clip 500 and in FIG. 26 that the north magnetic pole is facing downward toward the bottom of the jaw member in the resistive clip 550. See also at 1200 in FIG. 26 that with those magnetic arrangements the jaw member magnets in the two clips 500 and 550 attract and therefore that a clip pair 500/550 can be stored as a connected combination until intentionally separated for use.

In at least some cases it is contemplated that a single clip having the design features of clip 500 in FIG. 19 may be configured that is akin to the clip 220 in FIG. 14 so that the single clip provides both the sensing circuitry and a resistor in a single reduced size clip arrangement. A single clip arrangement is particularly useful in applications where a patient "wears" the clip so that only one device needs to be worn as opposed to two.

Figure 28:
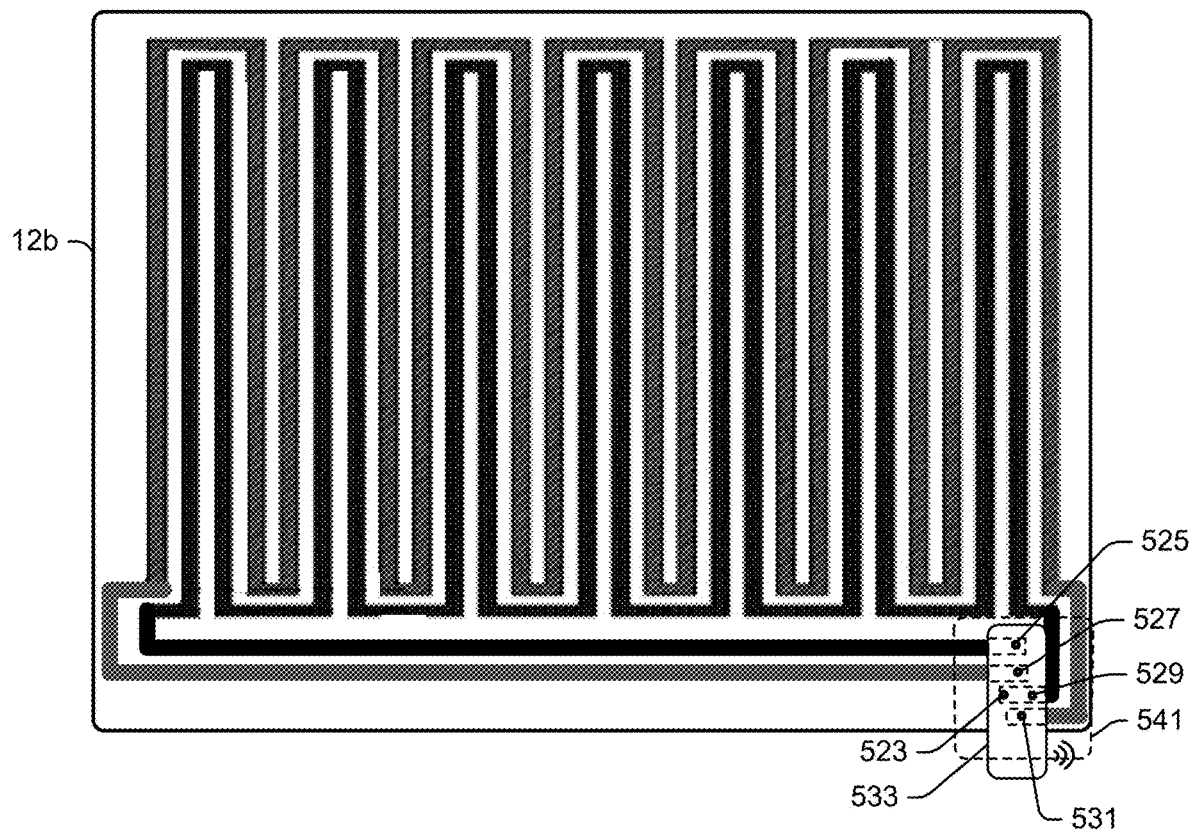
FIG. 28 is a top plan view of a sensing assembly and the combined sensor-resistor clip assembly of FIG. 27.

In a single clip configuration, the pad assembly would include traces where both ends of each trace are located adjacent a small portion of an edge of a pad assembly so that both the resistor and the sensor pins can connect to trace ends as needed (see FIG. 28).

Figure 27:
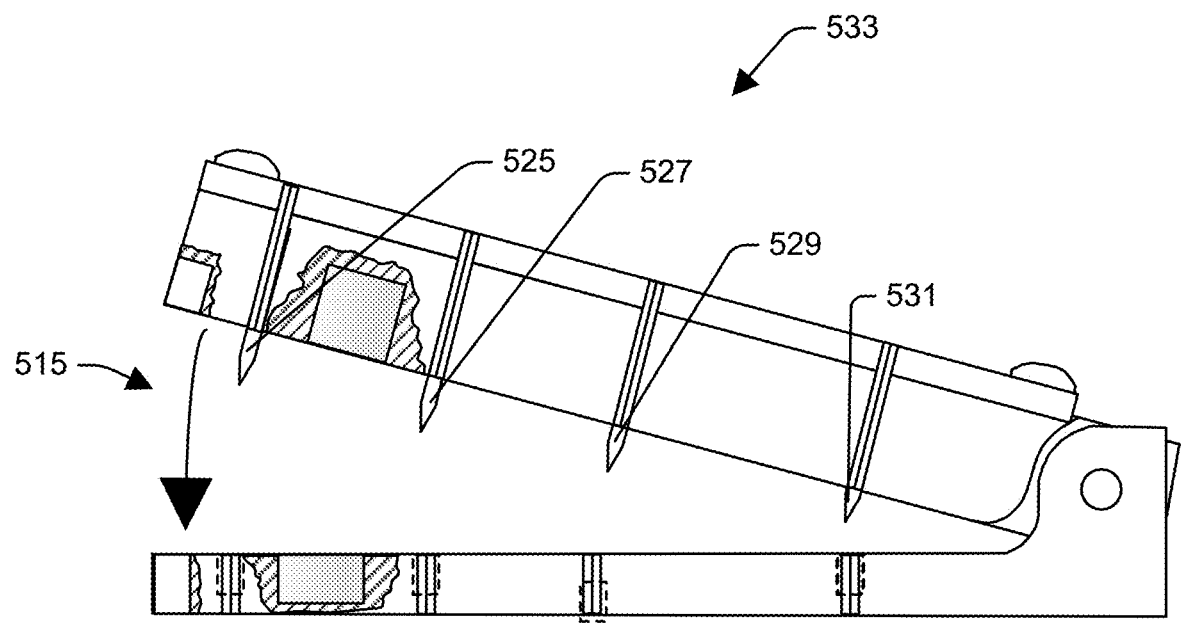
FIG. 27 is similar to FIG. 21, albeit showing combined sensor-resistor clip assembly that is consistent with at least some aspects of the present disclosure.
Figure 27:
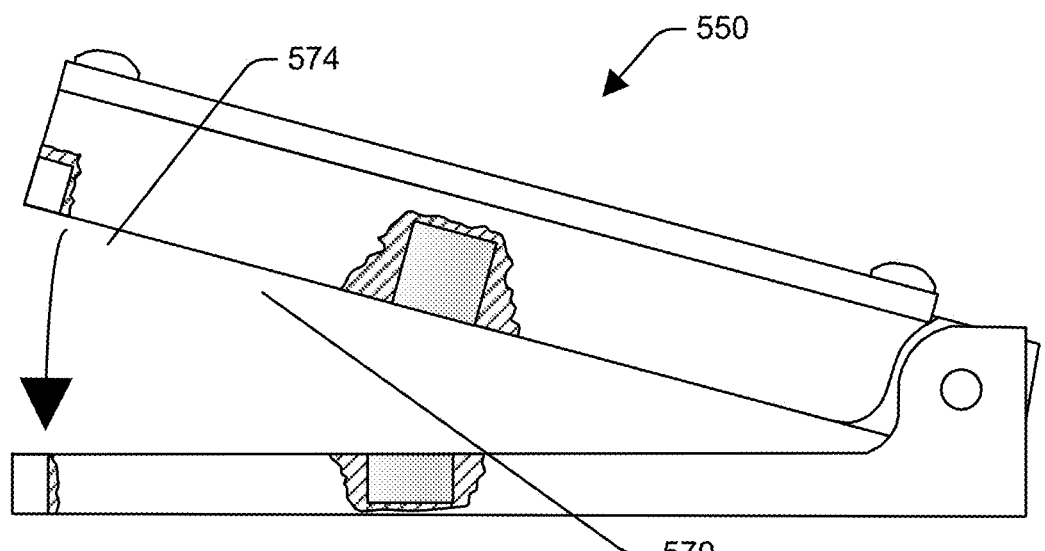

In at least some cases it is contemplated that the single clip design may have resistor and sensor contacts that are spaced apart along a length dimension (e.g., between the hinge end and opposite end) of the clip assembly so that a clip width dimension can be reduced. To this end see FIGS. 27 and 28 where resistor pins/contacts 525 and 527 as well as sensor contacts 529 and 531 are spaced apart along the single clip length so that a reduced width single clip arrangement results. FIG. 28 shows the FIG. 27 clip attached to a sensing pad assembly 12b where trace ends at pad portion 541 are aligned and parallel to the edge of the pad so that the aligned pins 523, 525, 527 and 531 contact the trace ends as shown in phantom.

One advantage of clip assemblies that rely on features other than a spring to maintain clip jaws closed is that an assembly with smaller overall dimensions can be constructed. To this end, an overall closed clip height H3 dimension of assembly 500 shown in FIG. 22 can be reduced appreciably.

Another advantage is that a more box like assembly can be constructed that has parallel oppositely facing side surfaces. To this end, see again FIG. 22 where it can be seen that when assembly 500 is closed, the top and bottom surfaces of the clip assembly are substantially flat. This closed arrangement is advantageous when storing clips as the box-like shape enables clips to be stacked in an orderly fashion for storage.

Another advantage is that there are no assembly components that extend outward out of the box like shape that could be snagged on a sheet, a user, etc., which could result in undue damage to a sensing pad assembly or discomfort for a patient. To this end see FIG. 3 where ends of the clip jaws that are spaced apart by spring 76 could be snagged while in use. The FIG. 22 clip assembly 500 does not have any extending components that can be snagged.

Yet one other advantage is that, other than the jaw gap, the FIG. 22 assembly 500 does not have any other major cracks or crevices that could become contaminated with dirt, germs, etc. Thus, assembly 500 is easier to keep clean and easier to sterilize so that the assembly can be reusable and therefore is more sustainable.

To increase patient comfort and minimize the possibility of a clip becoming dislodged from a pad, a dimensionally small clip design is preferred. To this end, in at least some cases the overall width of a clip may be anywhere within a range between one quarter inch and two inches and in particularly advantageous cases the width is within a range between three fourths inch and one and one quarter inch, the height dimension H3 of a closed clip may be within a range between one quarter inch and one inch and in particularly advantageous embodiments may be around one half an inch and the length dimension of a clip may be within a range between one inch and five inches with particularly advantageous clips having a length between two inches and four inches. The thickness of the jaw member should be minimal and, in at least some embodiments, is within a range between one tenth inch and one quarter inch with a particularly advantageous thickness of substantially two tenths inch. In at least some cases, the hinge is designed so that an angle formed by facing surfaces of the housing and jaw when in an open state is within a range between 7 degrees and 35 degrees. In some cases the open clip angle between the facing surfaces is within a range between and 20 degrees and in particularly advantageous embodiments the angle is substantially 15 degrees. With the clip open, in at least some cases the gap dimension at the distal ends of the jaw and housing is within a range between half an inch and two inches and, in particularly advantageous embodiments the gap dimension at the distal ends is substantially seven tenths of an inch, which is wide enough to easily slip the clip onto a pad edge prior to closing the jaws to secure the clip to the pad for sensing purposes.

Figure 29:
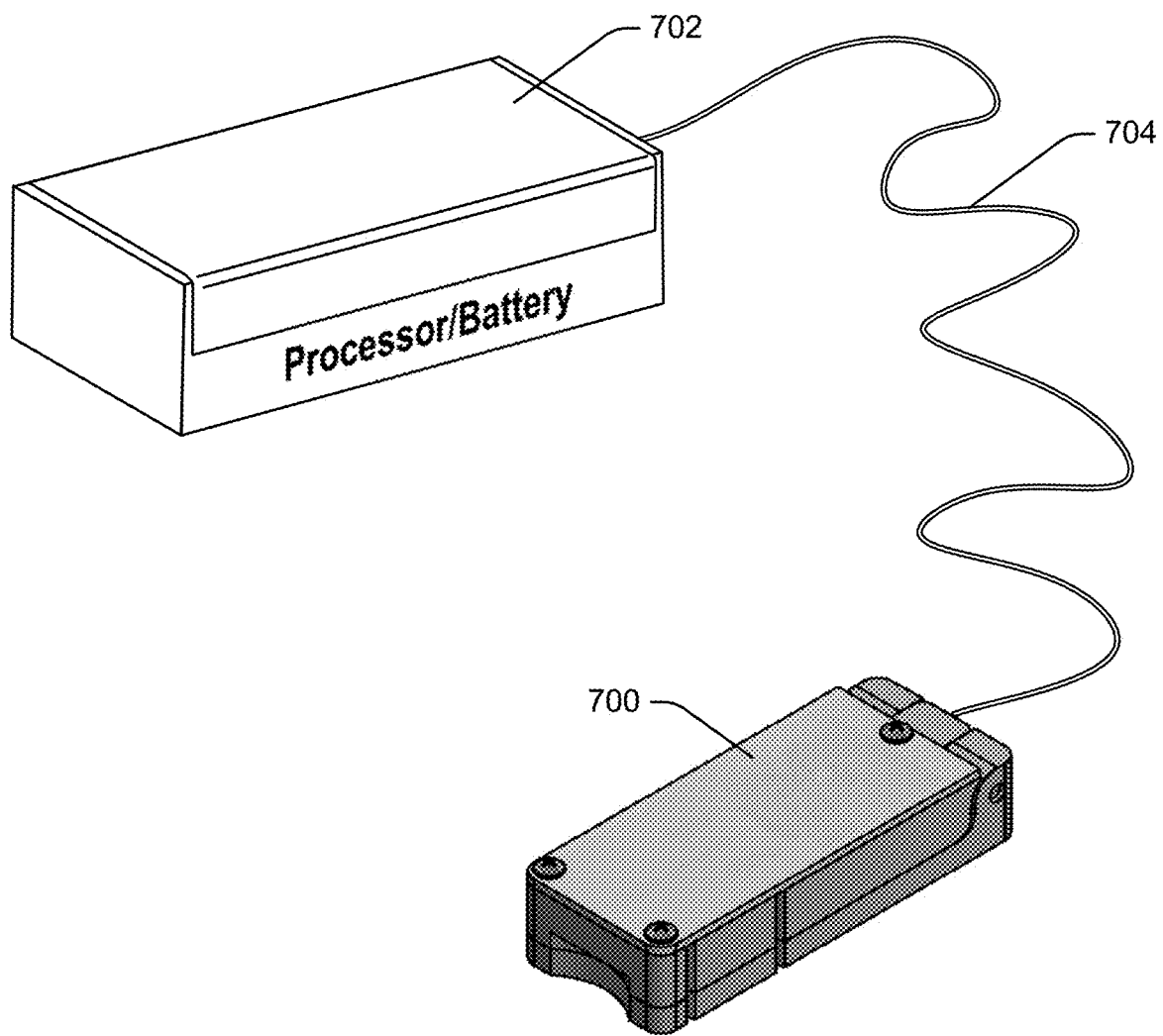
FIG. 29 is a perspective view of a clip assembly similar to the assembly shown in FIG. 19, albeit including a wired additional housing structure for accommodating several clip components in a different housing structure.

In at least some cases the overall clip assembly structure may be minimized by including at least some of the components that are described above as being located in the clip housing in a supplemental housing that is tethered to the clip housing. For instance, see FIG. 29 that shows a supplemental housing 702 that is attached to a clip assembly 700 via a wire or connection cable 704. In FIG. 29 it is contemplated that many of the components shown in FIG. 5 above may be moved into supplemental housing 702 including, for instance, processor 80, indicator 82, visual feedback circuit 69, transceiver 102, and battery 90. In other cases it may be that the indicator 82 and visual feedback circuit 69 are included in the clip housing while the processor 80 and battery 90 are located in the supplemental housing. In still other cases it may be that only the battery 90 is located in the supplemental housing 702 while all other components are included in the clip assembly 700. Where the battery is provided in a separate housing, relatively larger batteries may be included that can provide power for longer periods of time. For instance, two or three AA or AAA batteries may be included in the supplemental housing 702.

In at least some cases it is contemplated that a clip battery may be rechargeable. For instance, a clip battery may be a lithium ion type battery where the clip processor can control a battery recharging process. Here, in some cases recharging may be via electrical connection though the clip pins or the magnets or via induction. In the case of induction, a charging pad with a liquid impermeable top flat charging surface may be provided near a patient's bed or the like and a clip may be placed on the top charging surface when not in use. Thus, for instance, if a patient gets out of bed for a shower and so that a soiled pad can be replaced, the clip sensor device may be placed on the charging pad for 30 minutes and be recharged for use. Here, it is contemplated that a typical clip battery should be able to be recharged to almost full capacity within 15-30 minutes as power requirements are minimal in most cases.

While large, generally rectangular, absorptive sensor pad assemblies are described above for use in bed applications, in at least some cases smaller and/or differently shaped sensor assemblies with different types of substrate substructures will be configured that are suitable or optimized for use in other applications. To this end, the trace printing process described above can be used to print any trace patterns and therefore to accommodate other useful general wetness sensing patterns. In addition, the trace printing process can be used to apply sensor trace patterns to other substrate structures such as, for instance, a liner material without absorptive layers, a cotton or other bed sheet type material, a fabric formed into a garment that can be worn by a patient that is absorptive, breathable, or that blocks fluid from passing through, or many other substrate structures that do not melt during a printing process.

While differently shaped sensor assemblies/pads may be used in many different applications, in at least some cases the differently shaped assemblies may be purposefully configured to be used in specific applications and, in particular, for use in "wearable" applications where the sensor assembly is designed to at least somewhat contour to a patient's body when in use. By providing assemblies that contour to a patient's body, patient comfort can be increased appreciably without sacrificing any sensing capabilities. In addition, where a sensor assembly extends along a length dimension of a patient's body or a portion of the patient's body in use, at least some sensor assemblies can be used to assess a likely source of wetness on a patient's body where different sources have different health or medical implications.

Figure 30:
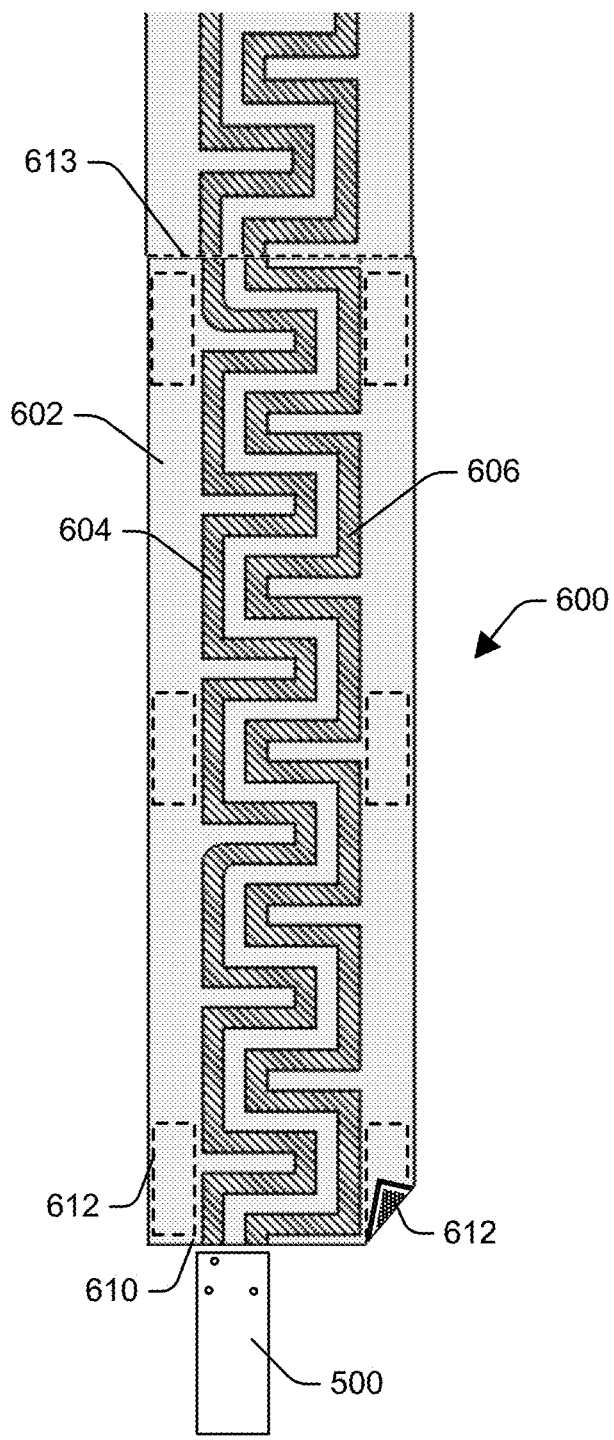
FIG. 30 is a top plan view of a sensor strip assembly and a sensor clip that are consistent with at least some aspects of the present disclosure.

Referring to FIG. 30, a first strip type sensor assembly 600 is illustrated that includes a substrate substructure 602 and at least first and second traces 604 and 606 printed or otherwise applied onto substructure 602. Assembly 600 has the shape of a relatively thin strip member as opposed to a more rectangular, larger dimensioned pad assembly. For instance, while the strip assembly may have many different lengths, here, the strip assembly may have a width dimension suitable to accommodate a trace pattern 604, 606 that has a width dimension anywhere between one half an inch and five inches and, in particularly advantageous embodiments, that is within a range between one inch and two and one half inches.

Figure 31:
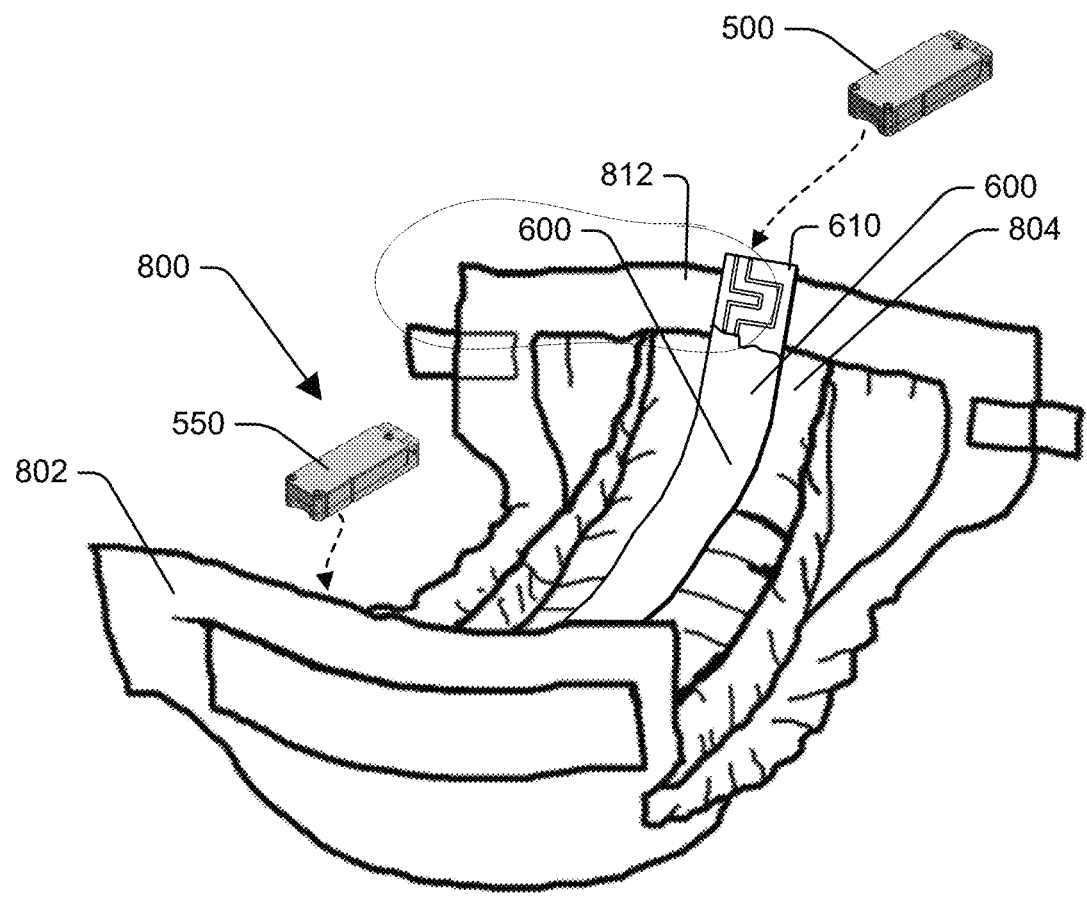
FIG. 31 is a perspective view of the sensor strip assembly of FIG. 30 installed on an inside surface of a diaper assembly.

With a width in one of these ranges, the sensor assembly 600 is suitable for use in applications where it is advantageous to detect wetness, blood, etc., in relatively smaller or constrained spaces or areas. For instance, a sensor assembly having a two inch width may be suitable for use within a diaper 800 as shown in FIG. 31. Diaper 800 includes an inner surface 804 and has a front end edge at 812 and a rear end edge at 802. Assembly 600 is placed on the inside surface 804 and extends from front edge 812 down the middle of the interior surface of the diaper toward rear edge 802. In some cases assembly 600 may extend from front to rear edges or may stop short of one or both of the front and the rear edges.

In at least some cases the lower surface of assembly 600 will be constructed of a material known to cause at least some friction with the fibers that constitute the inside surface 804 of diaper so that the pad assembly 600 will naturally stay in place once inserted into the diaper while a patient wears diaper 800.

In other cases, it is contemplated that adhesive strips 612 or even an entire adhesive layer may be applied to the rear side of sensor assembly 600 so that the assembly can be adhered to the inside diaper surface 804. In at least some cases to minimize cost as well as to ensure that the adhesive does not affect operation of the sensing mechanisms in the pad assembly, the adhesive may form strips that do not overlap the sensing traces 604 and 606 as shown in phantom at 612 in FIG. 30.

Referring again to FIG. 31, exemplary clip assemblies 500 and 550 are shown which, in at least some cases, clip to end edges (only edge 610 shown) of strip 600 just above the front edge 812 and rear edge 802 of the diaper. In some cases the ends of the strip 600 may extend up and out from the top edges of the diaper to be linked to the sensor clip arrangement. In other cases the ends of the sensor strip 600 may be located just below the diaper edges 812 and 802 and at least the lower portions of the clip assemblies may extend down between the upper portions of the diaper and the skin of a patient.

Figure 32:
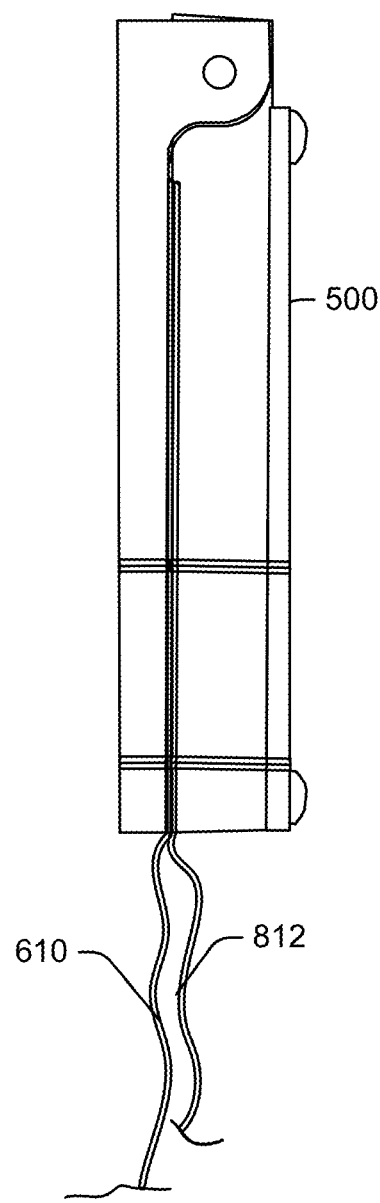
FIG. 32 is a side view of a clip assembly connected to an edge of a strip sensor assembly and a diaper for support.

In still other cases it is contemplated that the clip assemblies may clip on to the upper edges 812 and 802 of the diaper as well as the upper ends of the pad strip 600 with the contact pins extending through both the diaper and the sensing pad assembly as shown in FIG. 32. Here, the structure of the diaper can provide support for the clips reducing the possibility that the clips may rip the sensing assembly edges and render the sensor assembly non-functional or dysfunctional.

When the sensor clip is attached to a sensor assembly, the clip should be arranged so that the external surface of the housing is facing away from the patient's body in cases where there is an LED or other light indicator or an audible indicator located on the external housing surface side or that is viewable from that side.

While not shown, it is contemplated that a single clip arrangement akin to clip 533 shown in FIG. 28 may be employed in a diaper along with a sensor assembly that includes traces that terminate along the same edge of a strip pad so that a single resistive/sensing clip can be used with a diaper as opposed to two separate clips. Similarly, an integrated resistor akin to one of the resistors (e.g., 324) shown in FIG. 16 may be formed at trace ends opposite a single sensor clip to avoid having to use two clips in a diaper application.

In still other cases it is contemplated that a simplified resistor clip arrangement may be provided that is connected to trace ends prior to inserting a strip 600 in a diaper where the resistor clip then resides within the diaper completely once a patient puts the diaper on. Thus, the end resistance may be provided via a resistor that is integrated into a sensor assembly, by a clip that clips to ends of sensor assembly traces and is then located within a device (e.g., a diaper, a cast, a wound dressing, etc.) that is worn by a patient, or by a clip that clips to an end of the sensor assembly traces outside a device that is worn by a patient.

In some cases the strips 600 may come in predefined lengths and the sensor system may use information about those lengths/trace shapes and dimensions, to program sensing functionality. Thus, for instance, wetness location along a strip may be a function of length of the strip used to perform the sensing activity.

In other cases a roll of strip sensor material including continuous traces may be provided where an assistant rips off or otherwise cuts off a sensor strip in a required or desired length when needed. Thus, for instance, a care giver or assistant may cut off a 6 inch strip for one application and an 18 inch strip for a second application. In any of these cases, system clips can be attached to strip edges irrespective of strip length and initial impedance readings can be used to assess strip length and adjust operations accordingly.

Referring again to FIG. 30, in some cases a roll of strip material may include embossing 613 or indicia indicating where the roll should be cut at intervals when a strip is required and to ensure that trace ends at the ends of a ripped off strip are suitably arranged for use with sensor clips (e.g., so that the clip pins will contact the traces as required to ensure high quality contact needed for sensing). Here, for instance, where the roll of strip material has embossing every 6 inches, an assistant may rip off material strips of 6 inches, 12 inches, 18 inches, etc., in 6 inch intervals as needed for specific applications.

Referring again to FIG. 30, in at least some cases the strip substrate substructure 602 may include a layer structure akin to one of the layer structures described above with respect to FIGS. 2a and 2c so that sensor assembly 600 absorbs liquid in addition to sensing liquid, volume, liquid type (e.g., urine, blood, etc.). In other cases, the substructure 602 may be purposefully designed so that it is not absorbent so that liquid passes through the substructure. For instance, in the case of strip 600 in diaper 800 in FIG. 31, assembly 600 may not be absorbent so that the strip does not impede liquid from being absorbed by the diaper material. In still other cases the substructure 602 may be designed to absorb at least enough liquid to maintain a short between adjacent portions of the sensor traces so that once a short occurs at a specific location, the short persists at least for some time (e.g., at least a few hours until a diaper is changed).

Figure 33:
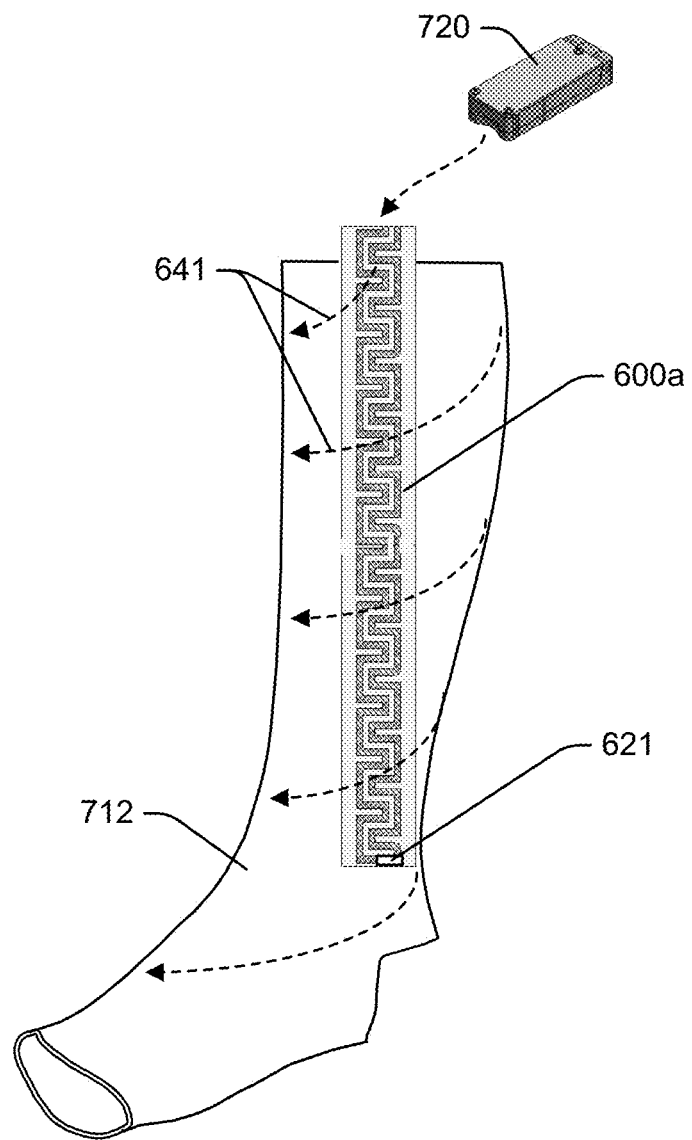
FIG. 33 is a perspective and partially schematic view of a strip type sensor assembly that may be included inside a leg cast for sensing wetness and other conditions that is consistent with at least some aspects of the present disclosure.

Referring now to FIG. 33, a strip type sensor assembly 600a is shown in a lower leg cast application. Here, it is contemplated that strip 600a may be located within a leg cast 712, extending along a substantial portion of an internal surface of the height of the cast 712 for sensing wetness, blood, etc., within the cast. Strip 600a in this embodiment includes an integrated resistor at 621 where the resistor resides within the cast once the cast is secured to a patient's leg. Here, the cast may be a wet cast or a two or three piece plastic boot type cast where Velcro or other type straps or other mechanical fasteners hold the cast pieces together about a patient's ankle.

To provide strip sensor 600a within cast 712, strip 600a may be adhered to or otherwise located adjacent a side of a patient's leg and the cast may be formed around the leg and strip or placed over the strip to hold the strip in place adjacent a patient's leg. In an alternative embodiment, strip sensor 600*a* may be adhered to or otherwise attached to the inside surface of one of the pieces of a two or three piece cast assembly and then the assembly may be fitted onto a patient's leg and strapped or otherwise held in place.

Figure 34:
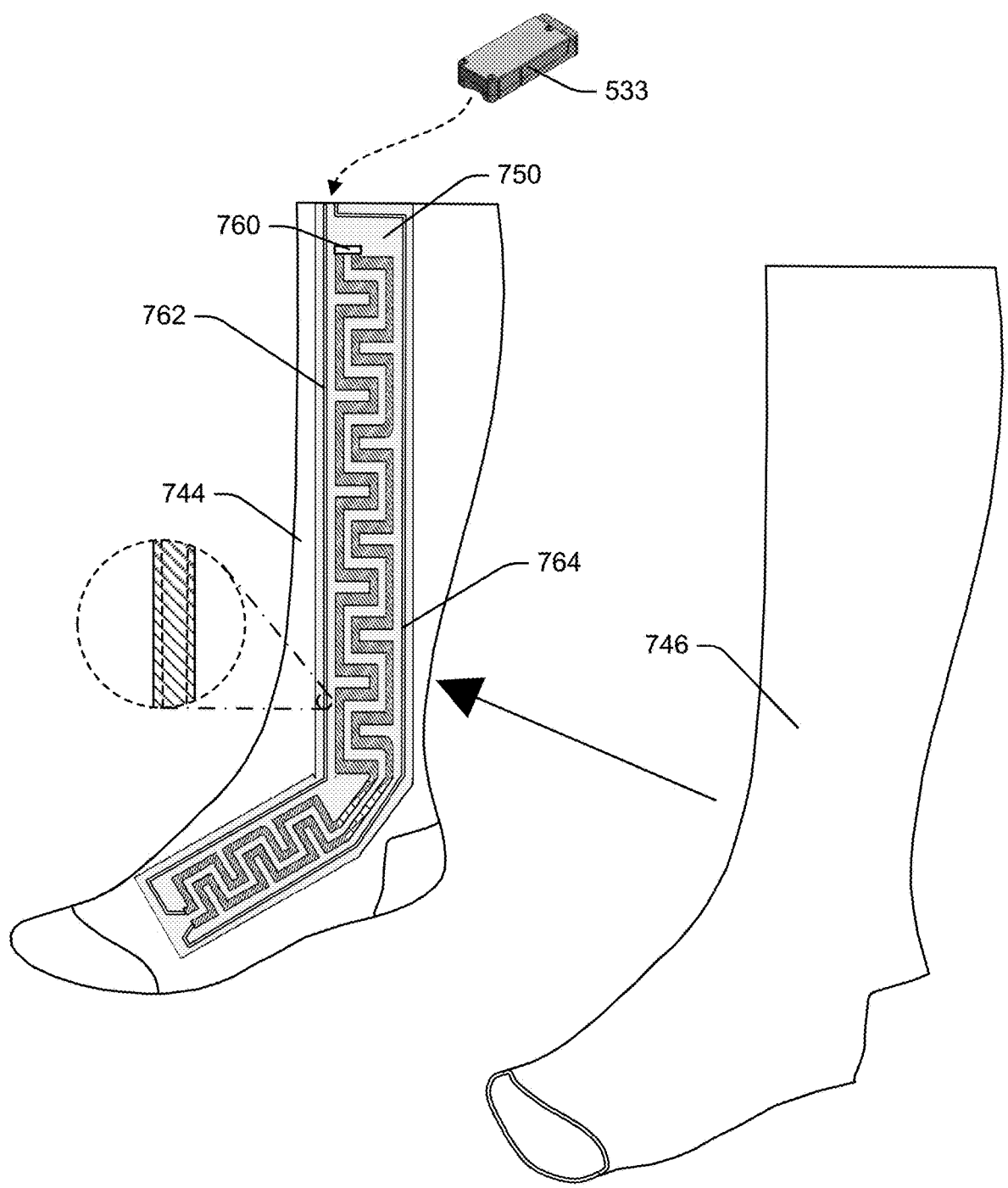
FIG. 34 is similar to FIG. 33, albeit showing a sensor assembly that has a different shape in a cast type application.

Referring to FIG. 34, in some cases, a sock 744 may be provided that is placed on the patient's leg prior to applying a rigid cast material 746 or components and a strip sensor pad 750 may be adhered or otherwise attached to an outer surface of the sock. In still other cases it is contemplated that sensor traces may be printed on the inside or outside surface of the sock 744 to embed or integrate the sensor traces into the sock itself. Here, because socks are usually fitted to only fit a wearer's foot/leg one way, when sensor traces are printed in a specific pattern on the sock and the sock is then put on a patient's leg, relatively precise locations of the trace pattern relative to anatomical portions of a patient's leg (e.g., bridge of foot, angle, shin, calf, etc.) can be known and then used to identify relatively precise locations at which wetness occurs on a patient's leg based on sensor readings in a fashion similar to that described above.

In some cases the strip 600*a* may be wrapped helically around a patient's leg as indicated by arrows 641. In other embodiments a strip sensor assembly 600*a* may extend down one side of a patient's calf, down below the patient's heel, and then up the other side of the patient's calf in a stirrup formation so that wetness can be attributed to one side or the other or both sides of a patient's leg within a cast. Other strip wrapping or application patterns are contemplated.

FIG. 33 shows an embodiment where any wetness that is close to the upper sensing end of the sensor assembly 600*a* that is detected effectively disables the system from detecting wetness that occurs at lower parts of assembly 600*a* because wetness at the upper end creates a short between adjacent trace portions so that condition at the other end of the assembly cannot be detected. FIG. 34 shows a different sensor trace pattern where traces 762 and 764 extend from an upper end of a pad assembly 750 where clip attachment is relative easy down to a lower end and then the dual trace sensing pattern extends upward as illustrated to a resistive end element 760 near the upper end of the pad assembly 750. The FIG. 34 pattern enables detection of the lowermost location at which wetness occurs within the cast 746 irrespective of wetness there above while still enabling sensor clip attachment at the top end of the cast for convenience.

In still other cases it is contemplated that a cast pad assembly and clip assembly akin to those described above with respect to FIGS. 14 and 15 may be provided and controlled so that resistance and potential are switched between different ends of pad traces so that upper and lower limits of wetness within a cast can be detected in a manner similar to that described above with respect to FIG. 14.

While one strip assembly 600*a* is shown in FIG. 33, in other embodiments two or more strips may be placed within a cast. For instance, in some cases strip 600*a* extending downward along an inside of a patient's calf may be a first strip and a second strip (not illustrated) may be positioned to extend downward along an outside of the patient's calf.

Figure 35:
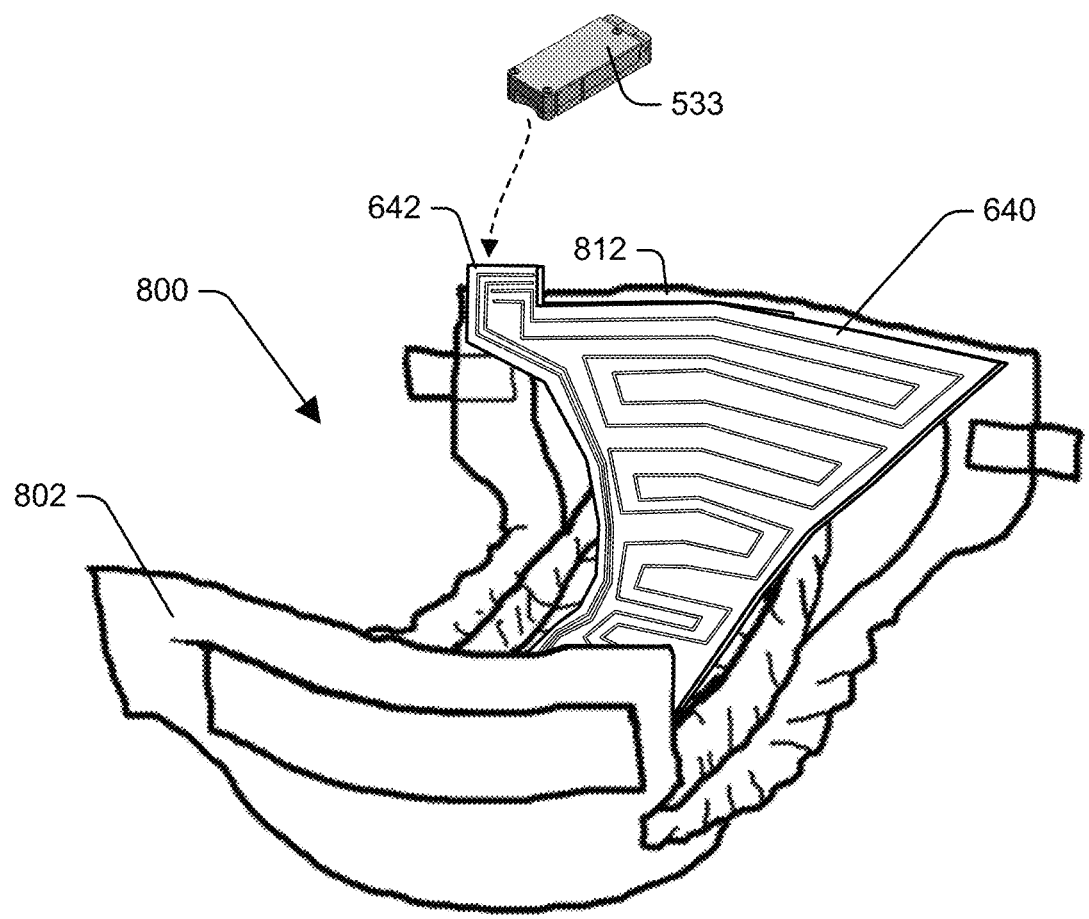
FIG. 35 is similar to FIG. 31, albeit showing a different sensor assembly installed on an inside surface of a diaper.

While square, rectangular and strip shaped sensor pads are contemplated and may be provided for advantageous use in many applications, it has been recognized that many other trace patterns can be printed or otherwise formed on a pad substrate assembly where the other patterns are even better suited to some applications. For instance, in a diaper application, in at least some cases it may be advantageous to provide a sensor pad assembly better shaped to account for an "average" or "standard" human shape or so that the location of a sensor clip can be located to a patients side as opposed to in near the patient's back or belly area. To this end, see for instance FIG. 35 that shows an hourglass shaped diaper pad sensor assembly 640 that is wide near the front and rear portions of an adjacent diaper where wetness may occur. A tab 642 for connecting a single clip resistive/sensor assembly 533 extends from an upper diaper edge near a side portion of the diaper. Tab 642 extends from an upper edge 812 of the diaper to attach clip 533. Once clip 533 is attached to a diaper that is being worn, the clip is located adjacent the patient's side. The pad shape better covers portions of the diaper that typically experience wetness than would a strip type pad.

Figure 36:
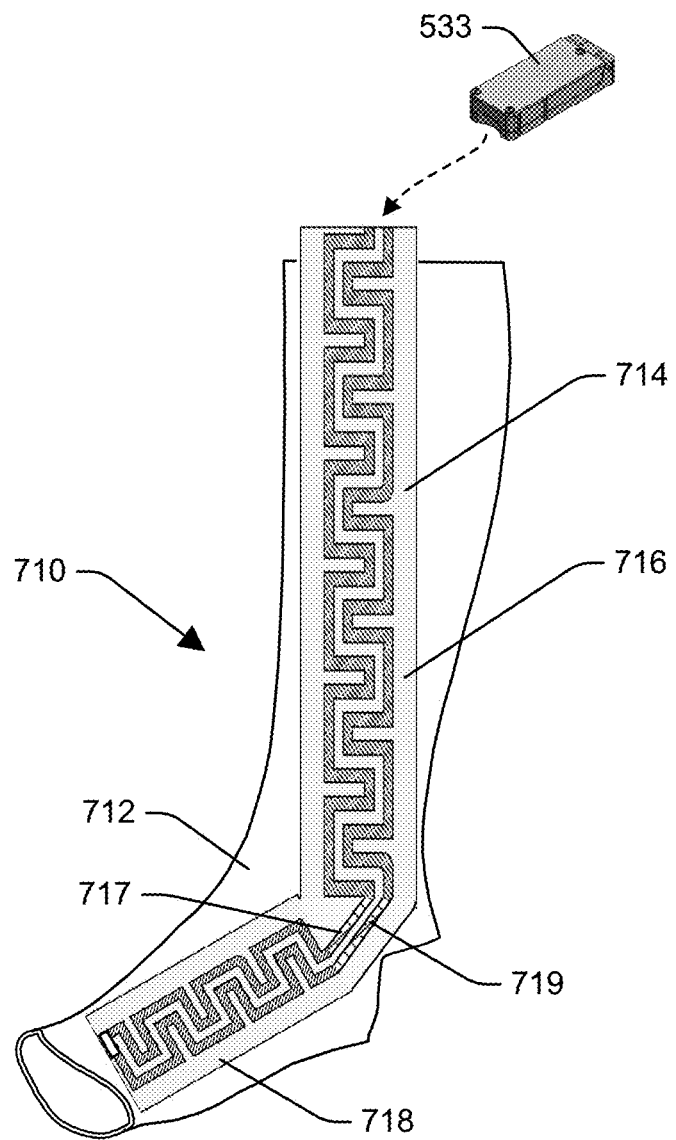
FIG. 36 is similar to FIG. 34, albeit showing a sensor assembly that includes a resistive element that is located within a cast cavity.

Referring now to FIG. 36, another cast arrangement 710 including a strip pad sensor that is consistent with at least some aspects of the present disclosure is illustrated where the pad assembly 714 has an L-shape that at least roughly mirrors the anatomical shape of a typical patient's foot and calf. As shown, when applied or positioned adjacent a patient's foot and calf, a lower portion 718 of the assembly is positioned adjacent the patient's foot and the upper power 716 is positioned adjacent the patient's calf with an upper end extending from an upper edge of the cast for connection to a sensor clip 533.

The L shape enables wetness sensing within the cast and also may facilitate assessment of where along anatomical portions of a patient's body wetness is occurring. For example, in a case where a patient was treated for a calf lesion prior to applying a cast, wetness adjacent the calf would have different medical implications than wetness along the underside of the patient's foot absent wetness at the calf location. In these cases, the resistive value detected by sensor clip 533 could be used to determine if wetness occurs along the patient's calf or along the patient's foot so that an assistant can identify appropriate treatment activities. Thus, for instance, a first detected resistive value may indicate that wetness occurs along the patient's foot and a second value may indicate that wetness occurs along the patient's calf.

In at least some cases the traces may have different resistivity along different portions of their lengths. For instance, in some cases extremely low resistance trace sections may be provided along at least sections of traces for passing current with greater impedance along other trace sections that are provided for wetness detection. For example, in FIG. 36 trace portions 717 and 719 may be printed to conduct with little resistance while other sections of the traces illustrated have higher resistance.

In other cases, referring again to FIG. 36, resistivity along central portions of the traces at 717 and 719 may be greater than along other portions of the traces so that, when wetness is detected along foot portion 718, the resistive value detected is substantially different than when wetness occurs along calf portion 716. Instead of both sections 717 and 719 being higher resistance, one or the other of sections 717 and 719 may be higher resistance than other trace sections. Additional high resistance portions are contemplated that could divide the traces and portions of the sensor assembly into three, four or more differently identifiable parts of the sensor assembly 714. Different trace portion resistivity may be the result of printing different ink compositions, printing traces with different cross sectional dimensions (e.g., width, depth, or both), or both printing with different ink compositions and different dimensions.

In some cases it may be that at least sections of sensor traces are electrically insulated so that no liquid short can occur between those trace sections and other trace sections.

For instance, see again FIG. 34 that includes traces with straight sections 762 and 764 as well as sections that have a serpentine sensor pattern between lower ends of straight sections 762 and 764 and resistive element 760 at the upper end of sensor assembly 750. In at least some embodiments the straight sections 762 and 764 may be electrically insulated while the serpentine sections are not electrically insulated.

Figure 37:
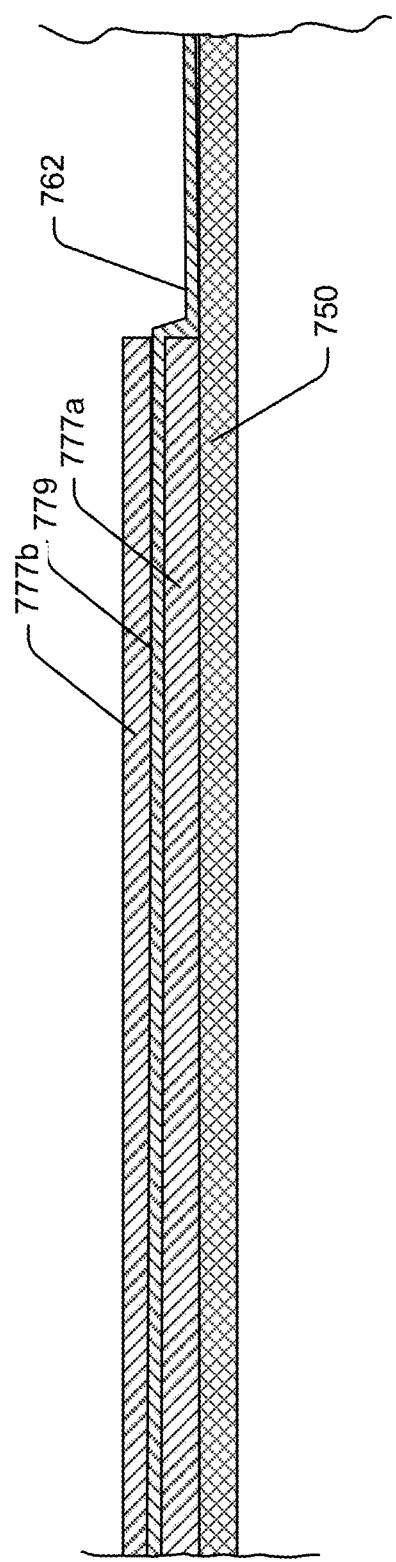
FIG. 37 is a cross sectional view of a sensor assembly including a trace having a first section that is encased in an insulating print structure and a second section that is exposed and not electrically insulated.

Referring also to FIG. 37, to insulate a trace section 762 it is contemplated that an electrical insulating ink composition 777a, 777b may be printed on substrate substructure 750 in a manner that encases a conducting ink layer 779. For instance, insulating material ink layer 777a may be printed on substrate substructure 750 first that has a pattern that is similar to the pattern of an electrically conductive trace section 762 that is to be printed on top of the insulating ink layer, albeit where the insulating layer 777a is wider than the conductive trace to be printed thereon. Once the first insulating layer 777a is printed on substrate substructure 750, the conductive trace section 779 is then printed on top of the insulating layer and then a second insulating layer 777b is printed on top of the conductive trace section 779 to completely encase the conductive section within insulation. In FIG. 37, a portion of trace 762 is shown encased in insulating layers 777a and 777b and a second portion of the trace 762 is shown exposed.

Insulated trace sections may be near the ends of the traces or along trace sections that are spaced from the trace ends. In at least some cases two, three or a different number of insulating trace sections may be separated by exposed sections to form different sensing and non-sensing patterns.

In at least some embodiments it is contemplated that distinct sensor sections may be formed where sensing applications optimally require wetness location determination at a small set of different and spaced apart locations. To this end, see for instance FIG. 38 where a sensor assembly 900 includes first and second sensor subassemblies 902 and 904 that are linked together via a bridging substructure 906. First sensor subassembly 902 includes a first substrate substructure 911 and first and second traces 908 and 910 that form a serpentine trace pattern consistent with the disclosure described above. The first substrate substructure 911 may, in at least some cases, be formed via a layering structure as described above including materials that have absorptive capacity or that are not absorptive. First ends of the traces 908 and 910 are located along a top edge of the substructure 911 to be attached to a sensing clip 500 as illustrated.

Figure 38:
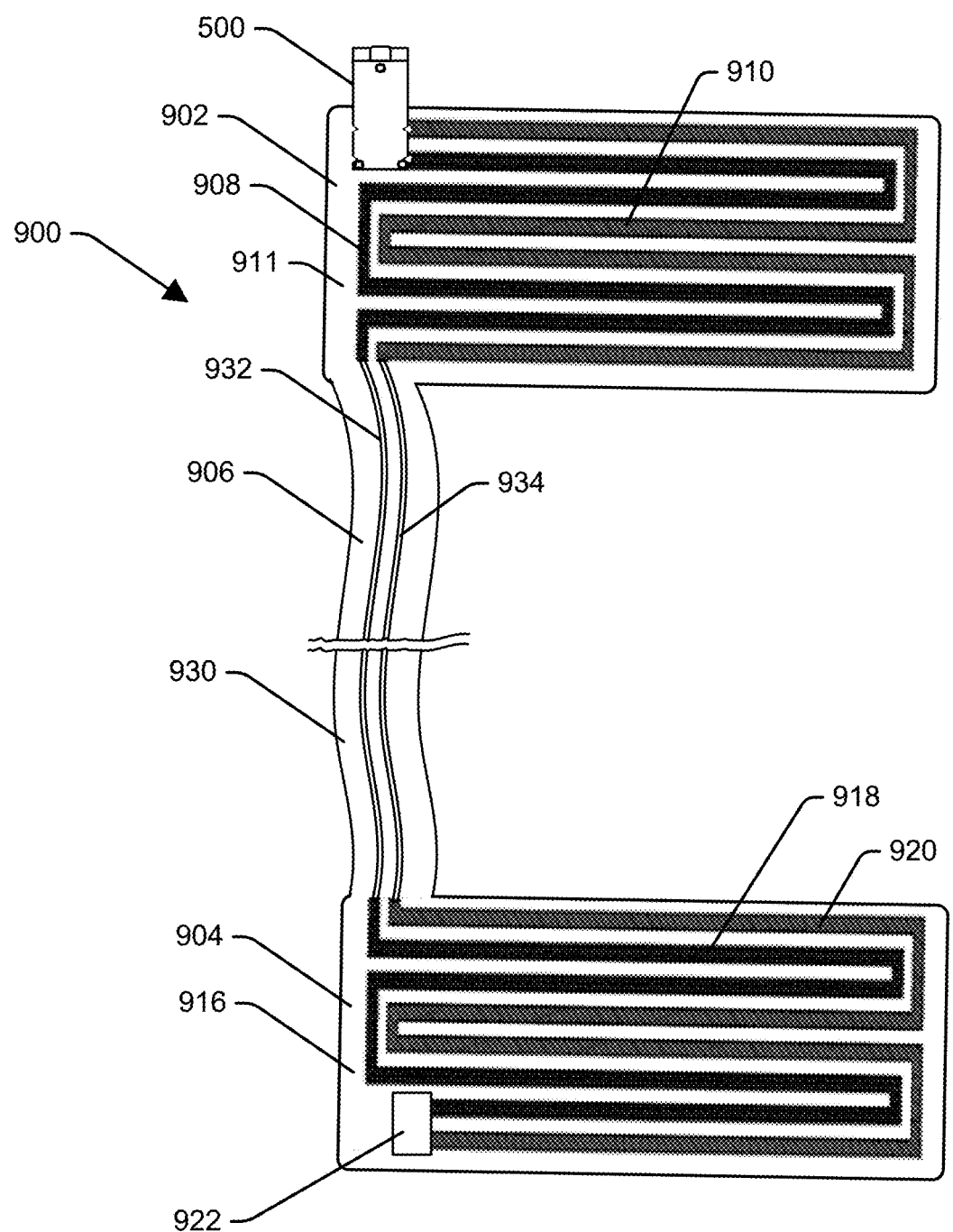
FIG. 38 is a plan view of a dual sensor assembly that is consistent with at least some aspects of the present disclosure.

Referring still to FIG. 38, second sensor subassembly 904 includes a second substrate substructure 916 and first and second traces 918 and 920 that form a serpentine trace pattern consistent with the disclosure described above. Second substrate substructure 916 may, in at least some cases, also be formed via a layering structure as described above including materials that have absorptive capacity or that are not absorptive. Second ends of the traces 918 and 920 are located adjacent a bottom edge of the substructure 916 and are linked via a resistive component 922 that, in at least some cases, is a relatively high resistance printed layer or member.

Bridge subassembly 906 includes a substrate substructure 930 that is strip shaped and extends from an edge of substrate substructure 911 to substructure 916. In at least some cases substructure 930 will include a layered assembly that is akin to the layered substructures 911 and 916 and, in that regard, the three substructures may simply be formed via the same laminated layer set, albeit cut out to form the dual sensor and bridge shape as shown. In other cases substructure 930 may include some of the layers that are included in substructures 911 and 916 but not others. For instance, while substructures 911 and 916 may each including absorptive material layers, substructure 930 may not.

Referring still to FIG. 38, bridge subassembly 906 also includes first and second conductive traces 932 and 934 printed on a surface of substructure 930 where conductive trace 932 connects a second end of trace 908 from the first sensor subassembly 902 with an end of trace 918 opposite resistive element 922 and where trace 934 connects a second end of trace 910 from the first sensor subassembly 902 with an end of trace 920 opposite resistive element 922. In at least some cases traces 932 and 934 may be insulated and formed via the three step printing process described above. As in other embodiments, in at least some embodiments adhesive may be applied to a side of assembly 900 for securing the sensor subassemblies 902 and 904 as well as bridge assembly 906 to a supporting structure (e.g., a patient's body, a diaper, a garment worn by a patient, etc.

In use, the FIG. 38 sensor assembly 900 may be arranges with sensor subassemblies 902 and 904 at locations at which wetness it to be detected and a clip 500 may be attached for sensing purposes. Based on a detected resistive value between the non-insulated traces, a process is able to assess if wetness occurs and if so, if it occurs near the first or second sensor subassemblies. While an assembly with two separate sensor subassemblies is illustrated, assemblies with three or more sensor subassemblies that are daisy chained together via intervening bridge subassemblies are contemplated.

Figure 39:
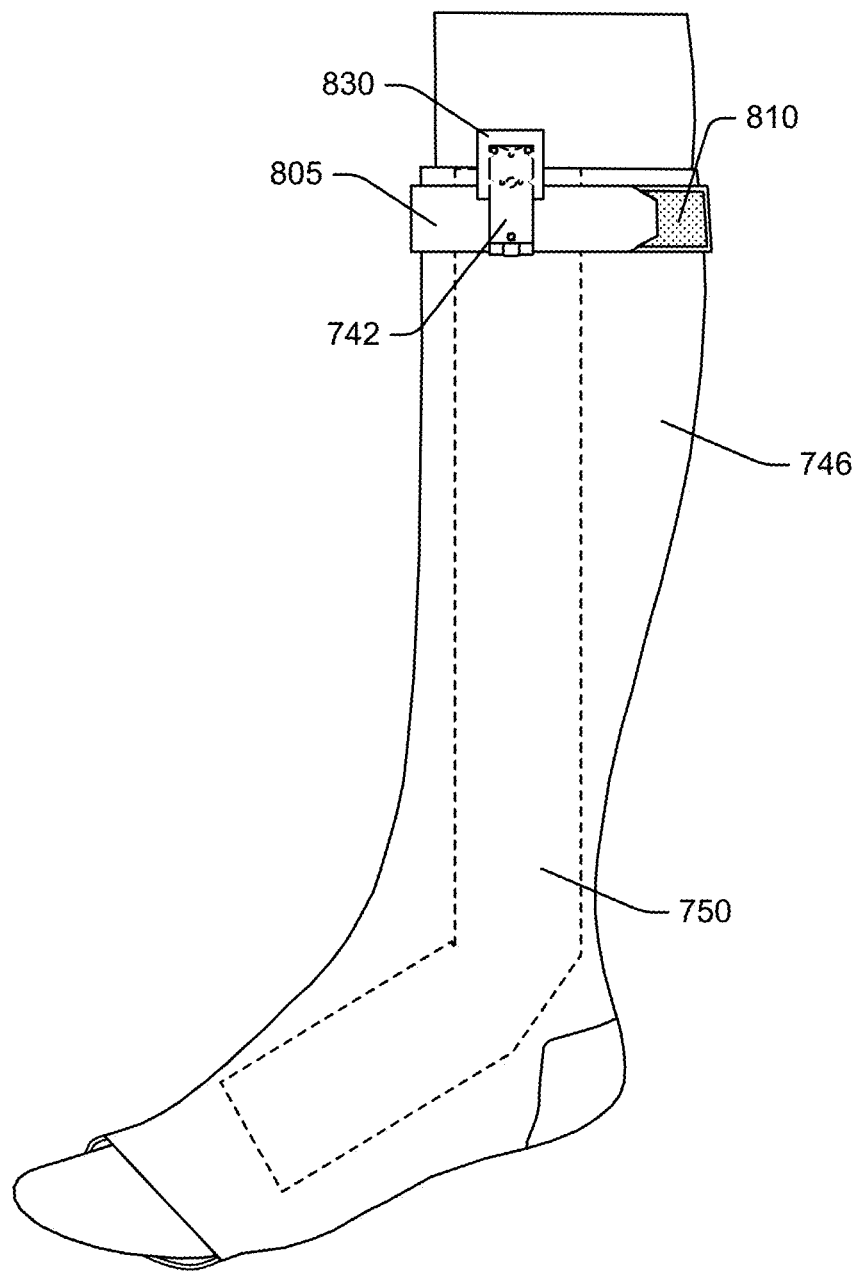
FIG. 39 is a perspective view of a sensor assembly in a cast application with a belt member attached to the cast to support a sensing clip assembly.

In the case of a leg cast, while a sensor assembly may extend from an upper edge of the cast for connecting a sensor clip assembly, in some case it may be advantageous to provide some type of additional support structure for the clip so that the clip does not tear or otherwise damage the upper end of the sensor assembly. For instance, see FIG. 39 where a band 805 is shown that wraps around an outer surface of a cast 746 near the upper edge thereof. In some cases, band 805 may include a Velcro coupling mechanism 810 or some other mechanical coupler that can be used to lock the band in place. In the illustrated example, a sensor clip 533 is illustrated that is attached to the band where the clip gap 515 (see gain FIG. 27) opens upward and where an upper end 830 of the strip pad extends out from the cast and bends over to be received within the gap 515. Here, sensor clip 533 may attach to the band via any type of mechanical fastener including a dedicated fastening clip, Velcro, etc.

Figure 40:
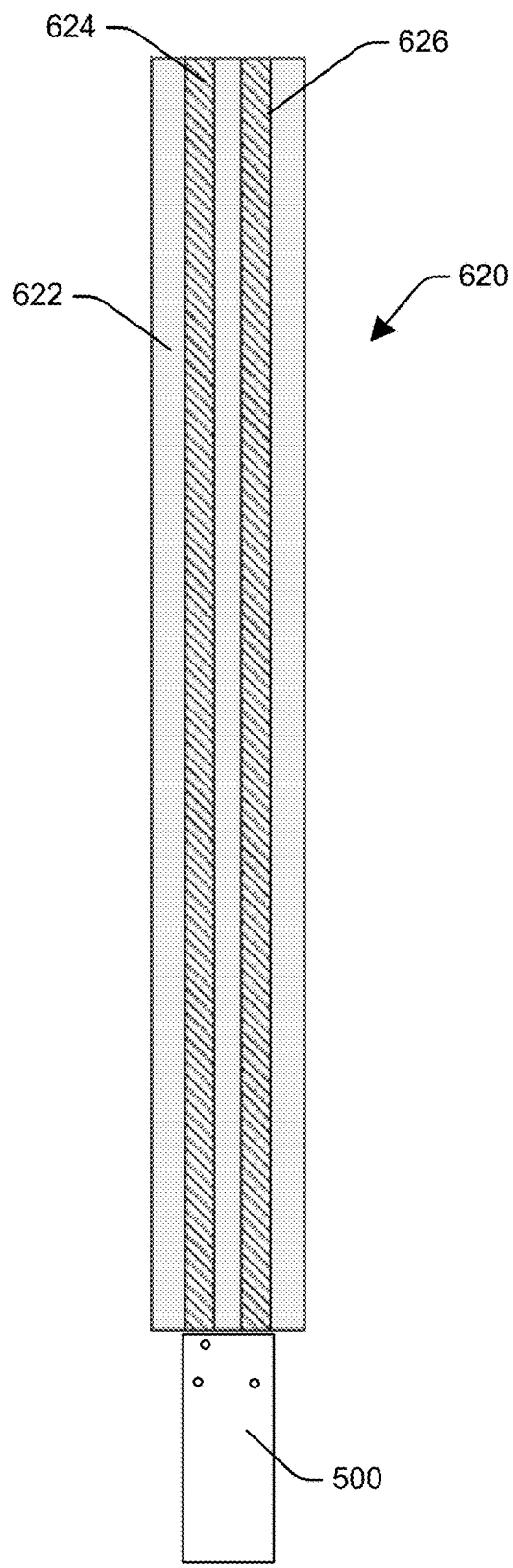
FIG. 40 is a top view of another strip sensor assembly with a different trace pattern.
Figure 41:
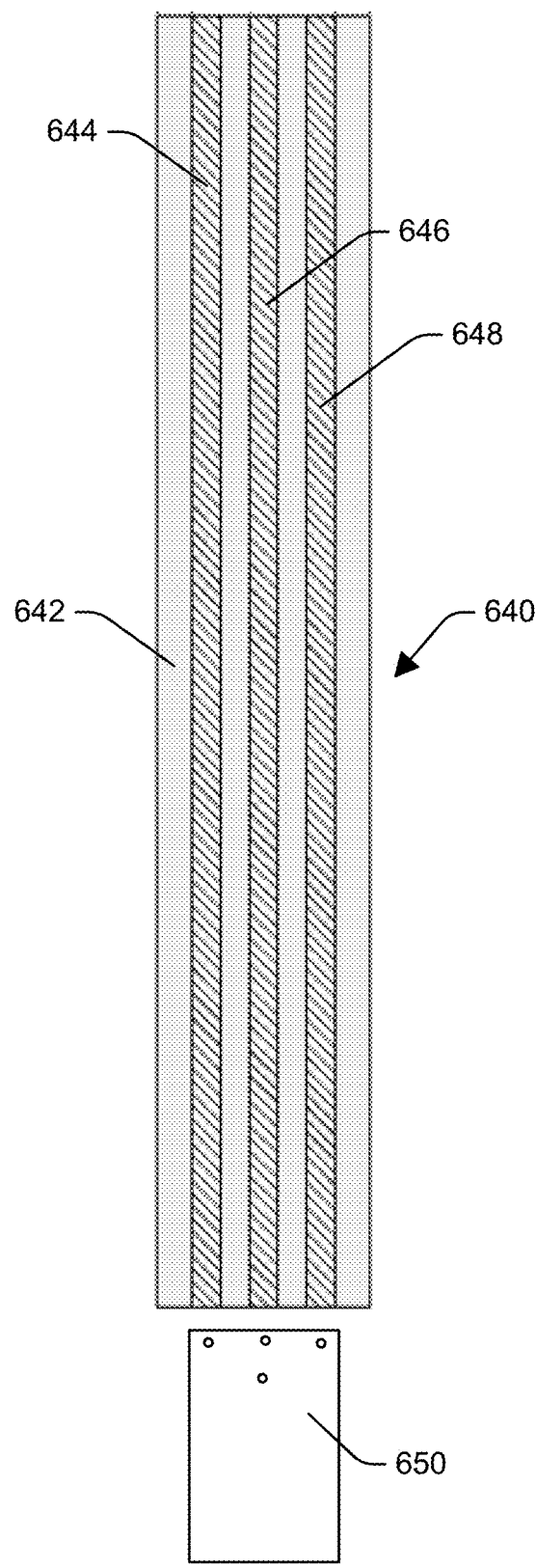
FIG. 41 is a top view of another strip sensor assembly with a different trace pattern.

Other strip assembly trace patterns are contemplated. For instance, see FIG. 40 where a strip assembly 620 includes linear, parallel traces 624 and 626 printed on a substrate substructure 622 where the traces extend the entire length of substructure 622. See also FIG. 41 where a strip assembly 640 includes three linear and parallel traces 644, 646 and 648 that extend between ends of a substrate substructure 642. In FIG. 41, a sensor clip 650 has a different pin arrangement that is designed to connect to all three traces and the clip processor would be programmed to use signals from all the pins to detect wetness and generate data useable to assess wetness, volume, liquid type, etc.

While most of the sensor assemblies described above include traces printed on assemblies that include absorptive padding or substructure of some type, in at least some applications, sensor device absorption is not required and, for that reason, in at least some cases a sensor assembly may include resistive traces printed on non-absorptive substrates. For instance, in the cast applications described above, in at least some cases absorption is not required and in those cases the assembly substrates may be essentially non-absorptive. As another instance, in a diaper application, most diapers are equipped with liquid absorption capabilities and in those cases the sensor assembly may include a non-absorptive substrate.

In at least some cases it is contemplated that instead of absorbing liquid, a substrate may be purposefully designed to provide no barrier or minimal liquid barrier so that wetness can pass through the substrate and to other product features designed to deal with liquid. Here, the substrate is said to be "breathable" as it is designed to pass air and liquid. Again, in a diaper application, there is no reason for absorption and instead liquid should be passed through an assembly substrate to the absorbing layers that are provided within the diaper itself. In a cast application there may be mechanical features (e.g., a sock, cotton batting layer, etc.) that are designed to dissipate minimal wetness and in those cases sensor pad absorption may not be desired or, perhaps, the pad will be designed to absorb somewhat for wetness sensing purposes but to pass excessive liquid in a breathable fashion.

In addition to being configured to be used as an insert of a liner strip or the like, in at least some applications it is contemplated that a strip type sensor assembly may be configured as a disposable wrap that includes an embedded sensor where the wrap allows moisture to penetrate through for wound care. Here, for instance, the wrap may be cut to any length and be placed over a wound or wrapped around a part of a patient's body to cover the wound in a manner akin to the way an ace bandage is wrapped around a sprained ankle, wrist, or the like. Again, in this case, the wrap may come as a roll of sensor material including traces printed on a substrate subassembly where an assistant can cut off pieces of the roll to desired lengths.

While the embodiments described above generally include disposable sensor pads and inserts that include printed sensor traces, in other cases it is contemplated that reusable sensor assemblies may be constructed using similar printed trace sensor arrangements. For instance, a washable bed pad including one or more washable and absorbing fabric layers may be constructed where sensor traces are printed or otherwise located within the fabric laminate construction. Here, in some embodiments the pad structure will include a liquid impermeable bottom layer to avoid a case where urine or other liquid penetrate the pad and run into a bed mattress or the like. In at least some cases it is contemplated that patients will not want to reuse washed sensor pads for incontinence but may be more open to use of these types of pads in other contexts like, for instance, wound care, sweating, etc. Thus, these types of reusable and washable pad assemblies, while useful in most applications, may be restricted to use in applications other than those related to patient voiding activity.

In at least some embodiments, as data is collected on a patient's voiding schedule, that information is used to predict future voiding activities and a system processor is programmed to generate alert signals so that a patient or an assistant can arrange for the patient to use a restroom or a bed pan if possible prior to a voiding event causing a mess. To this end, in at least some cases the server 28 shown in FIG. 1 may run a program that captures multiple day voiding activity for a specific patient and that learns, to the extent possible, the patient's voiding schedule. In some case the multiple day tracking will track a period ranging from two days to fourteen days and in other cases the period may be within a range of three to seven days.

In particularly advantageous embodiments the day tracking period will start immediately when the wetness tracking system is initially used with a patient so that any wetness tracking data that is generated is used to generate most accurate future wetness predictions possible. Then, once patient wetness data has been generated for a maximum tracking period, the tracking period will roll forward. For instance, assume a first patient is admitted to a hospital on day 1 and the wetness tracking system is used with the first patient starting on day 1 to generate a voiding schedule where the patient voids every 3 hours. During the second day, while the wetness tracking system continues to track voiding schedule, the system may also use the day 1 voiding schedule to generate predicted void event alerts 15 minutes prior to the 3 hour predicted void times. Over the next few days, as more wetness/voiding data is obtained, the software continually updates the predictive voiding schedule to be more accurate. In at least some cases a maximum tracking period will be 7 days. In these cases, the process of fine tuning the voiding schedule continues until 7 days of wetness/voiding data has been generated. In the event that the wetness tracking system is used with the first patient for more than 7 days, the data used to develop the voiding schedule rolls forward and includes the most recent 7 days of data.

As predicted void alerts are presented to a patient and/or assistant and the patient uses a toilet or bed pan to void instead of wetting a bed or a diaper, wetting events should occur less frequently. Here, if the server is programmed to adjust the voiding schedule based on detected wetting events alone, the predictive schedule would become inaccurate in a short duration of time. For this reason, in at least some cases it is contemplated that a patient and/or assistant will be responsible for indicating when a patient voids in a toilet or a bed pan so that that information can be used to update a predicted void schedule for a patient. Thus, for instance, an assistant that receives a predicted void alert for a first patient and then helps the patient to use a toilet may use her tablet or other portable computing device 16 (see again FIG. 1) to indicate the time when the controlled void occurred.

In other cases once a predicted void alert is generated, the system may require an assistant or patient to acknowledge the alert and may, based on that acknowledgement, automatically presume that a void occurred (e.g., that the patient responded to the alert by using a toilet or a bed pad. Here, acknowledgement may be via a portable computing device or the like.

In still other cases, after an alert is acknowledged, the system may require a separate confirmation that a patient associated with the alert actually voided. For instance, once an assistant acknowledges a predicted void alert for a first patient, if the assistant has not confirmed a void within 15 minutes, the system may automatically request confirmation as a second follow-up alert.

In some cases the predictive wetness software program may access other medical records information and use that information to increase void prediction accuracy. For instance, a first patient may routinely void two hour after she falls asleep. Here, if a patient monitoring system detects patient sleep state, the time at which the first patient enters a sleep state can be used along with the predictive void information to generate an alert. Other information that may be used as alert triggers includes detected or recorded liquid consumption, medication consumption, procedure types and times, food consumption, etc.

In some cases the system may triage the alerting process. To this end, where a patient and an assistant each uses and has access to a portable computing device, the server may automatically send a first predicted void message to the patient to encourage the patient to go to a restroom to void. In cases where a TV or other display screen including Bluetooth, WiFi, or other wireless capabilities is present in a patient's room, an alert may be presented to the patient via that device. If the patient does not acknowledge that a void occurred within a threshold period of time (e.g., 10 minutes), the system may automatically generate and present a second alert to an assistant The system may also be programmed to track if a patient is capable of going to a restroom or using a bed pan herself or if she needs assistance and may adjust alerts accordingly. For instance, in a case where four alerts for four consecutive predicted voids are first sent to a patient and then to an assistant if the patient does not confirm voids, the system may automatically determine that the patient is incapable of responding to the alerts and, for future alerts, may only send those to the assistant.

In some cases in addition to indicating a wet state, an alert will also include other wetness characterizing information that an assistant can use to assess how best to respond to a patient's condition. For instance, an alert may indicate a wetness volume or degree of absorbing pad saturation (e.g., "damp", "wet", "wetter", "soaked" or "extremely wet").

As another instance, an alert may indicate liquid type(s) associated with a wet condition. For example, is the liquid detected urine, sweat, blood, or some unknown liquid? As another instance, the alert may indicate where on the area of a sensor pad assembly wetness has occurred. For example, is the wetness in the middle of a large bed pad or near a pad edge. As another example, in the case of a strip sensor assembly used in a cast, an alert may indicate where along the length of the sensor assembly wetness occurred (e.g., two inches from a first end, at a second end, etc.).

As yet one other instance, where a sensor assembly has different portions adjacent different parts of a patient's body, an alert may indicate which part of the patient's body is adjacent a wet spot. For example, in the case of a cast that wraps a patient's foot and calf, an alert may indicate that a wet spot is detected on the inside of a patient's calf.

In some cases it is contemplated that an assistant may be able to affirmatively ignore an alert. For instance, in the case of a cast where slight wetness occurs adjacent an underside of a patient's foot as opposed to near a calf lesion, an assistant may select an option to ignore an associated alert. Here, the sensor system in at least some embodiments would continue to monitor for exacerbated wetness or wetness at the patient's calf or adjacent other anatomical areas of the patient's leg and would generate other alerts at later times when conditions change. Here, when an assistant ignores an alert, if an alert was being provided to a patient, that alert may be halted.

In some cases specific alert types may not be able to be ignored. For instance, a soaked wetness condition at a calf area where a calf lesion was treated may not be ignorable and may require an assistant to be present at a patient's location to disable the alert.

As still one other instance, where a portion of a sensor assembly is adjacent an inflicted part of a patient's body, an alert may indicate that wetness is adjacent the inflicted body part. For example, an alert may indicate "A substantial amount of blood has been detected adjacent patent A's left calf wound." Many other alert types are contemplated.

In some cases where a sensor pad or additional affordances have absorption capabilities and where the system is programmed to assess saturation levels, the system may be programmed to only generate alerts when pre-defined saturation levels or other void parameters are met. For instance, in some cases when a sensor pad assembly is only damp as the assembly has absorbed a minimal amount of urine, the system may not generate an alert. Once the assembly is at least somewhat saturated, the system may then generate an assistant alert.

In some cases assistants and even patients may subscribe to alerts and, effectively, select alerts that meet certain criteria so that assistants are not inundated with trivial notifications of conditions insufficient to warrant a care activity. For instance, while a system server may track and record all liquid detection events, an assistant may not want to be notified when a patient that is using a wetness absorption affordance (e.g., a diaper, bed pad, etc.) is only damp as that condition typically does not pose a substantial health risk. In this case, the assistant may opt, via an interface provided on a portable computing device 16 (see again FIG. 1), to only receive liquid detection alerts when detected wetness is above some threshold level (e.g., substantially saturated). Where the system tracks wetness on a 1-10 range (10 being complete saturation), assistants may select wetness conditions that warrant alerts for each separate patient based on a 1-10 range.

An exemplary but incomplete list of alert types that the system may generate include the following:
(1) Sensor is operating properly;
(2) Sensor is disconnected;
(3) Sensor is correctly connected;
(4) Sensor battery is low;
(5) Specific volumes (e.g., 200 ml) of urine on the pad;
(6) Pad is dry;
(7) Pad is wet (or different degrees of wetness (e.g., damp, wet, wetter, soaked, extremely wet);
(8) Location of wetness on pad;
(9) Wetness near pad edge;
(10) Void event occurred;
(11) Liquid type (e.g., urine; sweat; water; blood, etc.);
(12) X minutes to anticipated void time;
(13) Now is an anticipated void time;
(14) Assistant will be here shortly;
(15) Assistant has been alerted;
(16) Assistant has confirmed alert state;
(17) X minutes since last void time;
(18) Wetness increased X minutes ago;
(19) Initial wetness detected X minutes ago;
(20) Etc.

In some cases the system will automatically generate a facility map and indicate real-time wetness sensor assembly status for each patient in a facility on the map. To this end, see, for instance FIG. 42 that shows a simple facility map representation 950 provided on the display screen of an assistant's portable tablet device 16. The map representation includes a representation of each patient room in the facility. While not shown, specific patient names may be associated with each of the rooms and represented on the map. In other cases, for privacy reasons, patient names may not be included on the map. Rooms on the map where a current patient wet condition has been detected are shown cross hatched and, in the example, include rooms labelled 952, 954, 956, 958 and 960. Rooms 952, 956 and 960 that are single cross hatched may indicate a damp condition (e.g., minimum wetness) while rooms 954 and 958 that are double cross hatched indicate an extremely wet condition (e.g., maximum wetness). The different wetness states may be presented via different colors (e.g., yellow for damp, red for soaked, etc.). In some embodiments the map will be able to indicate five or more distinct wetness states via different colors. The wetness map is updated at periodic intervals (e.g., every 10 seconds). In some cases, the duration of the updating interval may be selectable by an assistant.

In some cases the map will also be controlled to indicate the states of issued predicted void event alerts. For example, in FIG. 42, an alarm icon 970 is spatially associated with room representation 952 and includes a "1" indicator which indicates that a predicted void event alert has been presented to the patient in room 952 but not to an assistant. Here, per the cross hatching on room 952, the patient is already damp. Similarly, an alarm icon 974 spatially associated with room representation 972 that also includes a "1" indicator indicates that a predicted void event alert has been presented to the patient in room 972 and not to an assistant. Here, because room 972 is not cross hatched, the wetness sensor in that room has yet to detect a wet state.

Figure 42:
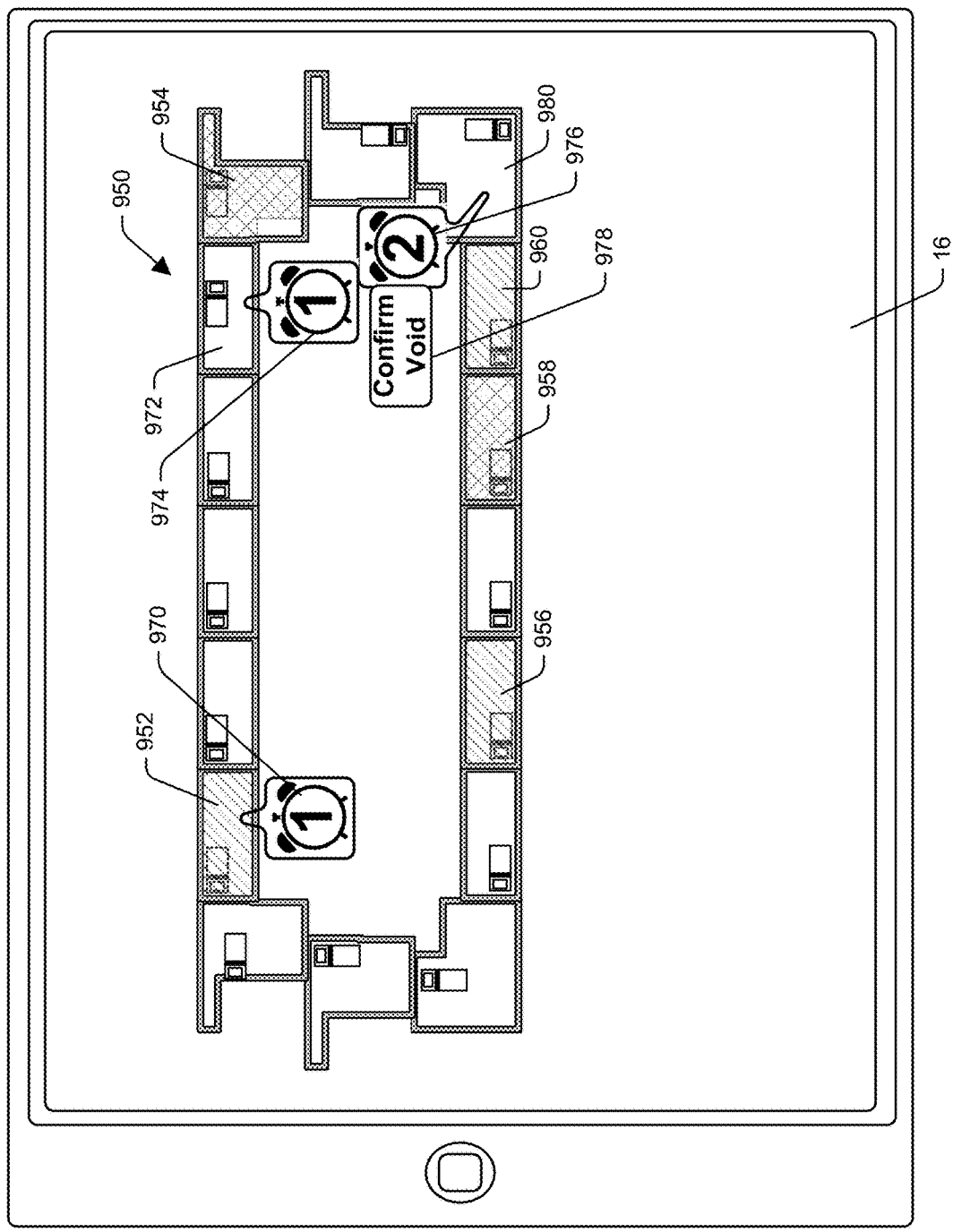
FIG. 42 shows a portable computing device presenting a facility map that shows wetness states that is consistent with at least some aspects of the present disclosure.

Referring still to FIG. 42, an alarm icon 976 is spatially associated with room representation 980 and includes a "2" indicator which indicates that a predicted void event alert has been presented to an assistant responsible for the patient in room 980. Here, because there is no cross hatching on room 980, the patient in that room is still dry. A "Confirm Void" icon is also presented at 978 which is spatially associated with alert icon 976 and which can be selected by an assistant to confirm when the patient in room 980 has successfully completed a voiding event.

Figure 43:
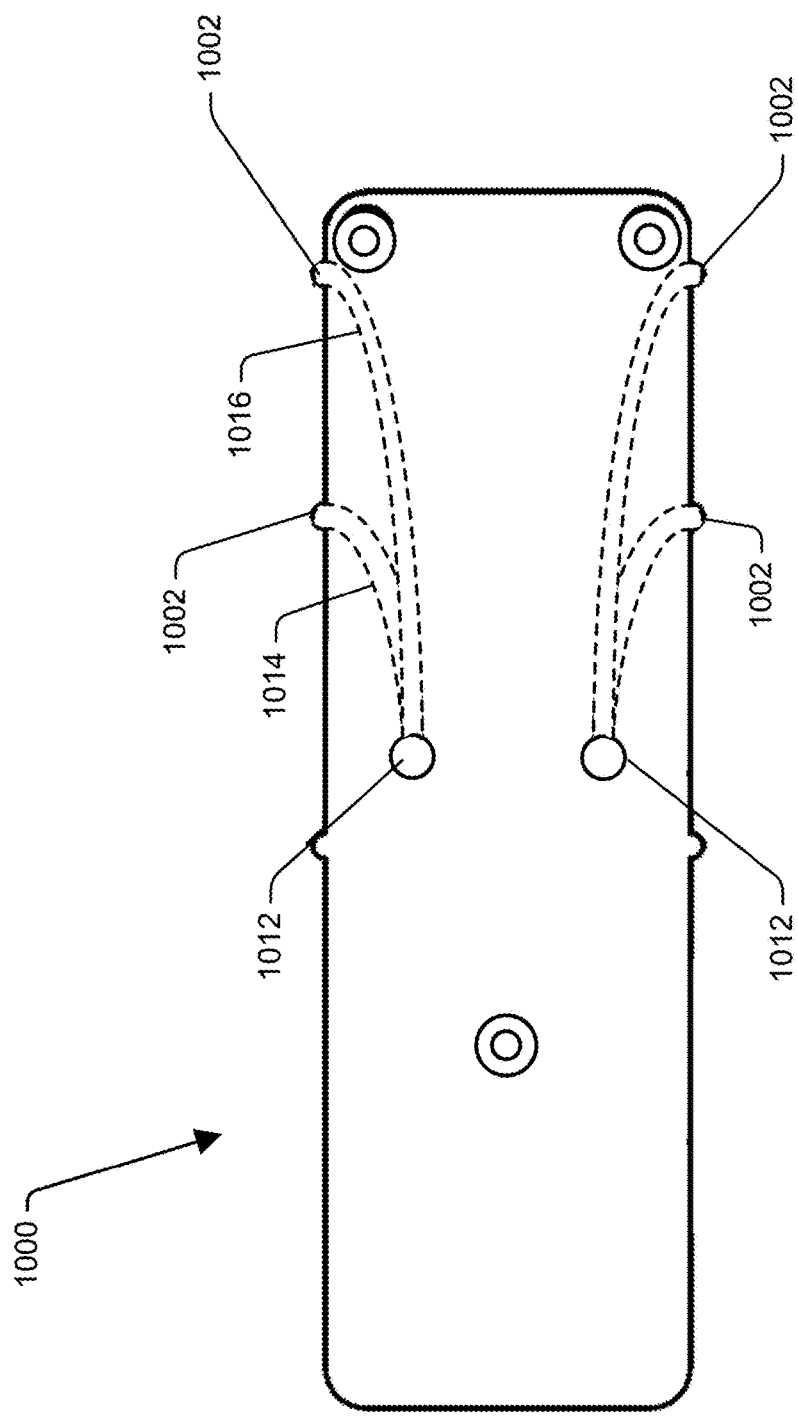
FIG. 43 is a top plan view of another sensor clip device that is consistent with at least some aspects of the present disclosure.
Figure 44:
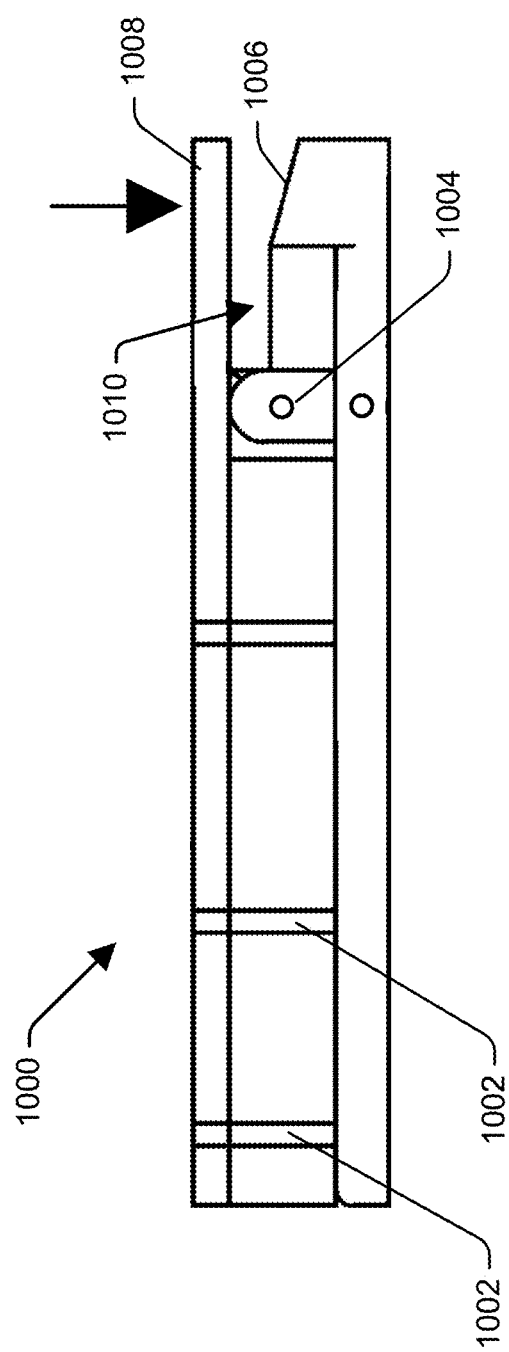
FIG. 44 is a side view of the clip device of FIG. 43 in a closed state.
Figure 45:
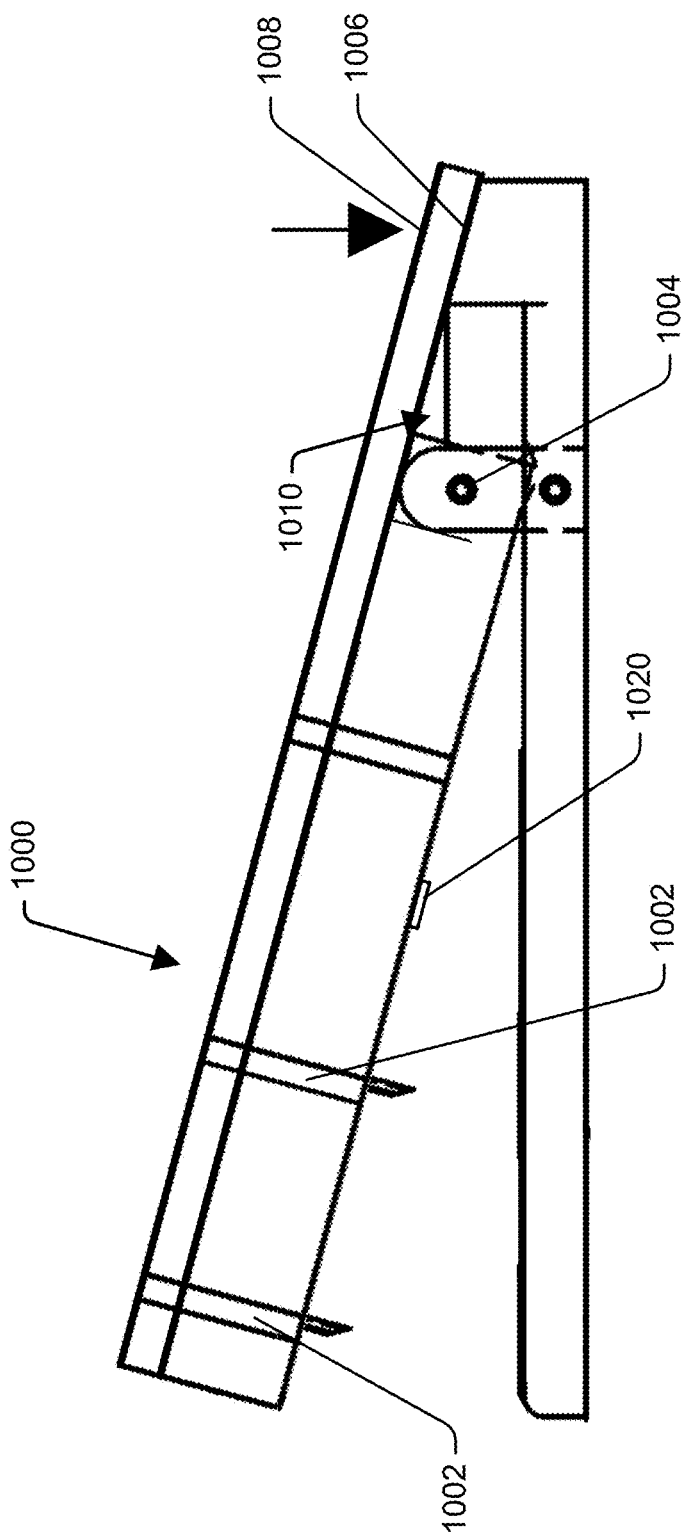
FIG. 45 is a side view of the clip device of FIG. 43 in an open state.

Referring now to FIGS. 43 through 45, yet another sensor clip embodiment 1000 is illustrated that is similar in many respects to the embodiments described above, but which has a few additional improvements. Many of the features of clip 1000 are similar to those described above with respect to the other embodiments and therefore, in the interest of simplifying this explanation only the unique features of clip are described hereafter. It should be appreciated that other combinations of clip features are contemplated where features from any of the disclosed embodiments may be swapped in for similar features in other embodiments.

Instead of having recesses as guiding indicia as shown in clip 500, clip 1000 includes ribs 1002 that extend proud of the external surface of the clip housing. The can be detected via touch and also eliminate the crevices that are formed by alignment recesses so that clip 1000 should be easier to clean and sterilize. In addition, in at least some cases, the ribs may be painted with or otherwise formed using a glow in the dark material so that the ribs can be better seen during night use.

Referring still to FIG. 43, two indicators are shown at 1012. Here, each indicator includes a cylindrical light pipe where the internal end of each pipe resides adjacent an LED or other light source within the sensor clip housing. The indicators 1012 are controlled to indicate when a circuit connection is made, when a circuit connection is not completed, when a connected pad is damp, soaked, etc., and other clip and system conditions.

In some cases additional light pipes may be included in the clip assembly for periodically providing light for other purposes. For instance, see the phantom light pipes shown at 1014 and 1016 that extend from the same internal LEDs as pipes 1012 to the indicia for lighting up the indicia for nighttime use. Here, the side light pipes can be used to align the contacts with traces and/or as additional indicating devices.

As another instance, see that a bottom end of another light pipe is shown at 1020 in FIG. 45, 1020 for shining light within the clip gap when the clip is in an open state. Here, the gap light 1020 would be off when the clip is in a closed state but would automatically turn on when the clip is opened to shine light within the gap helping a user see an edge of pad during attachment. Thus, one of a small set of LEDs may be used with one or more light pipes to provide guiding light as well as to indicate different sensing conditions. In some cases one LED may be controllable to generate many different light colors as guiding light or to indicate different states. In some cases the side and in gap light pipes may simply be replaced by LEDs that are illuminated at different times or there may be several LEDs mounted on one or both sides of the PCB that are aligned with light pipes as described above.

Referring again to FIGS. 44 and 45, the hinge 1004 is spaced from a nearest end of clip assembly 1000 and the clip housing forms an extending finger 1008 which is spaced from a facing surface 1006 of the jaw member to form a gap 1010. Here, when the clip is in the closed position as shown in FIG. 44, a user can press finger 1008 downward toward surface 1006 to close the gap 1010 and open the clip jaw while attaching the clip to an edge of a pad or when removing the clip from a pad edge. Here, there is no need for the finger recesses shown in the clip embodiment 500. This clip design is advantageous as the surface 1006 can be angled to interfere with a facing surface of finger member 1008 in which the clip is opened to an optimal angle for installing or removing the clip. Again, in at least some embodiments the optimal angle may be substantially 15 degrees although other angles are contemplated.

Referring still to FIGS. 44 and 45, in at least some embodiments the finger 1008 may have a length dimension relative to the overall clip length that is designed so that a user can apply ample leverage to the finger to cause the clip to open. For instance, in at least some cases the length of finger 1008 may be anywhere between 10 and 30% of the total length of the clip 1000 and, in particularly advantageous embodiments the length may be substantially 20% of the total clip length. For example, where clip 1000 is 3.75 inches long, the finger may be around 0.80 inches long.

In cases where a clip at the edge of a pad is soiled, most soiling occurs near the inner end of the clip arrangement as opposed to the outer end. For this reason, another advantage associated with clip 1000 shown in FIGS. 43-45 is that the clip can be opened by applying pressure at the outer end of the clip (e.g., at finger 1008) as opposed to having to contact and manipulate the inner end at finger recesses 508 and 510 of the clip as required when using the clip 500 shown in FIG. 19.

Figure 46:
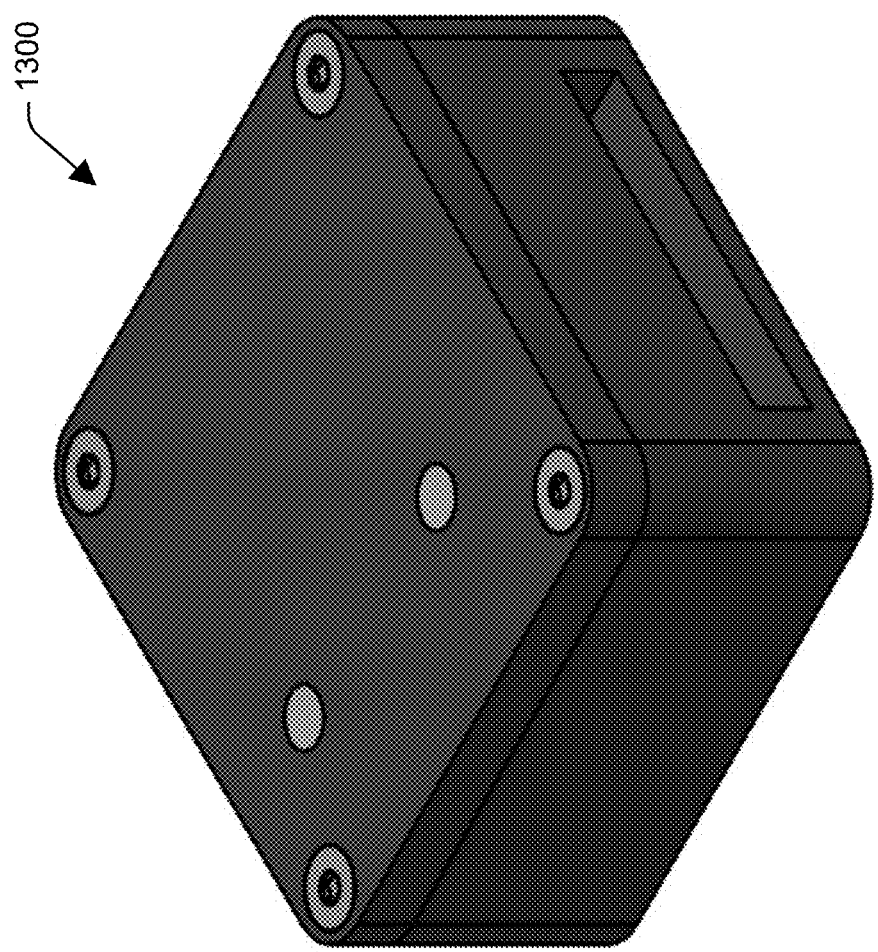
FIG. 46 is a perspective view of a supplemental sensing housing that is consistent with at least some aspects of the present disclosure.

FIG. 46 shows another version 1300 of the supplemental battery and processor housing 702 shown in FIG. 29 which includes a sealed housing. Here, a sensor clip would be wired (not shown) to the supplemental assembly 1300 as shown in FIG. 29 is at least some embodiments and the assembly 1300 could be spaced somewhat away from a patient for easier observation, access, etc. Here, as in the description of FIG. 29 above, a sensor processor, indicator lights, a speaker, etc., may all be provided within the assembly 1300 housing so that only a very simplified clip arrangement including contacts for connecting to pad traces would be required. Again, the advantage here is that costly parts of the sensor clip are located within the assembly 1300 so that those parts can be sterilized easier and reused with more than one patient.

In at least some cases a contact clip may also include a wireless transmitter and assembly 1300 may also include a wireless receiver for communicating sensed data via Bluetooth or some other NFC protocol from the contact clip to assembly 1300 so that the wires can be eliminated.

In at least some embodiments it is contemplated that a clip type sensor device may include other components. For instance, referring again to FIG. 5, as described above, in some embodiments audio indicator 82 may include a speaker device that can audibly present a voice signal to indicate different clip states and the clip 22 may also include microphone 1030 for receiving voice signals from a patient or an assistant. As shown, microphone 1030 is linked to the assembly processor 80. The processor 80 may be programmed to operate as a smart computing device to perform a small set of functions. For instance, in some cases the processor may be programmed to field a small subset of queries from a patient or an assistant regarding sensor system status. For instance, a patient may be anxious about the state of a sensing pad (e.g., if it is wet, damp, dry, operating properly, etc.) when she wakes up in the middle of the night. Here, instead of fumbling around to locate the clip, the patient may simply utter the query "Is my wetness sensor still working?" or "What is the status of my wetness pad?" In some cases the processor may monitor for a wakeup word like "Alertwet" or something like that prior to listening for a query or command from a patient/assistant.

Here, when the processor receives a query, the processor determines the nature of the question using AI and can formulate an answer based on an instantaneous detection of pad condition or on a prior detected as stored pad state. For instance, the answer may be "Your pad is completely dry at this time" or "Your pad is slightly damp." As another instance, a patient may query "How much time until my next restroom reminder?" and the processor may respond "32 minutes." Here, the idea is any anxiety on the part of the patient can be addressed with a simple question and automated answer so that the patient need not both with physically locating the clip or manually checking the condition of the pad.

In a case where a patient wants an assistant to address the pad condition, the clip processor may be programmed to facilitate communication with an assistant. For instance, if the processor tells a patient that a pad is somewhat wet and the patient is uncomfortable for some reason and wants the pad replaced, the patient may be able to voice a request for an assistant to come to the patient's room to attend to the wet pad.

In cases where an assistant comes into a patient's room to check on the patient, again, instead of having to fumble around looking for a sensing clip, the assistant may simply voice a query regarding the sensing system status to access audibly broadcast state information. The assistant may query "Alertwet, what is the status of the wetness pad?" and the processor may answer "The pad is partially wet, however, you should change it now as the patient is due for a restroom alert 15 minutes from now." Here, the assistant may continue and query "How long as the pad been wet?" and the processor may respond "45 minutes."

As briefly described above, in at least some cases it is contemplated that a smart speaker type device (see 27 in FIG. 1) may be provided in addition to or to operate along with any one of the clip type devices described above. For instance, an Alexa type computing device may be provided in a patient's room within a medical facility for interacting with a clip device like the ones described above. Here, it should be noted that many smart computing devices are relatively inexpensive so that it should be expected that many medical facilities may soon be equipped with a smart speaker in each patient room for various purposes.

Unless indicated otherwise, herein an Alexa, Google or other type voice activated smart computing device will simply be referred to as a "smart speaker". Here, the smart speaker may perform many different functions relatively inexpensively. First, the smart speaker may be programmed to facilitate a sensor clip commissioning process whereby a specific clip is associated with the specific smart speaker. For instance, when a clip is brought into a patient's room and is opened (e.g., the clip jaw is opened), the clip may transmit a Bluetooth signal within the room announcing itself to the smart speaker. Here, the smart speaker may audibly query if the assistant wants to associate the clip device with the smart device and upon an affirmative answer, may associate with the clip and cause the clip to chirp or clip light devices to blink to confirm association. Association may also be triggered by attaching a clip to a sensing pad or by some other triggering activity.

Once associated with a smart speaker, the clip may then transmit sensor system state signals from a clip processor. For instance, when the clip is attached to a sensor pad, the clip may send a signal to the smart speaker indicating a successful circuit and the smart speaker may audibly indicate "Alertwet sensor system now operational." The smart speaker may be programmed to route system state signals to a remote computer or portable computing device used by an assistant or to the system server for further processing. The smart speaker may also be programmed to generate warning signals when specific system states occur such as, for instance, a wet pad state. Here, the smart speaker may generate a light warning signal, a sound warning signal, a voice signal, and/or a signal to transmit to a remote computer of the system server.

In some embodiments the smart speaker will include a microphone and will be able to answer verbal patient and/or assistant queries like the ones described above either onboard the smart speaker or by connecting to an AI server 28 in the cloud that is programmed to process queries, lookup information needed to answer queries and to formulate audio or other signals in response to the queries. Thus, a patient or assistant may query the state of a sensing system, if the system is operating properly, etc.

In at least some cases a smart device may be specially programmed to only perform functions related to the wetness sensing system. In other cases the smart device may be used to perform other healthcare or medical related functions (e.g., monitor other medical equipment states, provide other warnings, etc.). In still other cases the smart device may be a general purpose smart device like Alexa where the device just runs a wetness sensing system application program in parallel with all the other functions that the smart device can perform.

In at least some embodiments where different sensor pad types having different trace shapes, lengths, and operational characteristics are available for use in different types of wetness sensing applications (e.g., bed wetting, within a cast, in a diaper, etc.), specific and different types of sensor clip systems may be designed to operate with each different sensing pad or strip type so that the sensor clips only need to be programmed to account for the specific operating characteristics of a specific pad/strip type. Thus, for instance, in a case where two pad/strip types are available for use, a first rectangular bed pad type 12 as shown in FIG. 1 and a second ankle cast strip type as shown in FIG. 34, in at least some cases first and second differently programmed clip types may be used with the pad and strip, respectively. In cases where there are five different laminate types, five differently programmed clips would be provided, one for each laminate type. Here, to ensure that correct clip types are used with specific pad types, an end resistor (see 324 in FIG.

16) may be integrated into each pad where the resistors in different pad types have different values. Here, upon attaching a sensor clip to a pad, the sensor processor may detect the resistive value integrated into the pad and generate an alert signal when the clip is the wrong type for the pad, prompting the user to retrieve a different clip type.

In other cases it is contemplated that a single clip type may be able to operate with many different sensor pad types where the single clip type modifies its operations based on the type of pad that the clip is attached to. For instance, in some cases a sensor clip processor may be able to read a pad type identifier that is provided directly on a pad. For example, in the case of a pad like the one shown in FIG. 16 that includes one or more integrated resistors 324, the value of the resistor may specific to a specific pad type and therefore, upon initial connection and activation of a sensor clip, the clip processor may determine the pad type from the initially detected resistance and the clip may thereafter load or access and use a subprogram associated with that specific pad type to perform operations. As another example, a barcode, matrix code, or some other indicia may be provided on a pad at a sensor clip connection location (e.g., see location 17 in FIG. 2a) and a clip may be equipped with a code reader for reading the code when the clip is aligned with the code indicia on the pad.

In some cases an assistant may have to do something during a pad and clip commissioning process to make pad type known to the sensor clip processor. For instance, in some cases bar/matrix codes may be provided on each pad indicating pad type and on each sensor clip identifying the specific clip and an assistant using a smart phone or other code reader may be required to read both a pad code and a clip code to associate the clip with the pad. Once a smart phone associates a clip and an instance of a pad, the phone may transmit a pad type indicator to the clip causing the clip, again, to load and run a subprogram that is associated with the pad type.

In still other cases the sensor clip may simply operate as a raw data reader, data router, and state indicator where all data calculations, conclusions and storage occur at a system server 28 or some other system computing device. Here, for instance, where a sensor clip reads a pad type code or a smart phone or other smart device associates a clip with a specific pad type in some fashion, the pad type and associated clip identifier may be provided to server 28 which then runs subprograms for the specific pad type and clip combination to facilitate system processes. Here, when an alert is required, the server may transmit alert signals to one or each of the sensor clip, an assistant's computing device, and another warning device (e.g., a smart speaker in a patient's room) as needed.

In still other cases it is contemplated that a patient may have her own smart phone capable of running application programs where one of the programs may be a wetness sensor program capable of performing at least a subset of the processes and providing a subset of the features described above in conjunction with a sensor clip and sensor pads. To this end, with a wetness sensor program loaded onto a smart phone device that has Bluetooth communication capabilities, the patient may associate a sensor clip with the smart phone by entering clip identifying information, reading a bar code from the clip device using a smart phone camera, performing a commissioning procedure where the clip broadcasts an identifying signal and the phone uses that signal to establish a relationship, or in some other fashion.

Once the clip and phone are associated, the patient or an assistant may place a sensing pad or strip on a bed surface or otherwise for sensing wetness and may attach the sensing clip (and resistive clip where used) to the pad/strip, at which point the sensor clip may start monitoring for wetness. Here, as described above, the sensor and/or smart phone device may perform some process to identify pad type in cases where the system supports more than one pad type with different operating characteristics and may run a subprogram that is related to a specific pad type.

Here, the clip may simply collect raw data and send it along to the patient's phone device for processing or for further transmission on to a system server (see again 28 in FIG. 1) for processing. Alerts may be provided to the patient via the sensor clip, the patient's smart phone, or both. Alerts may also be transmitted to an assistant in at least some cases. In many cases smart phones have voice capabilities built in and therefore alerts may be provided via voice messages and voice queries from the patient may be received, processed and responded to as described above in the context of other smart devices.

While the invention may be susceptible to various modifications and alternative forms, specific embodiments have been shown by way of example in the drawings and have been described in detail herein. However, it should be understood that the invention is not intended to be limited to the particular forms disclosed. For example, while at least some of the embodiments above include a clear or at least semi-transparent cover member so that visual LED signaling can be observed from outside a sensor clip housing, in other embodiments the entire housing structure may be semi or fully transparent and the clip assembly may be designed so that LED light exists in many directions from the housing and can be seen generally from any vantage point about the housing structure. In these cases light signaling should be viewable from a clip LED regardless of how the clip is attached to a sensing assembly.

In at least some cases, after pad and sensor clip initiation using a resistive clip wherein the pad/trace length is determined, the resistor clip may be removed and the sensor clip may operate alone to detect wetness without the resistive clip.

While the pads described above include two conductive/resistive traces that extend along each other from end to end where each trace has an intentionally defined resistance per unit length, in other embodiments it is contemplated that only one of the two traces may be intentionally resistive and the other trace may be essentially purely conductive.

While most of the pads described above include separate traces printed on the same level within a pad laminate, in other cases it is contemplated that first and second traces may be printed on opposite sides of an absorptive layer where, when the absorptive layer is dry, there is no electrical short between the two traces and, where wetness in the absorptive layer causes a short between the two traces. Here, the first and second traces could be essentially identical, with an upper trace simply separated from the lower by the absorptive layer. This arrangement would operate in a fashion similar to the dual trace pads described above for detecting wetness, location of wetness, etc.

Thus, the invention is to cover all modifications, equivalents, and alternatives falling within the spirit and scope of the invention as defined by the following appended claims. To apprise the public of the scope of this invention, the following claims are made:

What is claimed is:

1. A sensor pad assembly for detecting wetness, the pad assembly comprising:
   a breathable polyethylene base layer;
   a first carbon black trace printed on a top surface of the base layer in a first serpentine pattern;

a second carbon black trace printed on the top surface of the base layer in a second serpentine pattern that does not overlap the first trace, wherein at least a portion of the second trace is adjacent each portion of the first trace; and an absorbing subassembly including non-woven layers that envelope a super absorbent polymer (SAP) material, the absorbing subassembly adhered to the top surface of the base layer over the first and second traces;

wherein, each of the first and second carbon black layers has a pH level greater than seven and less than 10 with 0.5 to 5% surfactant and 0.5 to 5% drying solution.

2. The pad assembly of claim 1 wherein at least portions of each of the first and second traces are exposed for connection to a sensing clip assembly.

3. The pad assembly of claim 1 wherein each trace has a first end and a second end at an end of the trace opposite the first end, at least first ends of the first and second traces are adjacent an edge of the base layer far the assembly further including a sensing clip releasably connected to the edge and including at least first and second electrical contacts to contact the first and second traces proximate the first ends of the first and second traces, respectively.

4. The pad assembly of claim 3 wherein a resistor device is coupled between the second ends of the first and second traces.

5. The pad assembly of claim 4 wherein the base layer is substantially rectangular having at least a first edge wherein the first ends and the second ends of the first and second traces are adjacent the first edge.

6. The pad assembly of claim 4 wherein the second ends of the first and second traces are adjacent an edge of the base layer.

7. The pad assembly of claim 6 wherein the resistor device is a resistive clip that is releasably connected to the edge, the resistive clip including at least first and second electrical contacts to contact the first and second traces, respectively.

8. The pad assembly of claim 7 including indicia printed on a top surface of the pad assembly indicating where the sensor clip and the resistive clip are to be attached to the edge.

9. The pad assembly of claim 3 wherein second ends of the first and second traces are adjacent an edge of the base layer, the assembly further including a resistive clip releasably connected to the edge and including at least first and second electrical contacts to contact the first and second traces, respectively.

10. The pad assembly of claim 3 wherein the first and second contacts contact the first and second traces at first and second contact locations, respectively, and wherein the first contact location is closer than the second contact location to the edge of the base layer.

11. The pad assembly of claim 10 wherein the first and second contact locations are formed by portions of the traces that run substantially parallel to the edge of the base layer to which the clip is attached.

12. The pad assembly of claim 3 wherein the first and second contacts include first and second pins and wherein the first and second pins pierce the first and second traces when the sensing clip is connected to the edge.

13. The pad assembly of claim 12 wherein the sensing clip includes first and second jaw members hinged together as a proximal end and forming first and second jaw surfaces, respectively, the pins extending from the first jaw surface, the second jaw surface forming first and second openings aligned with the first and second pins, respectively, the clip moveable between open and closed positions and distal ends of the first and second pins received in the first and second openings when the clip is in the closed position.

14. The pad assembly of claim 3 wherein the sensor clip includes first and second jaw members hinged at proximal ends for movement between closed and open positions, the first and second jaws forming first and second jaw surfaces, the first and second contacts exposed at the first and second surfaces, the clip further including a magnet having a magnetic surface that is substantially flush with the first jaw surface and a metal member that is substantially flush with the second jaw member and that is aligned with the magnetic surface when the clip is in the closed position.

15. The pad assembly of claim 1 wherein the base layer is rectilinear having a width dimension and a length dimension and wherein the traces extend at least in part along the length dimension.

16. The pad assembly of claim 15 wherein the width dimension extends between first and second base layer edges, the first trace includes a series of substantially identical trace portions, each trace portion having a first end and a second end and first, second, third, and fourth subportions, the first subportion in each trace portion extending from the first end adjacent the first base layer edge to a location adjacent the second base layer edge, the third subportion in each trace portion spaced apart from the first subportion in each trace portion and extending from a location adjacent the second base layer edge to a location adjacent the first base layer edge, the second subportion in each trace portion extending between and connecting ends of the first and third subportions in the trace portion proximate the second base layer edge, and the fourth subportion in each trace portion extending between and connecting ends of the third subportion in the trace portion and a first subportion in an adjacent trace portion proximate the first base layer edge.

17. The pad assembly of claim 16 wherein the second trace includes subportions that extend along each of the first, second, third and fourth subportions of each of the first trace portions.

18. The pad assembly of claim 17 wherein each of the first and third subportions are substantially straight and parallel and extend perpendicular to the length dimension of the base layer.

19. The pad assembly of claim 18 wherein each of the second and fourth subportions are substantially straight and extend along the length dimension of the base layer.

20. The pad assembly of claim 19 wherein the pad assembly is formed as a continuous pad structure extending along a structure length dimension wherein the assembly length is formed by detaching the pad assembly from the continuous pad structure.

21. The pad assembly of claim 20 wherein the first and second ends of the traces terminate at edges of the assembly on opposite sides of the width dimension of the base layer.

22. The pad assembly of claim 1 wherein the first trace includes a first end and a second end and the second trace includes a first end and a second end, the first ends of the traces adjacent an edge of the pad assembly for connection to a wetness sensing device, the assembly further including an integrated resistor between the second ends of the first and second traces.

23. The pad assembly of claim 1 wherein a portion of the first trace is adjacent each portion of the second trace.

24. The pad assembly of claim 1 further including an upper tissue layer located between the SAP layer and an upper non-woven layer and a lower tissue layer located between the SAP layer and a lower non-woven layer.

25. A sensor pad assembly for detecting wetness, the pad assembly comprising:
- a breathable polyethylene base layer;
- at least one non-woven layer;
- a first carbon black trace printed on at least one of the lower non-woven layer and the base layer in a first trace pattern;
- a second carbon black trace printed on the at least one of the non-woven layer and the base layer in a second trace pattern that does not overlap the first trace pattern, wherein at least a portion of the second trace is adjacent each portion of the first trace;
- the non-woven layer adhered to the base layer; and
- an absorbing subassembly including a super absorbent polymer (SAP) material coupled to the non-woven layer; and
- wherein the first trace includes a first end and a second end and the second trace includes a first end and a second end, the first ends of the traces adjacent an edge of the pad assembly for connection to a wetness sensing device; and
- a resistor device connecting the second ends of the first and second traces.

26. A sensor apparatus for detecting wetness, the apparatus comprising:
- a sensor pad subassembly including at least one of a breathable polyethylene base layer and a non-woven layer;
- a first carbon black trace applied to the one of the base layer and the non-woven layer in a first serpentine pattern;
- a second carbon black trace applied to the one of the base layer and the non-woven layer in a second serpentine pattern that does not overlap the first trace, wherein at least a portion of the second trace is adjacent each portion of the first trace, first ends of the first and second traces extending to locations adjacent an edge of the sensor pad and second ends of the first and second traces extending to locations adjacent an edge of the sensor pad; and
- a sensor assembly including electrical connecting pins releasably mounted to the edge of the sensor pad with first and second pins piercing and electrically contacting the first ends of the first and second traces; and
- a resistor assembly including electrical connecting pins and a resistor mounted to the edge of the sensor pad with first and second pins piercing and electrically contacting the second ends of the first and second traces.

27. A sensor assembly for detecting wetness, the assembly comprising:
- a sensor pad subassembly including a breathable polyethylene base layer;
- at least a first non-woven layer;
- a super absorbent polymer (SAP) material layer;
- at least a first non-woven layer located between the SAP layer and the base layer;
- a first carbon black trace applied to one of a top surface of the base layer and the first non-woven layer in a first pattern;
- a second carbon black trace applied to one of a top surface of the base layer and the first non-woven layer in a second pattern that does not overlap the first trace, wherein at least a portion of the second trace is adjacent each portion of the first trace, first ends of the first and second traces extending to locations adjacent an edge of the one of the base layer and the first non-woven layer on which the traces are applied, second ends of the first and second traces extending to locations adjacent an edge of the one of the base layer and the first non-woven layer on which the traces are applied; and
- an absorbing subassembly including a super absorbent polymer (SAP) material coupled to the base layer; and
- a sensing arrangement coupled to the first ends and the second ends of the traces and controlled to alternately apply an excitation voltage to the first ends and detect a first current at the first ends and use the detected first current to identify a first edge portion of a wet spot on the sensor pad subassembly and apply an excitation voltage at the second ends and detect a second current at the second ends and use the detected second current to identify a second edge portion of the wet spot on the sensor pad subassembly.

* * * * *